US012685648B2

(12) United States Patent
Davis et al.

(10) Patent No.: US 12,685,648 B2
(45) Date of Patent: Jul. 21, 2026

(54) RETENTION ASSEMBLIES FOR INTERVERTEBRAL DEVICES

(71) Applicant: Expanding Innovations, Inc.,
Mountain View, CA (US)

(72) Inventors: John Davis, Sunnyvale, CA (US); Ron Sacher, Boca Raton, FL (US); Al Mirel, Redwood City, CA (US)

(73) Assignee: Expanding Innovations, Inc.,
Mountain View, CA (US)

( * ) Notice: Subject to any disclaimer, the term of this patent is extended or adjusted under 35 U.S.C. 154(b) by 0 days.

(21) Appl. No.: 18/627,206

(22) Filed: Apr. 4, 2024

(65) Prior Publication Data

US 2025/0241767 A1     Jul. 31, 2025

Related U.S. Application Data

(60) Provisional application No. 63/627,020, filed on Jan. 30, 2024.

(51) Int. Cl.
A61F 2/46       (2006.01)
A61B 17/00     (2006.01)
A61F 2/30       (2006.01)

(52) U.S. Cl.
CPC ............ A61F 2/4611 (2013.01); A61B 17/00 (2013.01); A61B 2017/00477 (2013.01); A61F 2002/30537 (2013.01)

(58) Field of Classification Search
None
See application file for complete search history.

(56) References Cited

U.S. PATENT DOCUMENTS

| | | | |
|---|---|---|---|
| 11,986,398 B2 * | 5/2024 | Butler ..................... A61F 2/447 |
| 2014/0012384 A1 | 1/2014 | Kana et al. |
| 2014/0039623 A1 | 2/2014 | Iott et al. |
| 2014/0046448 A1 | 2/2014 | Kana et al. |
| 2014/0277513 A1 | 9/2014 | Fessler et al. |
| 2015/0245859 A1 | 9/2015 | McMillen et al. |
| 2016/0296341 A1 | 10/2016 | Tatsumi |
| 2017/0014239 A1 | 1/2017 | Seifert et al. |
| 2017/0014244 A1 | 1/2017 | Seifert et al. |
| 2017/0224389 A1 | 8/2017 | Tatsumi |
| 2018/0042732 A1 | 2/2018 | Seifert et al. |
| 2018/0214280 A1 | 8/2018 | Seifert et al. |
| 2019/0328540 A1 | 10/2019 | Seifert et al. |

(Continued)

*Primary Examiner* — Tessa M Matthews
(74) *Attorney, Agent, or Firm* — McHale & Slavin, P.A.

(57) ABSTRACT

Consistent with the present disclosure, retention assemblies for maintaining the relative position of adjacent vertebral bodies and an implantable device positioned therebetween are described herein. Such retention assemblies may include a plate body and a coupler. The plate body may include structures to allow fixedly attaching the retention assembly to adjacent intervertebral bodies, using vertebral body screws or the like, for example. Furthermore, the coupler may include expandable structures to engage a portion of an implantable device to fixedly attach the retention assembly to the implantable device. Accordingly, once the retention assembly is deployed, the implantable device is fixedly held in relation to the adjacent vertebral bodies, decreasing post operative movement of the implantable device relative to the adjacent vertebral bodies.

15 Claims, 44 Drawing Sheets

(56)                    References Cited

U.S. PATENT DOCUMENTS

| 2021/0315707 | A1  | 10/2021 | Keller et al. |            |
|--------------|-----|---------|---------------|------------|
| 2022/0000633 | A1  | 1/2022  | Seifert et al. |           |
| 2022/0133493 | A1  | 5/2022  | Josse et al.  |            |
| 2023/0372122 | A1* | 11/2023 | Martin        | A61F 2/30771 |
| 2024/0325163 | A1* | 10/2024 | Betz          | A61B 17/8888 |
| 2025/0213373 | A1* | 7/2025  | Burkholder    | A61F 2/4611 |

* cited by examiner

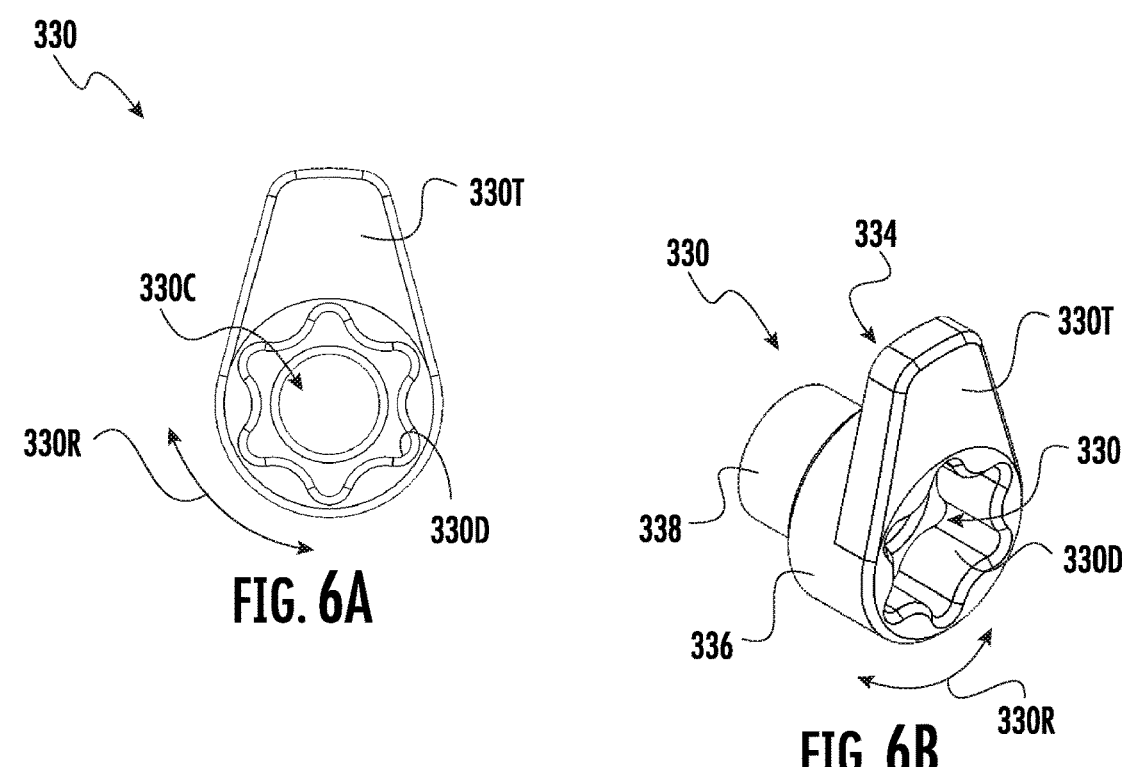
FIG. 6A
FIG. 6B
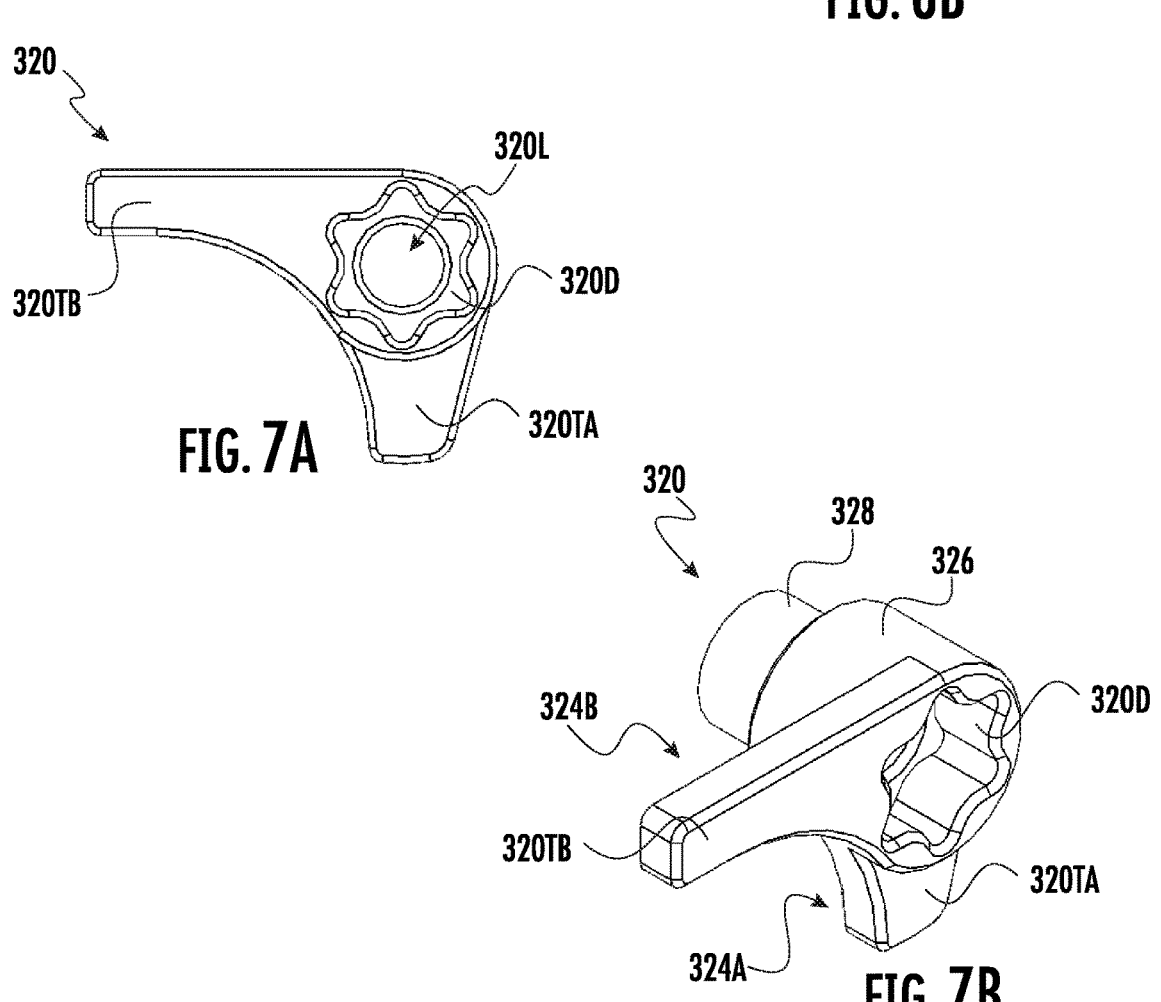
FIG. 7A
FIG. 7B 430
430C2
430C3
436B
434
430T
430B
436A
438
432    430C4    430C1
FIG. 9A
430    430T
434
436B    436A
430C2
430C3    430C1
FIG. 9B    438    432
430
430C2    438
434
430T    430C3    430B
436B    430C4    438
FIG. 9C
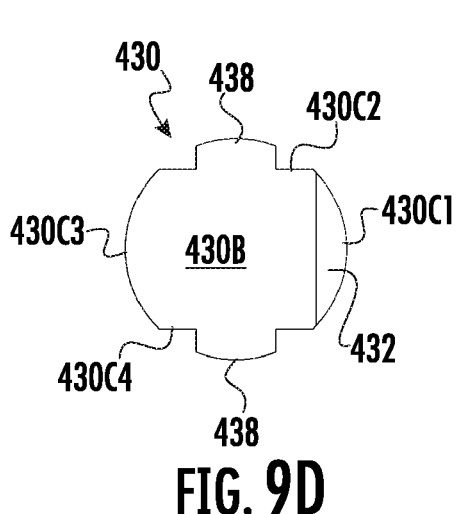
430    438    430C2
430C3    430B    430C1
430C4    432
438
FIG. 9D
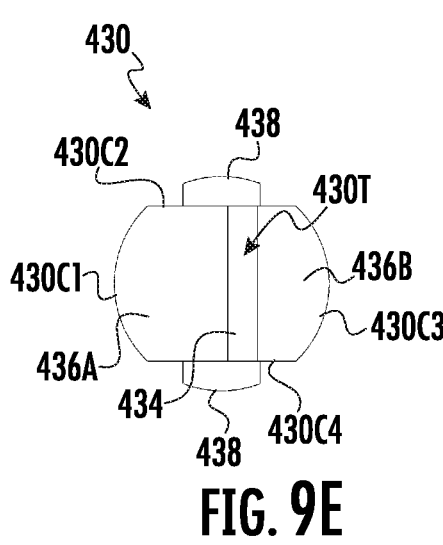
430
430C2    438
430T
430C1    436B
430C3
436A    430C4
434    438
FIG. 9E

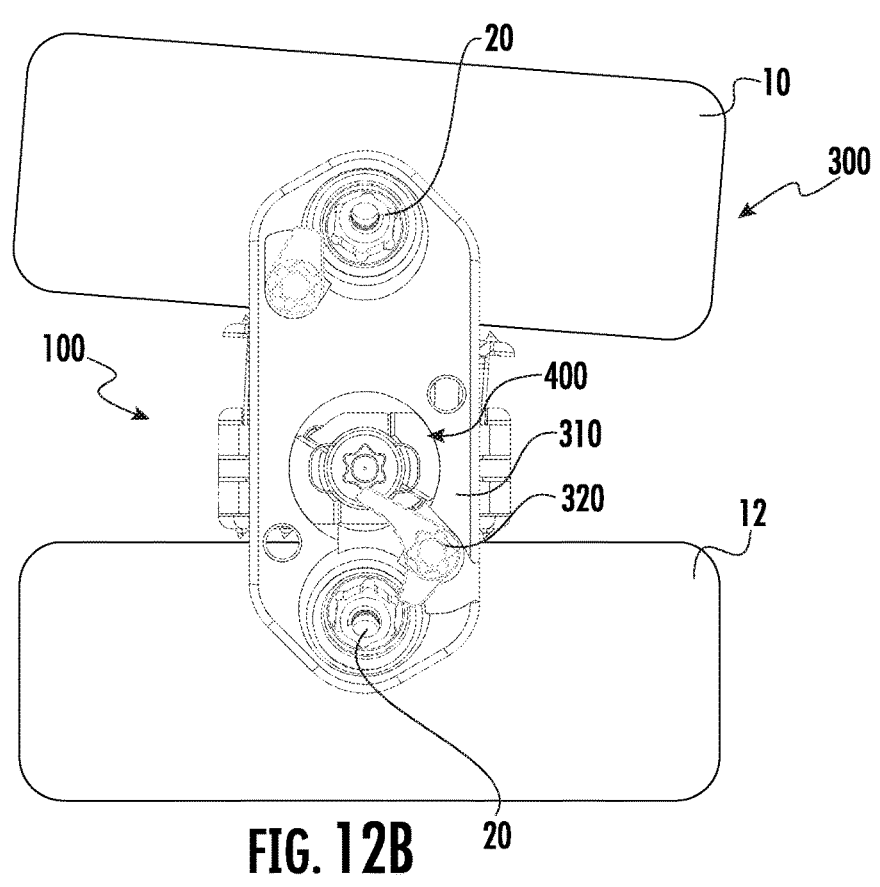
FIG. 12B
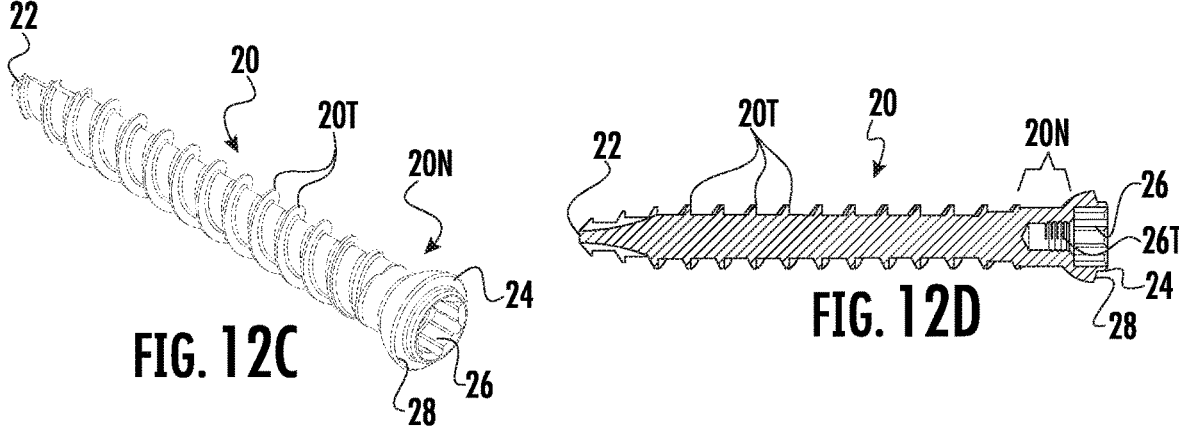
FIG. 12C
FIG. 12D

800

600

810

842

844

630

834

832

844

630

800

810

600

630

810D

840S

840

842

844

840RS

810

840S

RETENTION ASSEMBLIES FOR INTERVERTEBRAL DEVICES

This application claims the benefit of priority to provisional application, Ser. No. 63/627,020, filed Jan. 30, 2024, and entitled, "Retention Assemblies for Intervertebral Devices," and which is incorporated herein by reference, in its entirety.

BACKGROUND

Field of this Disclosure

This application relates generally to medical devices, and more particularly, to medical devices utilized for spinal procedures.

Description of the Related Art

Degenerative disc diseases are common disorders that can impact all or a portion of a vertebral disc, a cushion-like structure located between the vertebral bodies of the spine. Degenerative disc diseases may lead, for example, to a disc herniation where the vertebral disc bulges out or extrudes beyond the usual margins of the disc and the spine. Disc herniation, in particular, is believed to be the result of excessive loading on the disc in combination with weakening of the annulus due to such factors as aging and genetics. Such degenerative disc diseases are also associated with spinal stenosis, a narrowing of the bony and ligamentous structures of the spine. Although disc herniation can occur anywhere along the perimeter of the disc, it occurs more frequently in the posterior and posterior-lateral regions of the disc, where the spinal cord and spinal nerve roots reside. Compression of these neural structures can lead to pain, parasthesias, weakness, urine and fecal incontinence and other neurological symptoms that can substantially impact basic daily activities and quality of life.

Temporary relief of the pain associated with disc herniation, or other degenerative disc diseases, is often sought through conservative therapy, which includes positional therapy (e.g. sitting or bending forward to reduce pressure on the spine), physical therapy, and drug therapy to reduce pain and inflammation. When conservative therapy fails to resolve a patient's symptoms, surgery may be considered to treat the structural source of the symptoms. When surgery fails to resolve a patient's symptoms, more drastic measures may include disc replacement surgery or vertebral fusion.

There are numerous implantable devices that have been developed for disc replacement and vertebral fusion. Such implantable devices, also referred to as cage systems, may be deployed to replace the vertebral disc and fuse the adjacent vertebrae, relieving pain and providing increased mobility to the patient. However, such implantable devices and methodologies have drawbacks. For example, the implantable devices, after deployment, may move relative to adjacent vertebral bodies. In some cases, the implantable devices may move away from the adjacent vertebral devices, which may result in undesirable compressing of the adjacent vertebral bodies and further pain and suffering. Such movement may be due to continued disease of the adjacent vertebral bodies, or the presence of external forces applied to the operative area, including the adjacent vertebral bodies themselves, during the healing process.

Accordingly, there is a need for positionally retaining implantable devices in a proper position relative to adjacent vertebral bodies, which may be referred to as retention assemblies. Such retention assemblies allow for fixedly locating the implantable device relative to the adjacent vertebral bodies reducing movement after an implant procedure and during the healing process. There is also a need for retention assemblies to rigidly hold adjacent vertebral bodies relative to each other, independent of an implantable intervertebral device.

BRIEF SUMMARY

Consistent with the present disclosure, retention assemblies for maintaining the relative position of adjacent vertebral bodies and an implantable device positioned therebetween are described herein. Such retention assemblies may include a plate body and a coupler. The plate body may include structures to allow fixedly attaching the retention assembly to adjacent intervertebral bodies, using vertebral body screws or the like, for example. Furthermore, the coupler may include expandable structures to engage a portion of an implantable device to fixedly attach the retention assembly to the implantable device. Accordingly, once the retention assembly is deployed, the implantable device is fixedly held in relation to the adjacent vertebral bodies, decreasing post operative movement of the implantable device relative to the adjacent vertebral bodies.

In one aspect, a device, in accordance with this disclosure, may include a plate body and a coupler removably attachable to the plate body. The coupler may include an elongate member and a protrusion, the protrusion being adapted to radially move away from a longitudinal axis of the coupler as the elongate member translates from a first retracted configuration to a second inserted configuration. In certain embodiments, the elongate member may include a transition along its length, a longitudinal axis of the protrusion passing through the elongate member on a first side of the transition in the first retracted configuration and the longitudinal axis of the protrusion passing through the elongate member on a second side of the transition in the second inserted configuration.

In some embodiments, the elongate member may include a cylindrical shape and a transition along its length, a first radius on a first side of the transition being less than a second radius of the elongate member on a second side of the transition. In other embodiments, the elongate member includes a rectangular shape and a transition along its length, a first width on a first side of the transition being less than a second width on a second side of the transition.

In certain embodiments, the plate body may include a keyed opening, the coupler being removably attachable to the plate body at the keyed opening. In still other embodiments, the coupler may include a housing having a first lumen therethrough being parallel to a longitudinal axis of the coupler and a second lumen therethrough being perpendicular to the longitudinal axis of the coupler, the elongate member may be further adapted to translate within the first lumen and the protrusion may be further adapted to translate within the second lumen. In other embodiments, the protrusion may be configured to extend out an opening in the housing and couple to an opening of an intervertebral device, in order to fixedly hold the coupler to the intervertebral device when the elongate member is in the second inserted configuration. In still other embodiments, the first lumen of the housing may include a threaded portion and the elongate member may include a threaded portion, the threaded portion of the elongate member being adapted to couple to the threaded portion of the first lumen of the housing such that rotation of the elongate member results in movement of the elongate member within the first lumen of the housing between the first retracted configuration to the second inserted configuration. In other embodiments, the protrusion may be a first protrusion, and the coupler may include a second protrusion slidably positioned within the second lumen of the housing, the elongate member operably extending between the first protrusion and the second protrusion.

In other embodiments, the device may include a cap fixedly attached to the elongate member, the cap may include a transition along its length, a longitudinal axis of the protrusion passing through the elongate member on a first side of the transition when the elongate member is in the first retracted configuration and the longitudinal axis of the protrusion passing through the elongate member on a second side of the transition when the elongate member is in the second inserted configuration.

In another aspect, a kit may include a plurality of plate bodies and a coupler, the coupler removably attachable to each one of the plurality of plate bodies. The coupler may further include an elongate member and a protrusion. The protrusion may be adapted to radially move away from a longitudinal axis of the coupler as the elongate member translates from a first retracted configuration to a second inserted configuration. In some embodiments, the plurality of plate bodies may include at least one plate body configured to fixedly attach to a single vertebral body. In other embodiments, the plurality of plate bodies includes at least one plate body configured to fixedly attach to each of a pair of adjacent vertebral bodies. In yet some other embodiments, one of the at least one plate body may be configured to fixedly attach to each of the pair of adjacent vertebral bodies at more than one attachment point, two attachment points in certain embodiments.

In another aspect, a method may include providing a retention assembly including a plate body, positioning an intervertebral device between a pair of vertebral bodies, positioning the retention assembly such that only a first portion of the plate body is adjacent a first of the pair of vertebral bodies, fixedly attaching the plate assembly to the intervertebral device, and fixedly attaching the retention assembly to the first of the pair of vertebral bodies.

In still another aspect, a method may include providing a retention assembly having a plate body, positioning an intervertebral device between a pair of vertebral bodies, positioning the retention assembly such that a first portion of the plate body is adjacent a first of the pair of vertebral bodies and a second portion of the plate body is adjacent a second of the pair of vertebral bodies, and fixedly attaching the retention assembly to the pair of vertebral bodies. In certain embodiments, fixedly attaching the retention assembly to the pair of vertebral bodies may include fixedly attaching the first portion of the plate body to the first of the pair of vertebral bodies, and fixedly attaching the second portion of the plate body to the second of the pair of vertebral bodies. In other embodiments, the intervertebral device may include an opening with a groove, the method including removably attaching an installation tool to the groove of the opening of the intervertebral device and adjusting a height of the intervertebral device with the installation tool. In still other embodiments, the plate assembly may further include a coupler, and the method may include fixedly attaching the plate assembly to the groove of the opening of the intervertebral device with the coupler. In yet other embodiments, the coupler may include one or more protrusions configurated to radially expand from a central lumen of the coupler, fixedly attaching the plate assembly to the groove of the opening of the intervertebral device, the method including radially expanding at least a first of the one or more protrusions into contact with the groove of the opening of the intervertebral device.

BRIEF DESCRIPTION OF THE DRAWINGS

Reference will be made to embodiments of the disclosure, examples of which may be illustrated in the accompanying figures. These figures are intended to be illustrative, not limiting. Although certain aspects of the embodiments are generally described in the context of these embodiments, it should be understood it is not intended to limit the scope of the disclosure to these particular embodiments. In the drawings:

FIG. 6A is a first tab portion of the plate assembly of FIG. 4A.

FIG. 6B is a perspective view of the first tab portion of FIG. 6A.

FIG. 7A is a second tab portion of the plate assembly of FIG. 4A.

FIG. 7B is a perspective view of the second tab portion of FIG. 7A.

FIG. 9A is a perspective view of an exemplary foot, as part of the exemplary coupler of FIG. 8.

FIG. 9B is a first side view of the exemplary foot of FIG. 9A.

FIG. 9C is a second side view of the exemplary foot of FIG. 9A.

FIG. 9D is a bottom view of the exemplary foot of FIG. 9A.

FIG. 9E is a top view of a portion of the exemplary foot of FIG. 9A.

FIG. 12B is a symbolic end view of the plate assembly of FIG. 4A coupled to both, the intervertebral device of FIG. 1A and adjacent vertebral bodies.

FIG. 12C is a perspective view of an exemplary vertebral body screw.

FIG. 12D is a section side view of the exemplary vertebral body screw of FIG. 12C.

DETAILED DESCRIPTION

Figure 1A:
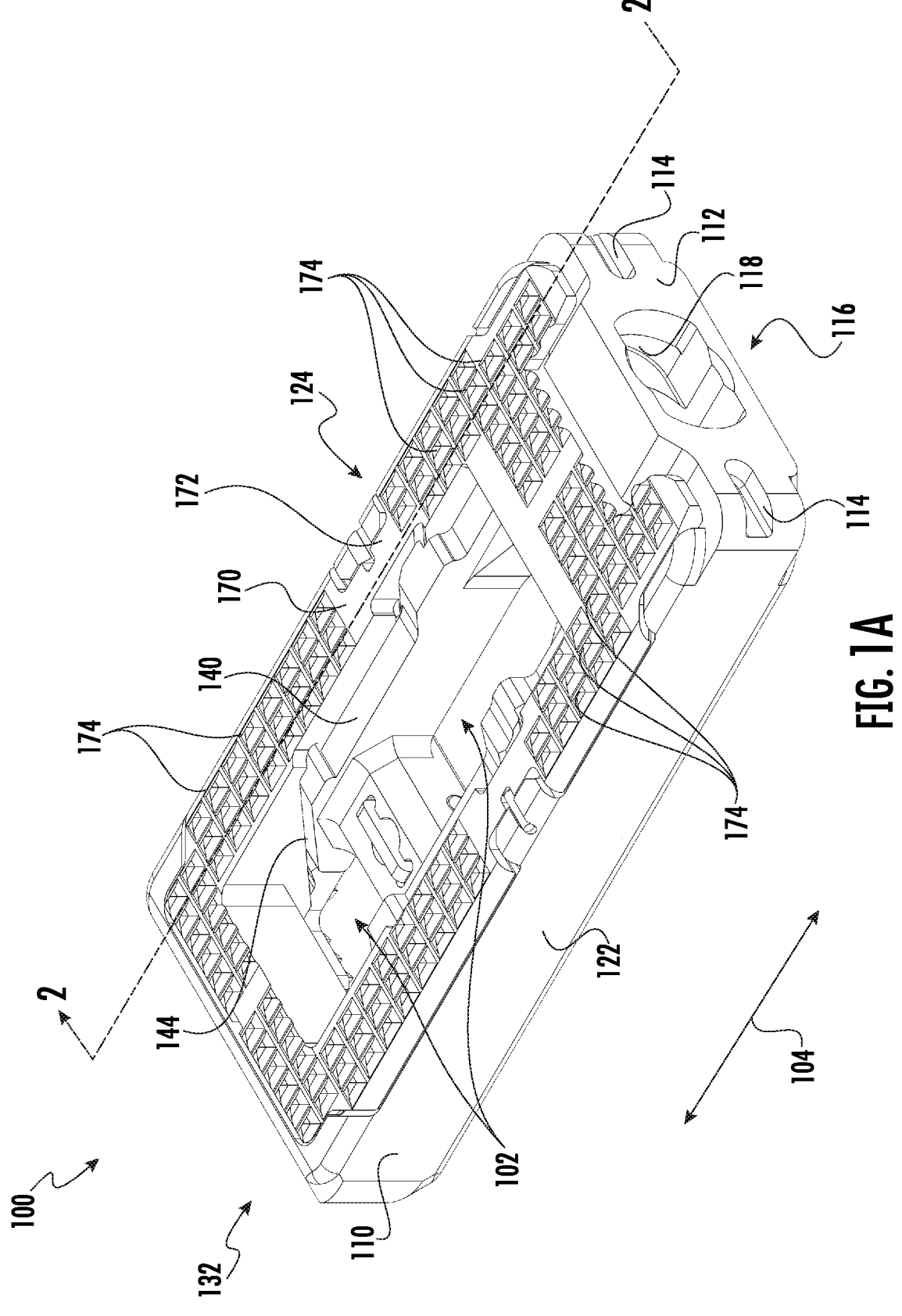
FIG. 1A is a first perspective view of an intervertebral device.

Intervertebral systems incorporating plate assemblies, and methods of their use, are disclosed. Plate assemblies disclosed and contemplated herein are retaining devices intended for maintaining the positional placement of an intervertebral system with respect to surrounding biological tissue, namely vertebral bodies, or independently holding adjacent vertebral bodies relative to an intervertebral system, each which may lead to better fusion between the intervertebral system and such adjacent vertebral bodies.

The following description is set forth for the purpose of explanation to provide an understanding of the various embodiments of the present disclosure. However, as should be apparent to one skilled in the art, embodiments of the present disclosure, or some or all of certain aspects thereof, may be incorporated into a number of different medical devices, assemblies and systems. Structures and devices shown below in cross-section, in block diagram, or in symbolic form are not necessarily to scale and are illustrative of exemplary embodiments. Furthermore, the illustrated exemplary embodiments disclosed or contemplated herein may include more structures or less structures than depicted and are not intended to be limited to the specific depicted structures. While various portions of the present disclosure are described relative to specific structures or processes with respect to a medical device or system using specific labels, such labels are not meant to be limiting.

The intervertebral device retention assemblies described herein may be made from any suitable biocompatible material, including but not limited to metals, metal alloys (e.g. stainless steel or titanium) and polymers (e.g. polycarbonate), and may be formed using any appropriate process, such as screw-machining, molding (e.g. injection molding), or printing. The plate assemblies described or contemplated herein may be sized for various intervertebral devices and vertebral bone vertical spacing.

As used herein when describing the physical connectivity between a plate assembly and an intervertebral device, the term "fixedly" refers to a coupling between the plate assembly and the intervertebral device where the plate assembly and the intervertebral device are at least axially connected. For example, while fixedly coupled, the plate assembly may still be able to rotate and/or axially move with respect to the intervertebral device, if desired, and within a tolerance. For illustration purposes only, the plate assembly, once fixedly coupled to the intervertebral device, may be able to rotate within a range from about 0 degrees to about 20 degrees with respect to the intervertebral device, or about +/−10 degrees off a normal axis of the intervertebral device, for example. Additionally, the plate assembly, once fixedly coupled to the intervertebral device, may be able to axially move with respect to the intervertebral device within a range from about 0 mm to about 5 mm, or within a range from about 0 mm to about 3 mm, or within a range from about 2 mm to about 5 mm, to name a few. Such rotational and axially tolerances may allow for easier coupling of a plate assembly with an intervertebral device during operation, where a longitudinal axis of the intervertebral device and a longitudinal axis of a coupler, as part of the plate assembly and described in greater detail below, are not parallel during coupling, for example.

Reference will now be made in detail to the present exemplary embodiments, which are illustrated in the accompanying drawings.

Figure 1B:
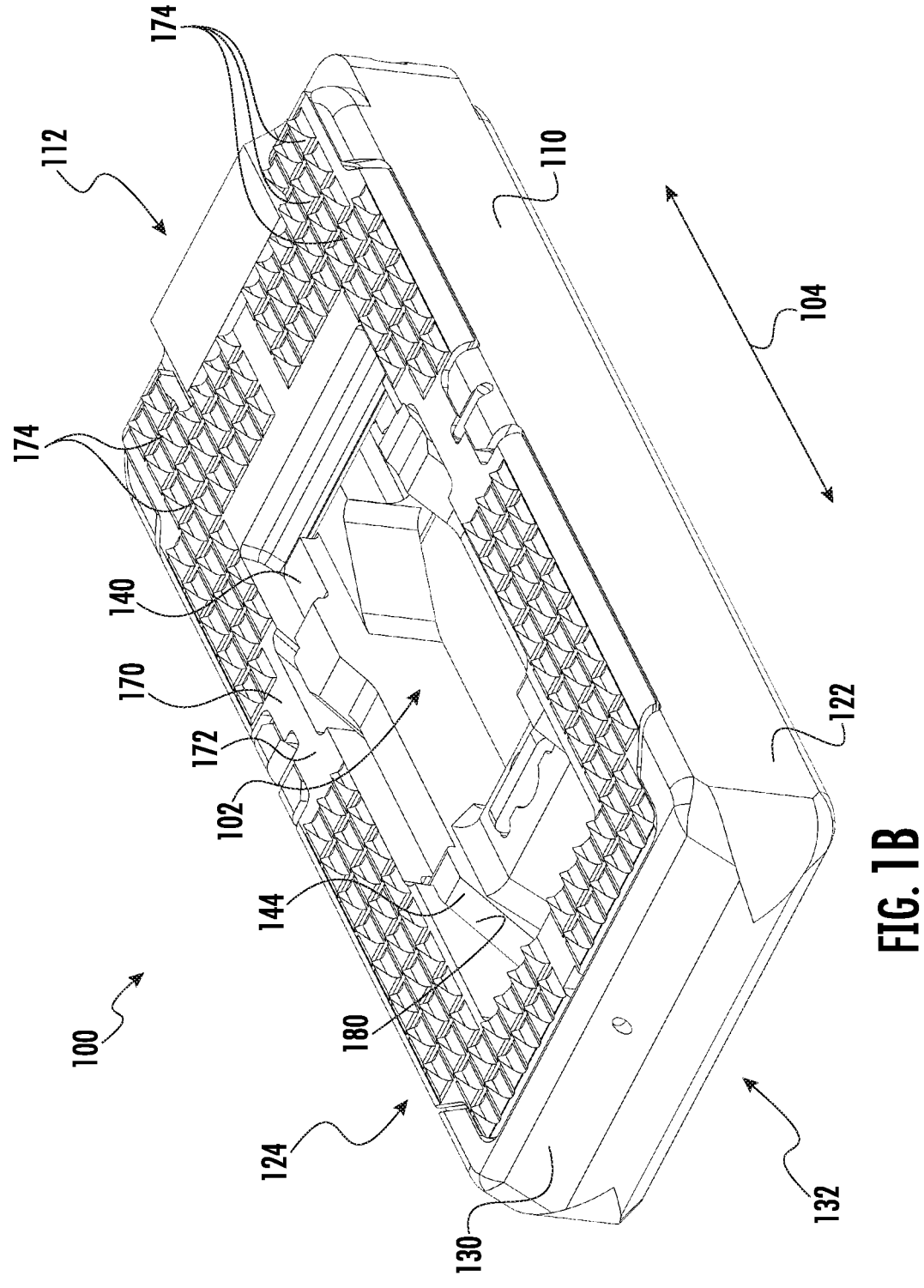
FIG. 1B is a second perspective view of the intervertebral device of FIG. 1A.

Turning to FIGS. 1A and 1B, an exemplary intervertebral device 100, which may be used with the plate assemblies described or contemplated herein, includes a base element 110, a locking element 140, and a lifting element 170. As will be understood by the description below, as with other intervertebral devices described or contemplated herein, the base element 110, the locking element 140 and the lifting element 170 cooperate to allow the intervertebral device 100 to move between a first collapsed configuration and a second expanded configuration. The base element 110 includes a proximal end 112 and a distal end 130, and a first side 122 and a second side 124. The proximal end 112 of the base element 110 may include structures to facilitate attachment to a number of different tools. For example, a delivery tool may be fixedly attached to the proximal end 112 of the base element 110 for deployment of the intervertebral device 100 between vertebral bodies, or a plate assembly may be fixedly attached to the proximal end 112 of the base element 110 for permanent attachment of the intervertebral device 100 to the surrounding vertebral bodies. For example, as shown, the proximal end 112 of the base element 110 may include one or more grooves 114, an opening 116, and one or more grooves 118 along an inner surface of the opening 116. The one or more grooves 114, 118 may be configured to accept corresponding one or more protrusions of a delivery tool or a plate assembly to selectively hold the base element 110 rigidly to the delivery tool for deployment of the intervertebral device 100 adjacent two vertebral bodies or permanently after deployment, respectively. The base element 110 may include a bottom surface 136. The bottom surface may include one or more protrusions 138 (not shown) that are adapted to interface with a biological tissue.

Once coupled to the intervertebral device 100, the delivery tool may also provide access to the locking element 140 through the opening 116 for operation of the intervertebral device 100, to raise or lower the height of the intervertebral device 100, for example. Furthermore, once the intervertebral device 100 is deployed and a void 102 is created with respect to the base element 110, the locking element 140, and the lifting element 170, one or more therapeutic agents may be directed through the delivery tool, through the opening 116, and into the void, to facilitate bone growth and healing. For example, the delivery tool may be configured to removably attach to the opening 116 of the base element 110 by deploying a protrusion in the groove 118. The base element 110 may include a blunt end 132 to encourage positioning of the intervertebral device, between adjacent vertebral bodies, for example.

The locking element 140 may be adapted to slidably couple to the base element 110 and move between the proximal end 112 and distal end 130 of the base element 110 in a direction parallel to a longitudinal axis of the base, as depicted by arrow 104. The locking element 140 may include a plurality of curvilinear surfaces 144 that may couple to corresponding curvilinear surfaces 180 of the lifting element 170. The lifting element 170 may include a top surface 172, which includes one or more protrusions 174 adapted to interface with biological tissue. Similarly, the base element 110 may include a bottom surface 136, which includes one or more protrusions 138 adapted to interface with biological tissue. The lifting element 170 may be adapted to slidably couple to the base element 110, as well as the locking element 140.

Figure 2A:
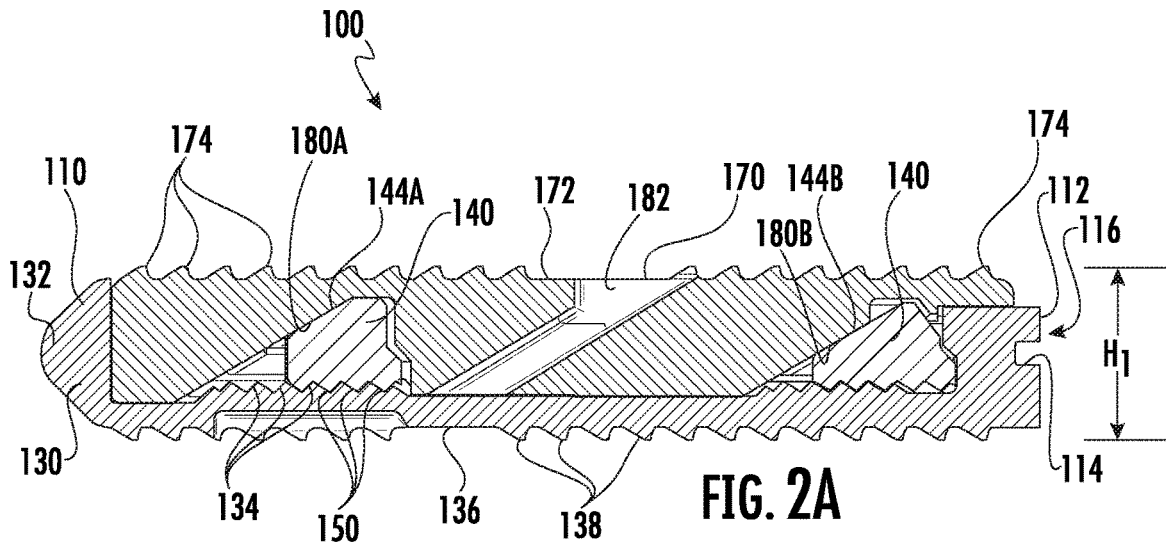
FIG. 2A is a first side section view of the intervertebral device of FIG. 1A in a collapsed configuration.
Figure 2B:
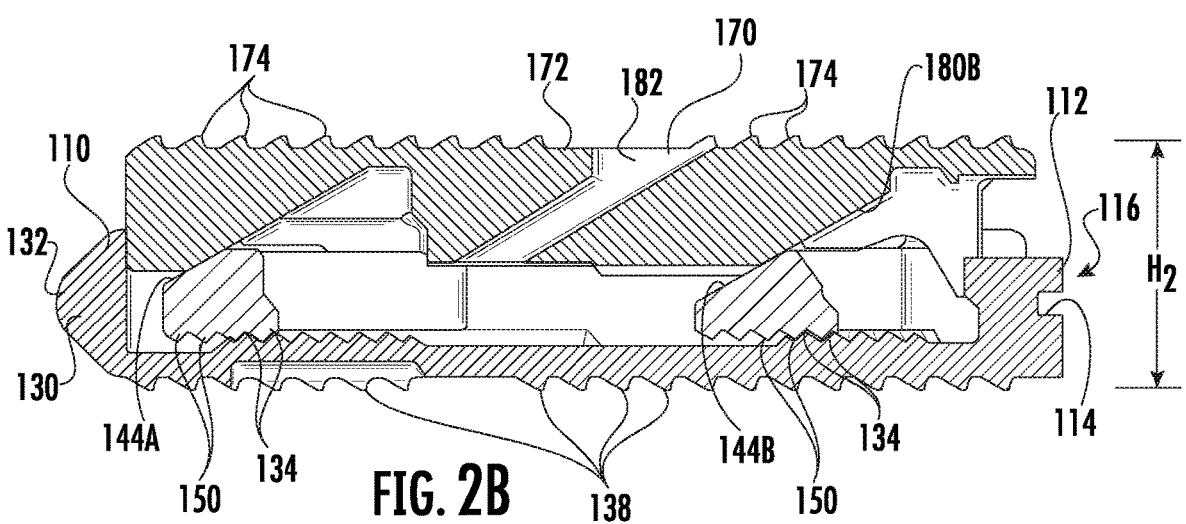
FIG. 2B is a second side section view of the intervertebral device of FIG. 1A in an expanded configuration.

Turning also to FIGS. 2A and 2B, side elevation views of the intervertebral device 100 are depicted. More specifically, FIG. 2A depicts an elevation side view of the intervertebral device 100 along the section line A-A of FIG. 1A in a first collapsed configuration, and FIG. 2B depicts an elevated side view of the intervertebral device 100 along the section line A-A of FIG. 1A in a second expanded configuration. As shown, the base element 110 extends from the proximal end 112 to the distal end 130, the distal end 130 including blunt portion 132. A delivery tool (not shown) may be interfaced to the locking element 140 to move the locking element 140 with respect to the base element 110. As the locking element 140 moves from a proximal position adjacent to proximal end 112 of the base 110, as shown in FIG. 2A, to a distal position adjacent to distal end 130 of the base 110, as shown in FIG. 2B, the locking element 140 slidably interfaces with the lifting element 170 to increase the overall height H of the intervertebral device 100. Conversely, as the locking element 140 moves from the distal position adjacent to distal end 130 of the base to the proximal end 112 of the base 110, the locking element 140 slidably interfaces with the lifting element 170 to decrease the overall height H of the intervertebral device 100. In operation, as the locking element 140 translates along a longitudinal axis of the base element 110, surfaces 144 of the locking element 140, for example surfaces 144A, 144B, slidably interface with corresponding surfaces 180 of the lifting element 170, for example surfaces 180A, 180B, to facilitate corresponding vertical movement of the lifting element 170. The lifting element 170 may include additional surfaces, such as groove 182, configured to interface with additional surfaces of the locking element 140, such as a protrusion (not shown) that may be slidably interfaced to the groove 182. The intervertebral device 100 may include a first height H1 in the first collapsed configuration of FIG. 2A and a second height H2 in the second expanding configuration of FIG. 2B. The base element 110 may also include a number of engaging elements 134 adapted to slidably interface with corresponding engaging elements 150 of the locking element 140. The engaging elements 134 of the base element 110 and the engaging element 150 of the locking element 140 are adapted to maintain the height of the intervertebral device 100 in the presence of an external compression force positioned between the top surface 172 of the lifting element 170 and the bottom surface 136 of the base element 110.

Additional details of exemplary intervertebral devices similar to intervertebral device 100 may be found disclosed or contemplated in related patent publications: U.S. Pat. No. 10,092,416, entitled "Intervertebral Devices and Related Methods," having an issue date of Oct. 9, 2018; U.S. Pat. No. 10,799,366, entitled "Intervertebral Devices and Related Methods," having an issue date of Oct. 13, 2020; and U.S. Pat. No. 11,369,483, entitled "Intervertebral Devices and Related Methods," having an issue date of Jun. 28, 2022, all of which are incorporated herein by reference in their entireties.

Figure 3:
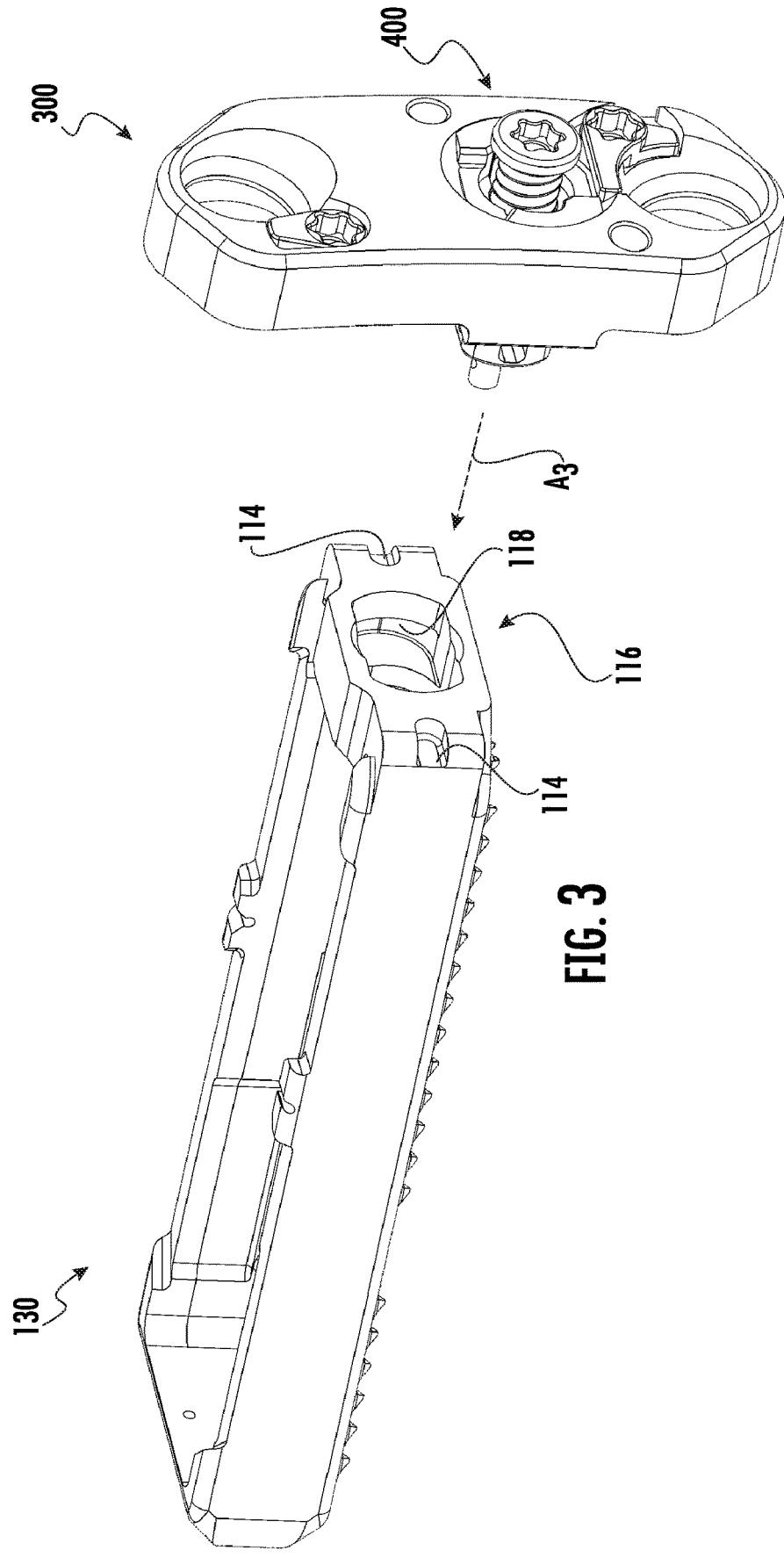
FIG. 3 is a system view of a portion of the intervertebral device of FIG. 1A and an exemplary plate assembly.

Turning to FIG. 3, a system view of a portion of the intervertebral device of FIG. 1A and a plate assembly 300 is depicted. More particularly, for simplicity, only the base 110 of the intervertebral device 100 is depicted, the base 110 including the distal opening 116 having a groove 118 on an inner surface thereof, and grooves 114. The plate assembly 300 includes a coupler 400, which provides an interface between the plate assembly 300 and the base 110 of the intervertebral device. In operation, the plate assembly 300 is moved toward and interfaces with the base 110, for example, when the base 110, as part of an intervertebral device 100, is positioned between vertebral bodies. As the plate assembly 300 is moved toward the base 110 in a direction depicted by arrow A3 a portion of the coupler 400 enters the opening 116 of the base 100 and is operated to engage a portion of the groove 118 to fixedly attach the plate assembly 300 to the base 110 of the intervertebral device 100.

Figures 4A, 4B:
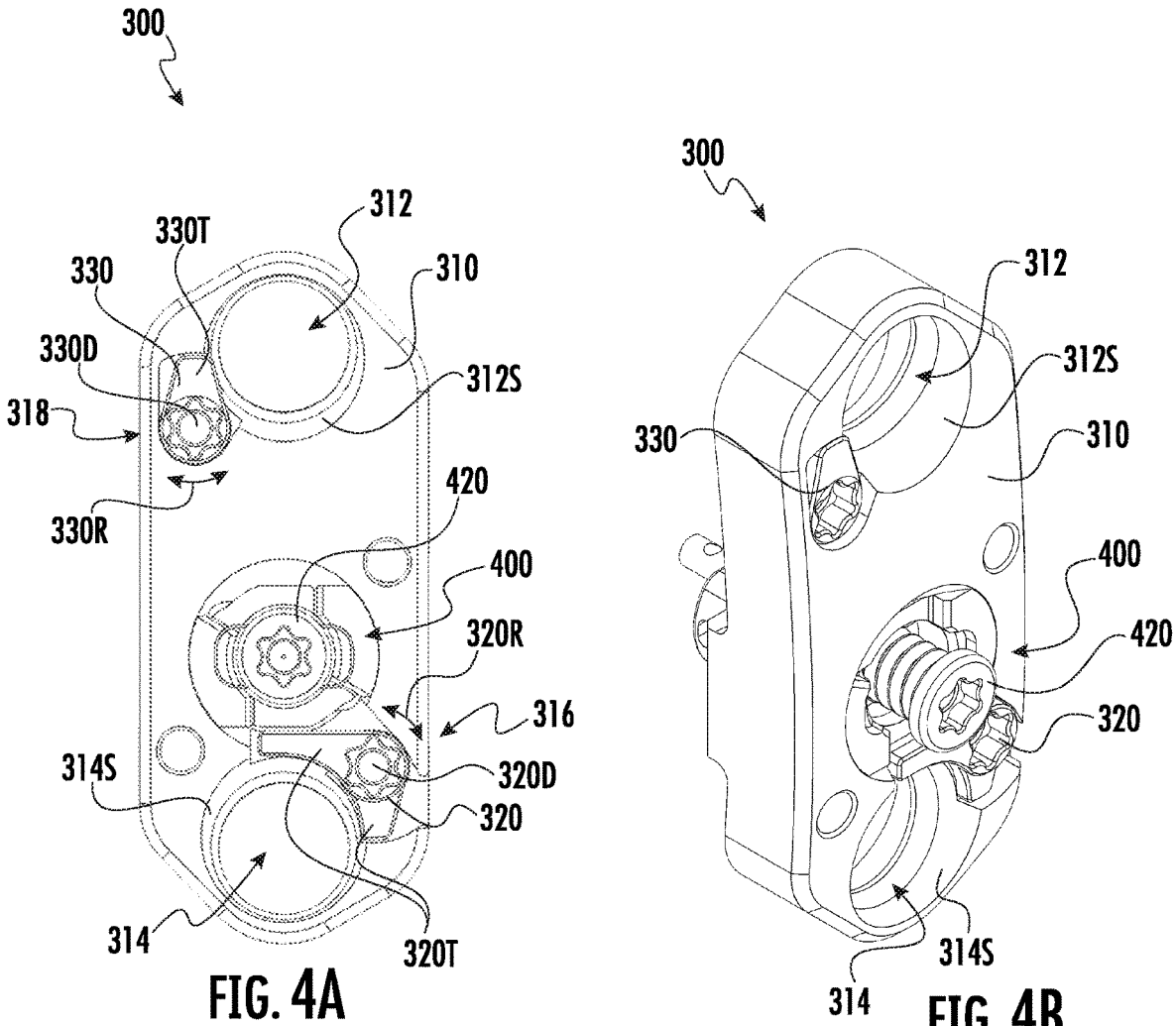
FIG. 4A is a front view of the plate assembly of FIG. 3.
FIG. 4B is a perspective view of the plate assembly of FIG. 4A.

Turning to FIGS. 4A and 4B, the plate assembly 300 may include a plate body 310 and a coupler 400, which is adapted to interface the plate assembly 300 with the intervertebral device 100. The plate body 310 may further include an opening 312 and an opening 314. Each of the openings 312, 314 are adapted to accept a vertebral body screw to fixedly attach the plate body 310 of the plate assembly 300 to adjacent vertebral bodies, as is discussed in greater detail below in reference to FIGS. 12A-12E. The openings 312, 314 may include inner surfaces 312S, 314S, respectively, having curved surfaces configured to mate with corresponding curved surfaces on the head of an associated vertebral body screw. In this way, the vertebral body screw may have a wider range of angular configurations with respect to a vertical axis of the plate body 310 of the plate assembly 300.

Plate body 310 may include an additional opening 316 adapted to receive a first tab lock 320. As discussed in greater detail below with respect to FIGS. 6A and 6B, the tab lock 320 may include one or more tab portions or tabs 320T. The tab lock 320 may be recessed in a portion of the surface of plate body 310 and may include a recessed portion 320D configured to receive a tool to facilitate rotational movement of the lock 320 with respect to the plate body 310, as depicted by arrow 320R. In this way, a vertebral body screw may be positioned through opening 314 and secured to a first vertebral body, the head of the screw adjacent a surface of plate body 310, the tab lock 320 rotated such that a tab 320T covers the head of the screw preventing the screw from backing out of the first vertebral body. As discussed in greater detail below relative to FIGS. 7A-7B, the tab lock 320 may have a lumen therethrough and once positioned within the plate body 310, the portion of the tab lock 320 opposite to the tab 320T may be swaged to secure the tab lock 320 to the plate body 310. The coupler 400 may include an elongate member 420 having a threaded portion, as is discussed in greater detail below, and once the elongate member 420 is deployed a second tab 320T of the tab lock 320 may cover the head of the elongate member 420, preventing the elongate member 420 from backing out of the coupler 400.

Plate body 310 may include an additional opening 318 adapted to receive a second tab lock 330. As discussed in greater detail below with respect to FIGS. 6A and 6B, the tab lock 330 may include tab 330T. The tab lock 330 may be recessed in a portion of the surface of plate body 310. Furthermore, the second tab lock 330 may include a recessed portion 330D configured to receive a tool to facilitate rotational movement of the lock 330 with respect to the plate body 310 as depicted by arrow 330R. In a similar manner as with tab lock 320, a vertebral body screw may be positioned through opening 312 and secured to a vertebral body, the head of the screw adjacent a surface of body 310, the tab lock 330 rotated such that a tab 330T covers the head of the screw preventing the screw from backing out of the second vertebral body. As with tab lock 320, the tab lock 330 may include a lumen therethrough, the end opposite the tab 330T being swaged to allow for rotational movement of the tab lock 330, but preventing axial movement of the tab lock 330 back out of the opening 318.

Figures 4C, 4D:
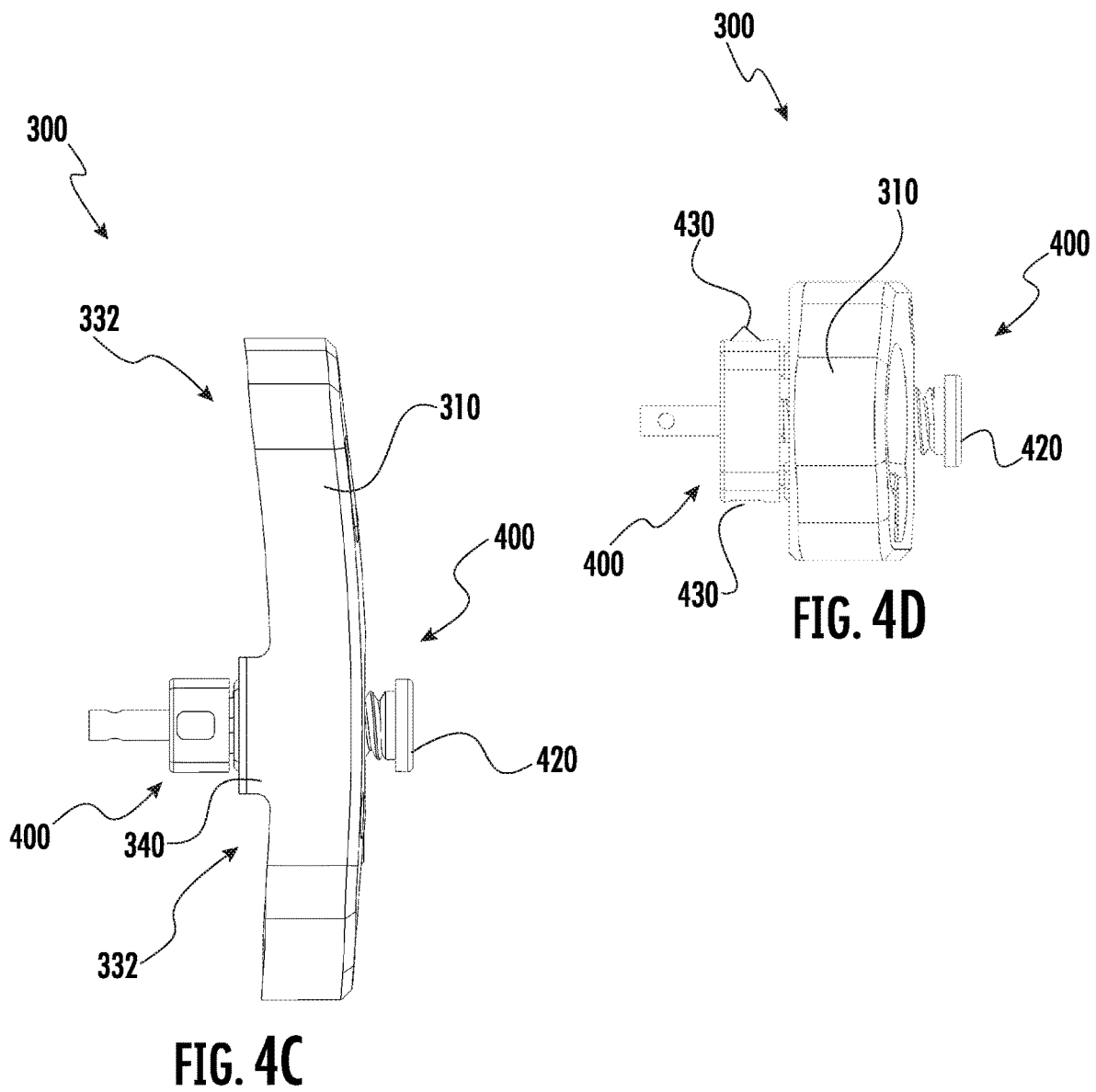
FIG. 4C is a side view of the plate assembly of FIG. 4A.
FIG. 4D is a top view of the plate assembly of FIG. 4A.

Turning also to FIG. 4C, a side elevational view of the plate assembly 300 is depicted. As shown, the plate body 310 of the plate assembly 300 may include a curved back surface 332, which may be curved to better provide a mating surface of adjacent vertebral bodies, allowing for clearance over osteophytes than may be located near the end plates of the vertebral bodies. The plate body 310 may also include a protrusion 334, which protrudes away from the back surface 332 of the plate body 310 to allow for interfacing with an intervertebral device, such as device 100, while also allowing suitable interfacing with adjacent vertebral bodies. Additionally, the plate body 310 may be selected to have a suitable width to provide a desired stiffness to help fixedly hold an intervertebral device to the adjacent vertebral bodies. Turning also to FIG. 4D, where a top view of the plate assembly 300 is depicted, the coupler 400 further including one or more protrusions 430 adapted to interface with a portion of an intervertebral device, the groove 118 of the base 110 of the intervertebral device 100, for example, to fixedly hold the plate assembly 300 to the intervertebral device 100, as discussed in greater detail below with respect to FIGS. 11A-11D.

Figure 5B:
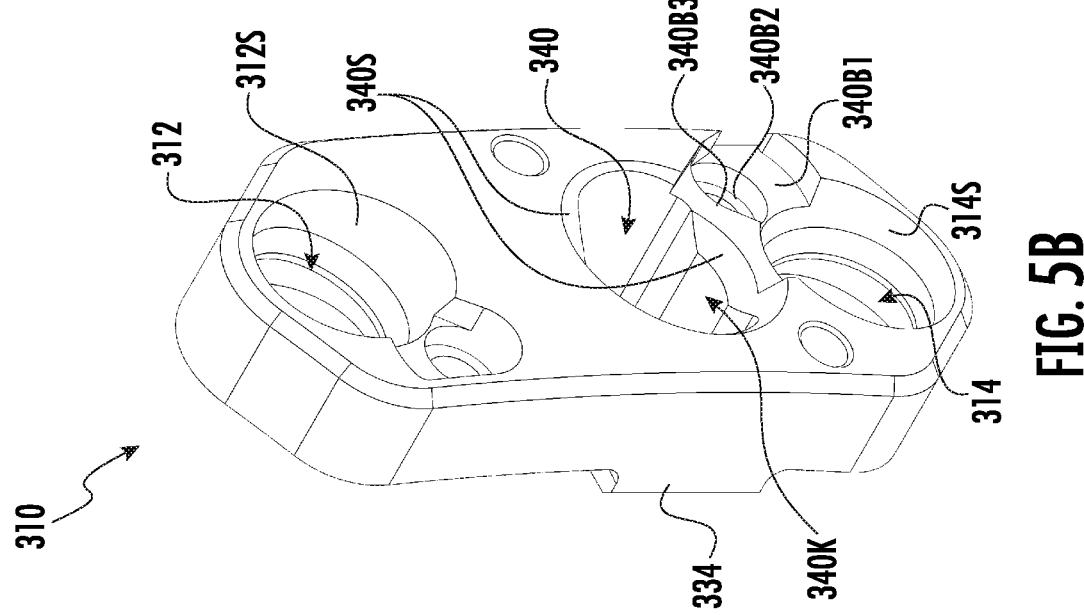
FIG. 5B is a first perspective view of the portion of the plate assembly of FIG. 5A.
Figure 5A:
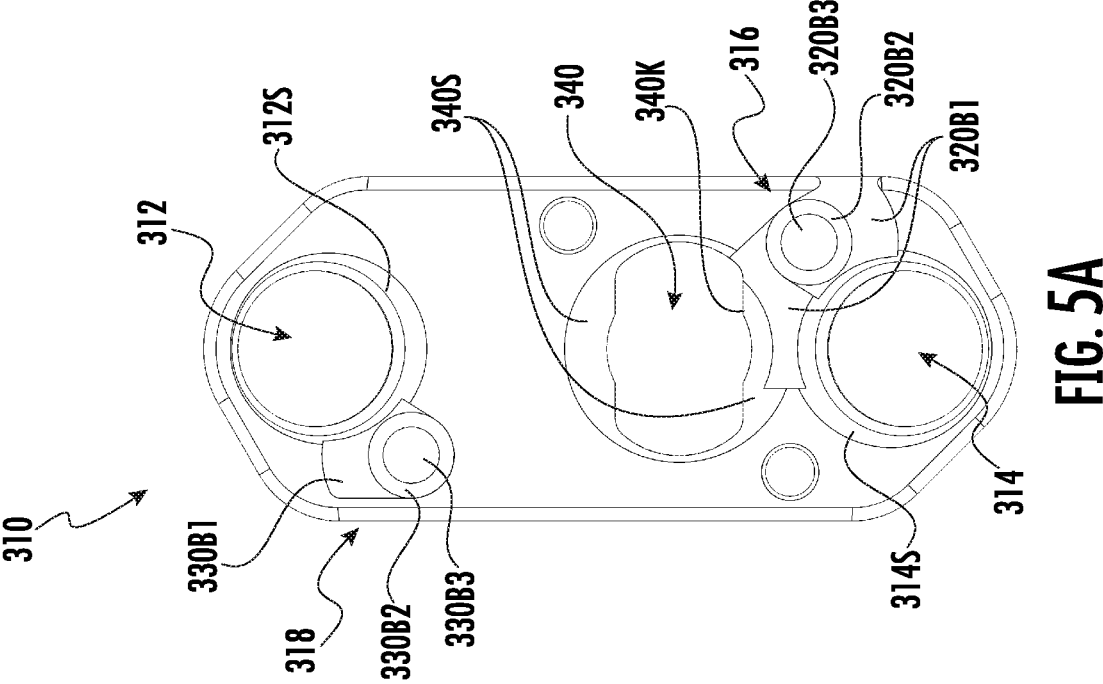
FIG. 5A is a portion of the plate assembly of FIG. 4A.
Figure 5C:
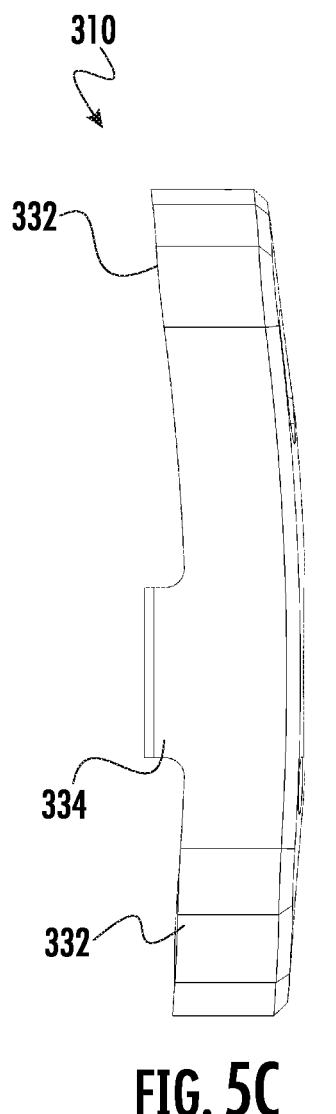
FIG. 5C is a side view of the portion of the plate assembly of FIG. 5A.
Figure 5D:
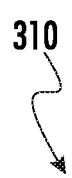
FIG. 5D is a second perspective view of the portion of the plate assembly of FIG. 5A.
Figure 5D:
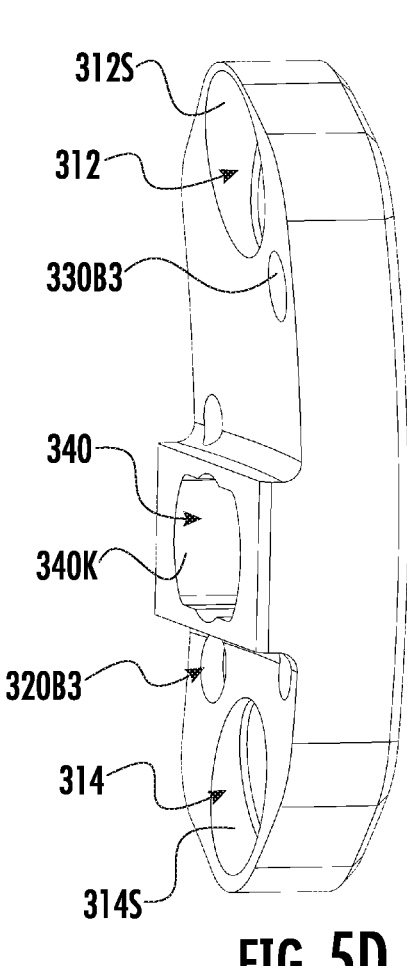

Turning to FIGS. 5A-5D, only the plate body 310 is depicted highlighting features of various openings and surfaces of the plate body 310. Plate body 310 may include an opening 340 configured to receive the coupler 400. As shown, the opening 340 may include a keyed surface 340K to provide a rectangular shape to minimize rotational movement of the coupler 400 in the face of rotational or linear forces applied to the elongate member 420 during operation. Opening 340 may further include a one or more curvilinear surfaces 340S configured to receive a portion of the coupler 400 to allow the coupler 400 to be positioned recessed within at least a portion of opening 340, for example. The one or more curvilinear surfaces 340S may also allow the coupler 400 to couple to the plate body 310 in a number of different axial orientations. For example, once the coupler 400 is positioned within at least a portion of opening 340, a longitudinal axis of the coupler 400 may be non-parallel to a longitudinal axis of opening 340 allowing for case of coupling between the plate assembly 300 and an intervertebral device during operation. Recessed opening 316 may be provided in the plate body 310 and may be adapted to receive the first tab lock 320 therein. The recessed opening 316 may include a first recess 320B1, a second recess 320B2, and a third recess 320B3. Recess 320B1 may be adapted to allow the one or more tabs 320T of the tab lock 320 to rotationally move substantially flush with an adjacent surface of the plate body 310. Recess 320B2 and recess 320B3 may be provided to provide additional stability for the rotational movement of the tab lock 320. Recess 320B3 may proceed through the back of the plate body 310, as shown in FIG. 5D. In similar fashion, a recessed opening 318 may be provided in the plate body 310 adapted to receive the second tab lock 330 therein. The recessed opening 318 may include a first recess 330B1, a second recess 330B2, and a third recess 330B3. Recess 330B1 may be adapted to allow the one or more tabs 320T to rotationally move substantially flush with an adjacent surface of the plate body 310. Recess 330B2 and recess 330B3 may be provided for additional stability during rotational movement of the tab lock 330. Recess 330B3 may proceed through the back of the plate body 310, as shown in FIG. 5D. The protrusion 340 may include one or more additional protrusions (not shown), each of the one or more protrusions adapted to interface with a portion of an intervertebral device, for example, a respective one of the grooves 114 of the base 110 of the intervertebral device 100, to provide additional support and reduce mobility of the plate assembly 300 with respect to the intervertebral device when attached thereto, if desired.

Turning to FIGS. 6A and 6B, the tab portion 330T of tab lock 330 includes a bottom surface 334 configured to rotationally reside in recessed portion 330B1, as best depicted in FIG. 5B. The tab lock 330 may include a first cylindrical portion 336 configured to rotationally reside in the recessed portion 330B2 and a second cylindrical portion 338 configured to rotationally reside in the recessed portion 330B3, as best depicted in FIG. 5B. Additionally, recessed portion 330D of the tab lock 330 may extend through the plate body 310 to form a lumen 330L. As mentioned above, the recessed portion 330D may include a pattern configured to receive a tool to facilitate rotational movement of the tab lock 330. The pattern may be extended the entire length of the lumen 330L or any length thereof, as long as the tool can facilitate rotational movement of the lock 330 with respect to plate body 310 of the plate assembly 300.

Turning now to FIGS. 7A and 7B, the tab portion 320T of tab lock 320 may include a bottom surface 324 configured to rotationally reside in an associated recessed portion 320B1, as best depicted in FIG. 5B. For example, a bottom surface 324A of a first tab 320TA may rotationally reside in a first recessed portion 320B1A, and a bottom surface 324B of a second tab 320TB may rotationally reside in a second recessed portion 320B1B. The tab lock 320 may further include a first cylindrical portion 326 configured to rotationally reside in a recessed portion 320B2 and a second cylindrical portion 328 configured to rotationally reside in a recessed portion 320B3, as best depicted in FIG. 5B. Additionally, similar to tab lock 330, recessed portion 320D of the tab lock 320 may extend through the plate body 310 to form a lumen 320L. As mentioned above, the recessed portion 320D may include a pattern configured to receive a tool to facilitate rotational movement of the tab lock 320. The pattern may be extended the entire length of the lumen 320L or any length thereof, as long as the tool can facilitate rotational movement of the lock 320.

Tab locks 320, 330 may be retained in rotational position through any suitable means. For example, tab locks 320, 330 may be constructed to form fit within the corresponding recesses 320B, 330B within the plate body 310. Such friction fitment may be suitable to retain the tab lock 320, 330 in position in light of preserved forces on the surfaces 324, 334 of the tab portions 320T, 330T. Alternatively, tab locks 320, 330 may include threaded portions, formed on the outside of cylindrical portion 328, 338 configured to mate with corresponding threaded portions formed in corresponding recessed portion 320B3, 330B3, the threaded portions maintaining the tab locks 320, 330 in rotational position. Alternatively, the first recessed portion 320B1, 330B1 may include a circumferential groove adapted to receive a retaining ring therein, the retaining ring acting to retain the tab locks in rotational position. Alternatively, the back end of each lumen 320L, 330L, opposite of the associated tab 320T, 330T, for example, may be swaged to increase the diameter of the lumen 320L, 330L adjacent to the plate body 310, allowing rotational movement while preventing axial movement of the tab lock 330T.

Figure 8:
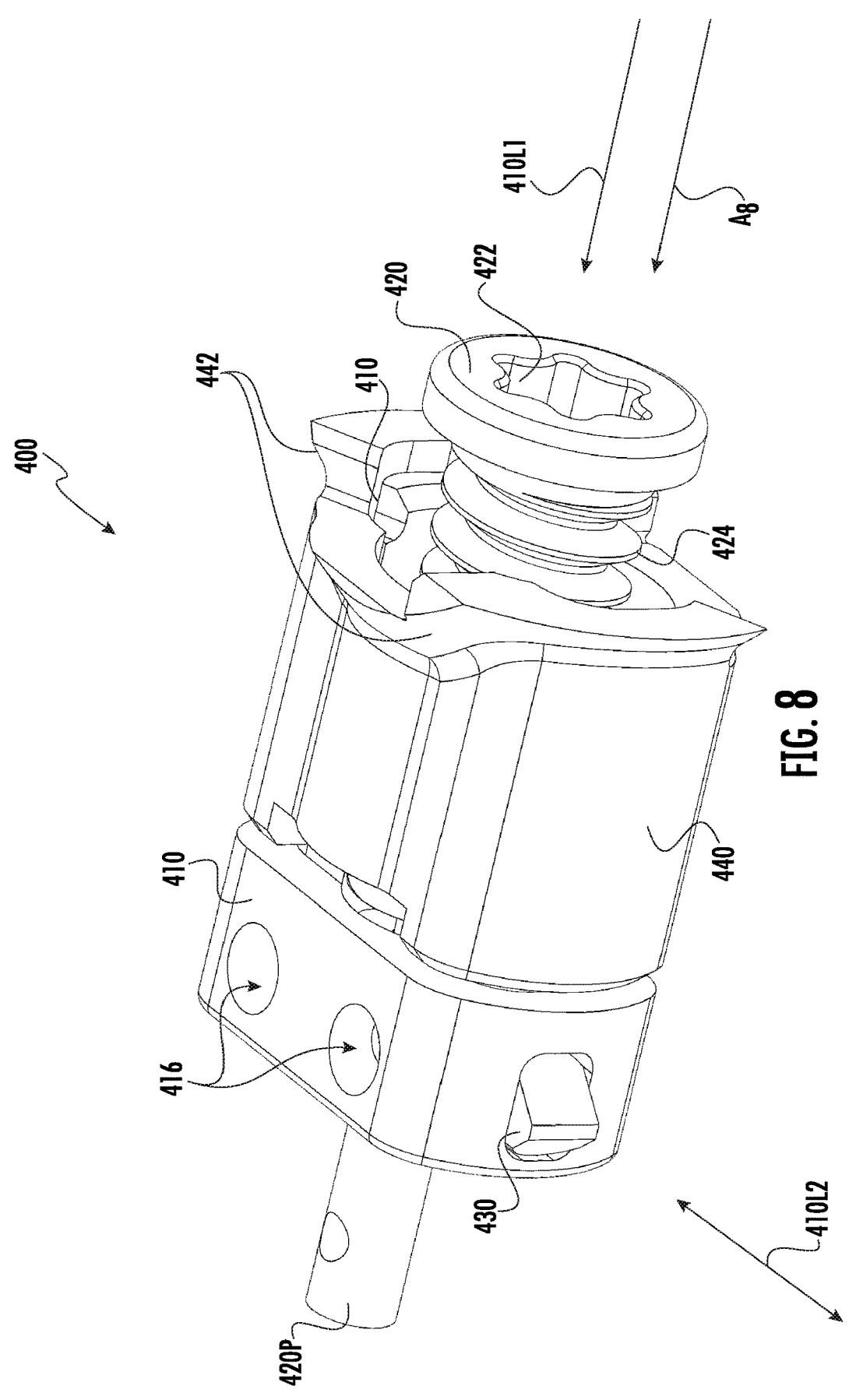
FIG. 8 is a perspective view of an exemplary coupler, as part of the plate assembly of FIG. 4A.

With reference to FIG. 8, generally, coupler 400 may include an inner housing 410, an elongate member 420, one or more protrusions 430 and an outer housing 440. The inner housing 410 includes a lumen 410L1 therethrough, the elongate member 420 adapted to translate through the lumen 410L1 of the inner housing 410, ending in a distal portion 420D. A distal portion 410D of the inner housing 410 may include a second lumen 410L2, which is substantially perpendicular to the first lumen 410L1, the one or more protrusions 430 being adapted to translate within the second lumen 410L2. Elongate member 420 may include a threaded portion 424 that rotationally interfaces with a corresponding threaded portion of inner housing 410, as described in greater detail below with reference to FIGS. 11A-11D, to allow for rotational translation through first lumen 410L1. In certain embodiments, the elongate member 420 may be adapted to translate linearly through at least a portion of the lumen 410L1 and translate rotationally through another portion of the lumen 410L1. In operation, the elongate member 420 is adapted to translate through the inner housing lumen 410L1 in a direction as depicted by arrow A8, the elongate member 420 including surface transitions along its length resulting in the one or more protrusions 430 to radially move away from the elongate member 420 and exit an opening in the distal end 410D of the inner housing 410, as generally depicted. Protrusions 430 may then be utilized to fixedly attach the plate assembly 300 to an intervertebral device, such as device 100. The inner housing 410 may also include additional openings 416 adapted to retain protrusions 430 within the inner housing 430, as described in greater detail with respect to FIGS. 11A-11D.

With reference to FIGS. 9A-9E, an exemplary protrusion 430 is described in greater detail. Protrusion 430 is positioned within the second lumen 410L2 of the housing 410 of coupler 400 and may protrude from an opening in the housing 410 during operation of the coupler 400. As shown, the protrusion 430 may include a first side surface 430C1, a second side surface 430C2, a third side surface 430C3, a fourth side surface 430C4, a bottom surface 430B, and a top surface 430T. Top surface 430T may further include inter- ference surfaces that interfere with portions of an interver- tebral device during use to encourage coupling with the intervertebral device or retraction of the protrusion 420 back within the housing 410 of coupler 400, when the plate assembly 300 is detached from the intervertebral device, for example. More specifically, the top surface 430T may fur- ther include a flat top surface 434 formed by the relative separation of a first sloped surface 436A and a second sloped surface 436B. The protrusion 430 may be formed from round stock, from which material may be removed to form side surface 430C2 and side surface 430C4. Removing such material results in the formation of tabs 438, which may be utilized in maintaining a desired orientation of the protrusion 430 with respect to the housing 410 as the protrusion translates along the lumen 410L2 of the housing 410. Last, another interference surface 432 may be formed adjacent to the bottom surface 430B, the surface 432 adapted to inter- fere with a portion of the elongate member 420 to encourage movement of the protrusion 430 away from central lumen 410L1 during operation.

Figures 10A, 10B:
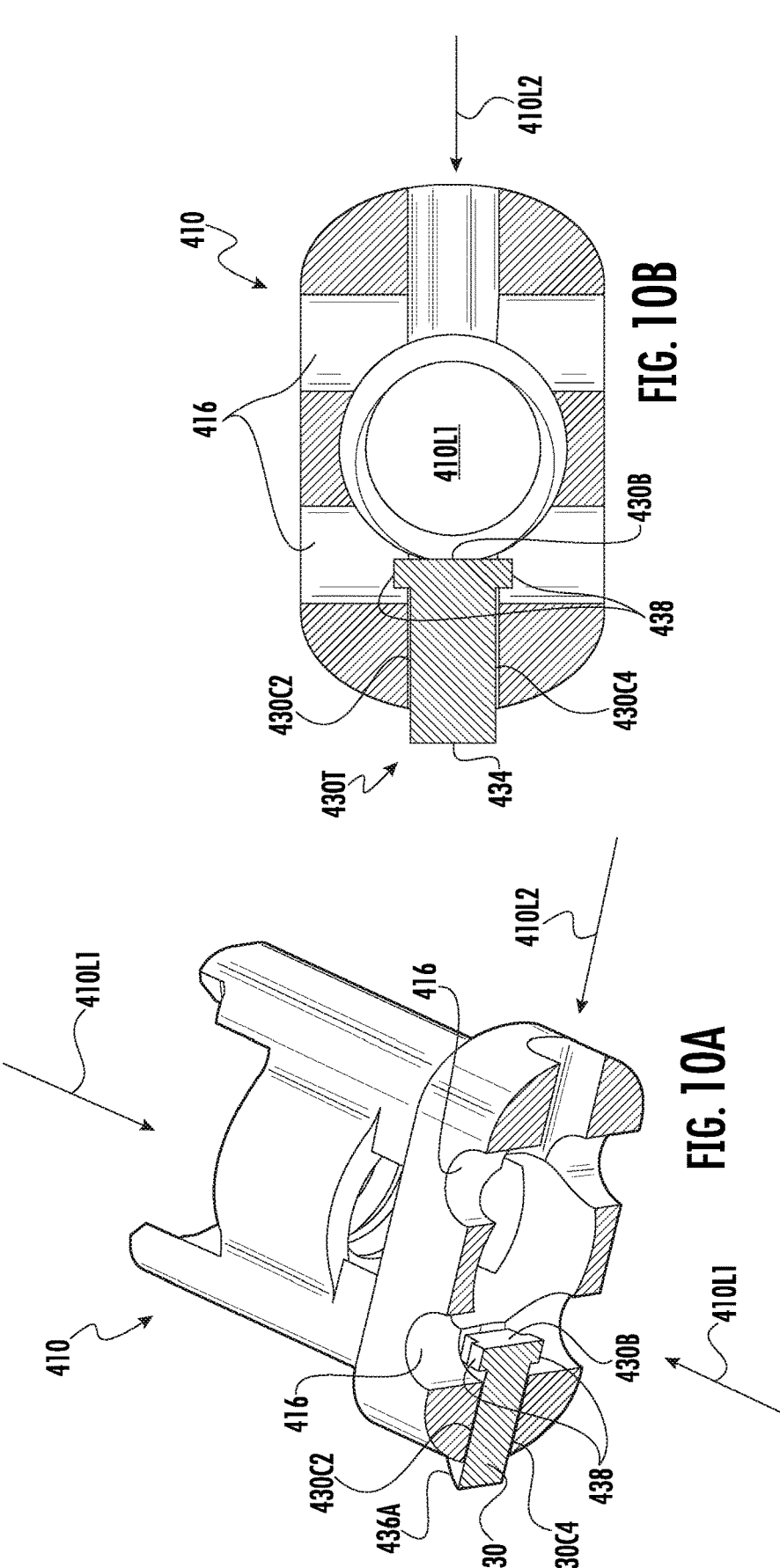
FIG. 10A is a perspective section view of a portion of the exemplary coupler of FIG. 8.
FIG. 10B is a bottom view of the section view of FIG. 10A.

Turning also to FIGS. 10A and 10B, operation of the tabs 438 of protrusions 430 relative to the housing 410 of the coupler 400 will be described in greater detail, the remaining portions of the coupler 400 removed for clarity. During fabrication, a protrusion 430 may be inserted into the first lumen 410L1 and further into a portion of the second lumen 410L2, as depicted. The second lumen 410L2 may include mating flat surfaces, each interfacing with one of the side surfaces 430C2, 430C4 to maintain proper longitudinal orientation of the protrusion 430 as it translates along the second lumen 410L2. The distal portion of the housing 410D includes openings 416. The tabs 438 of the protrusion 430 interfere with the openings 416 of the housing 410, limiting the radial movement of the protrusion 430 away from the first lumen 401L1.

Figure 11A:
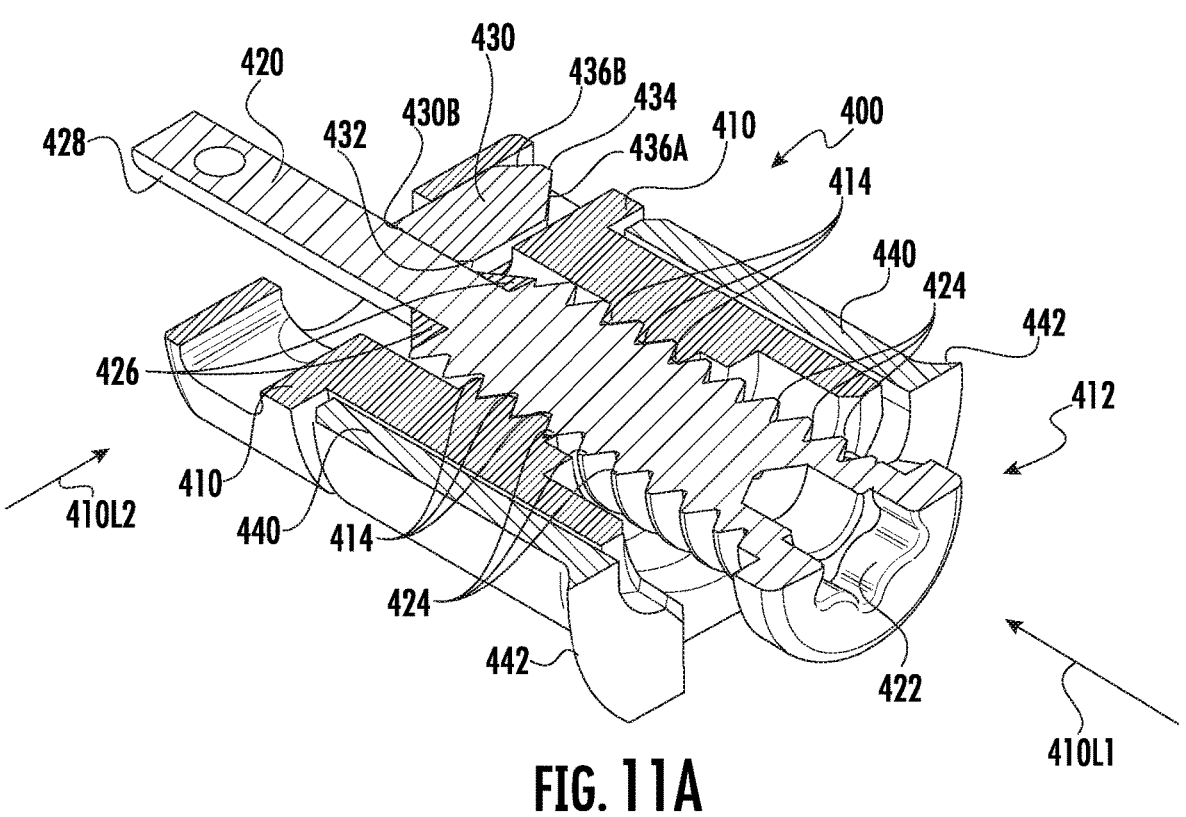
FIG. 11A is a perspective section view of the exemplary coupler of FIG. 8 in an operative configuration.

With reference to FIGS. 11A-11D, the coupler 400 opera- tion will be described in greater detail. Turning specifically to FIG. 11A and as a quick reminder, the coupler 400 includes housing 410, elongate member 420, one or more protrusions 430, and a plate cap 440. The housing 410, along with the plate cap 440, may include a keyed shape similar to the keyed shape 340k of opening 340 to help maintain their relative rotational position during use. The housing 410 may include first lumen 410L1 extending therethrough along a longitudinal axis of the housing 410, and second lumen 410L2 extending therethrough along an axis perpendicular to the longitudinal axis of the housing 410. Lumen 410L1 of the housing 410 may include a threaded portion 414 con- figured to couple to a portion of the elongate member 420. A first protrusion 430 may be positioned in a first radial portion of the second lumen 410L2, as shown. As described above, protrusion 430 may include several interface sur- faces, each which may interact with adjacent structures during operation. In particular, the interference surface 432 may be configured to interfere with a portion of the elongate member 420, as described in greater detail below. Further- more, sloped surface 436A may be configured to interfere with a portion of an intervertebral device, the groove 118 of the base 110 of intervertebral device 100, for example. While only one protrusion 430 is depicted for simplicity of discussion, another protrusion 430 may be positioned in a second radial portion of the second lumen 410L2 opposite to the first radial position, and positioned in a similar manner where end 434 points away from central lumen 410L1. Furthermore, it should be understood that additional protru- sions 430 may be positioned within additional lumens 410L of the housing 410, if desired.

As shown, the elongate member 420 may include a recessed portion 422 adapted to receive a tool for rotational movement thereof. Elongate member 420 may also include a threaded portion 424 adapted to interface with the threaded portion 414 of the housing 410 to allow for movement of the elongate member 420 with respect to the housing 410 through lumen 410L1 during rotation of the elongate mem- ber 420. The elongate member 420 may further include a transition portion 426 distal to the threaded portion 424, the transition portion 426 being a conical surface about the elongate member 420, the conical surface adapted to inter- fere with the surface 432 of protrusion 430, resulting in axial movement of the protrusion 430 away from central lumen 410L, as described in greater detail below. Distal to the transition portion 426, the elongate member may have a cylindrical shape 428 having a diameter less than a diameter of threaded portion 424 of the elongate member 420, for example. Coupler 400 may further include plate cap 440 adapted to be slidably coupled to housing 410. The plate cap 440 may include a lip portion 442 adapted to slidably couple with one or more surfaces of the plate body 310, such as surfaces 340S of opening 340. The coupling between lip portion 442 of the coupler 400 and surfaces 340S of the plate allow for a longitudinal axis of the elongate coupler 420 to be nonparallel to a longitudinal axis of opening 340 of the plate 310, which may allow for easier mating with an intervertebral device during operation. Since the plate cap 440 is slidably disposed about the housing 410, the combi- nation of the plate cap 440 and the housing 410 may accommodate body 310 elements of differing widths, each providing a corresponding different stiffness. The plate cap 440, along with the plate 300, may be retained relative to an intervertebral device by the elongate member 420.

Figure 11B:
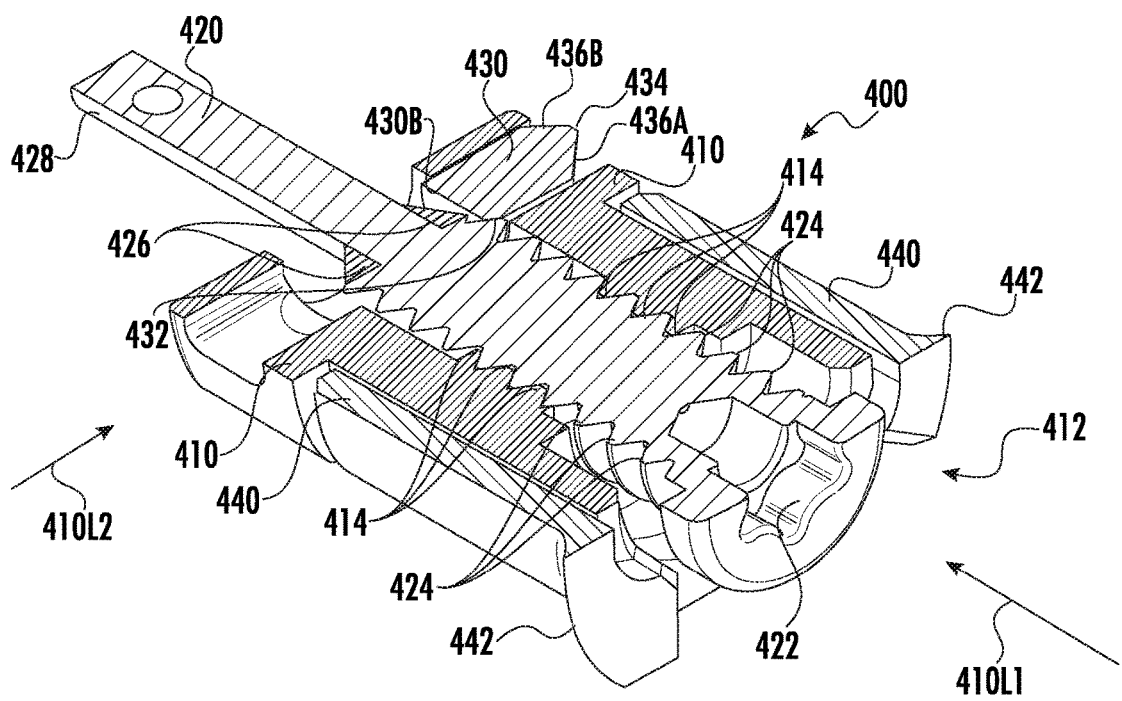
FIG. 11B is a perspective section view of the exemplary coupler of FIG. 8 in another operative configuration.
Figure 11C:
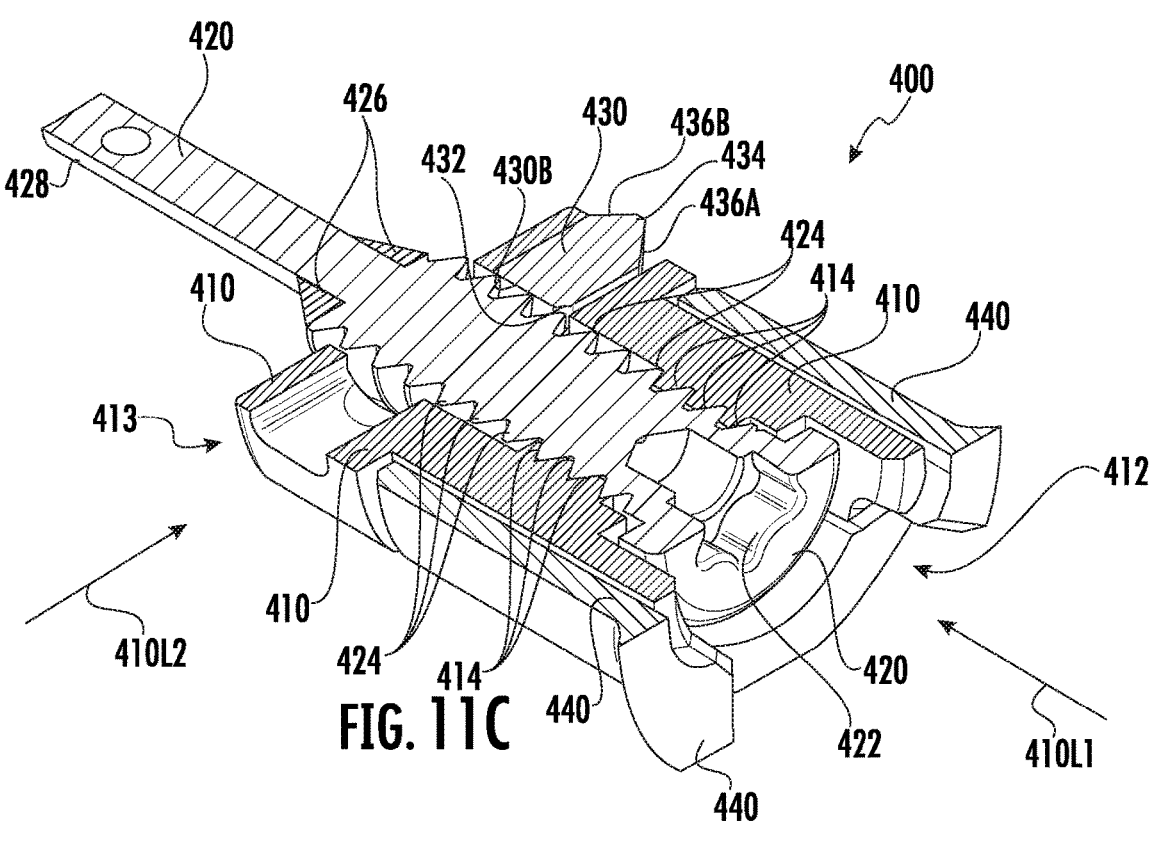
FIG. 11C is a perspective section view of the exemplary coupler of FIG. 8 in yet another operative configuration.

In operation, as depicted in FIG. 11A, elongate member 420 is in a retracted position within lumen 410L1 such that the bottom surface 430B of the protrusion 430 is free to move in the lumen 410L2 and rest against the surface 428 of the elongate member 420. As the elongate member 420 is rotated in a first direction, the member 420 may translate further into lumen 410L1, and the sloped surface 432 of the protrusion 430 may interfere with the transition portion 426 of the elongate member 420. Turning to FIG. 11B, as the elongate member 420 is rotatably operated to move distally in the lumen 410L1, the transition portion 426 of the elongate member 420 engages the sloped surface 432 of the bottom surface 430B of the protrusion 430. In response, the protrusion 430 moves radially in a direction away from the first lumen 410L1. With reference also to FIG. 11C, as the elongate member 420 is further rotationally operated the bottom surface 430B of the protrusion 430 travels further along the transition portion 426 and on top of the threaded portion 424 of the elongate member 420. When the bottom surface 430B of the protrusion 430 is engaging the threaded portion 424 of the elongate member 420, distal surface 434 of the protrusion 430 extends out the radial opening of the lumen 410L2, as depicted.

Figure 11D:
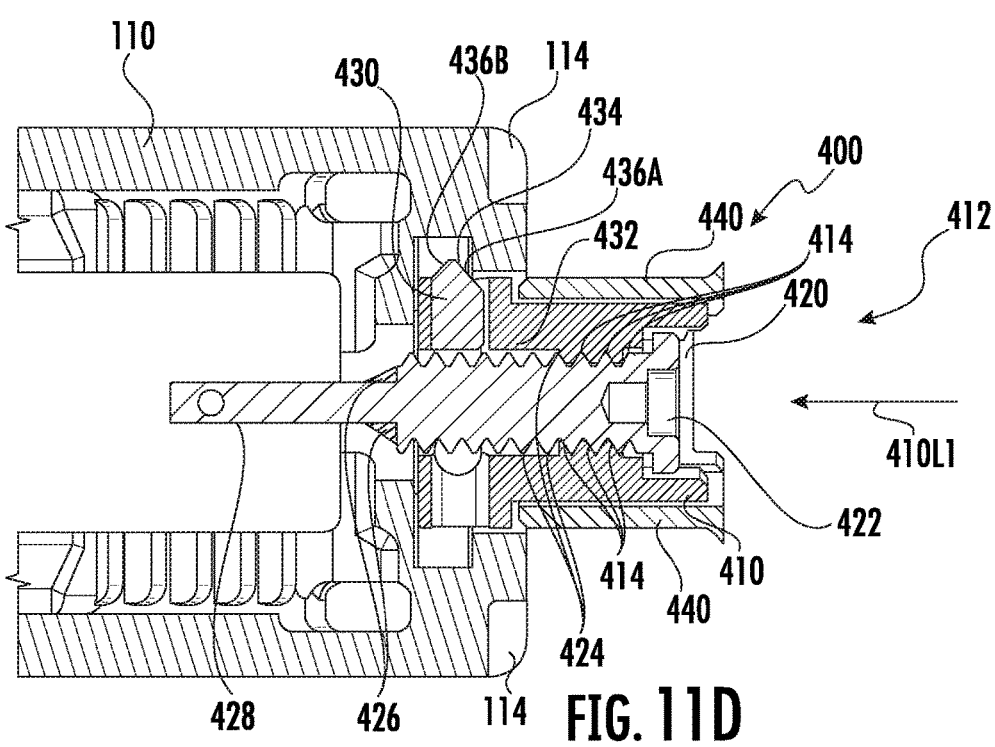
FIG. 11D is a top section view of the exemplary coupler of FIG. 8 coupled to a portion of the intervertebral device of FIG. 1A.

Referring also to FIG. 11D, a section view of the coupler 400 and the base 110 of the intervertebral device 100 is depicted. For clarity purposes only, the remaining portions of the intervertebral device 100, as well as the remaining elements of the plate 300 are not shown. When the elongate member 420 fully engages the housing within the lumen 410L1, the bottom surface 432 of the protrusion 430 rides on top of the threaded portion 424 of the elongate portion 420. In this configuration, the tip 434 of the foot enters the groove 118 of the base 110 and the sloped surface 436A of the protrusion 430 interferes with a side surface of the groove 118, as depicted, effectively fixedly connecting the plate 300 to the intervertebral device 100. Once the elongate member 420 is fully engaged the plate 300 is fixedly coupled to the intervertebral device 100. A vertebral body screw may be placed in each of the openings 312, 314, respectively, of the plate 310, and screwed into place to fixedly hold the plate to adjacent vertebral bodies. If desired, the vertebral body screws may be positioned to fixedly couple the plate 300 to the adjacent vertebral bodies prior to fixedly coupling the plate 300 to the intervertebral body 100, although alignment of the plate assembly 300 to the intervertebral body 100 may prove to be challenging.

If the elongate member 420 is rotatably operated in a second direction, the elongate member 420 may move proximally. Once the transition portion 426 of the elongate member 420 is located proximal to the second lumen 410L2, further interference between the sloped surface 436A of the protrusion 430 and the groove 118 of the base element 110 results in the axial movement of the protrusion 430 toward the first lumen 410L1, and detachment of the plate assembly 300 from the intervertebral device 100. Such independent movement of the protrusion 430 with respect to the remaining portions of the coupler 400 results in less complicated and more reliable method to retain a plate assembly to an intervertebral device. As should be readily understood, as the protrusion 430 independently moves with respect to remaining portions of the coupler 400, with the elongate member retracted and the protrusion tip 434 exiting the second lumen 410L2, the sloped surface 436B may interfere with the opening of the intervertebral device resulting in the protrusion 430 moving radially toward the first lumen 410L1, the bottom surface 430B of the protrusion 430 abutting the distal portion 428 of the elongate member 420, for example.

Figure 12A:
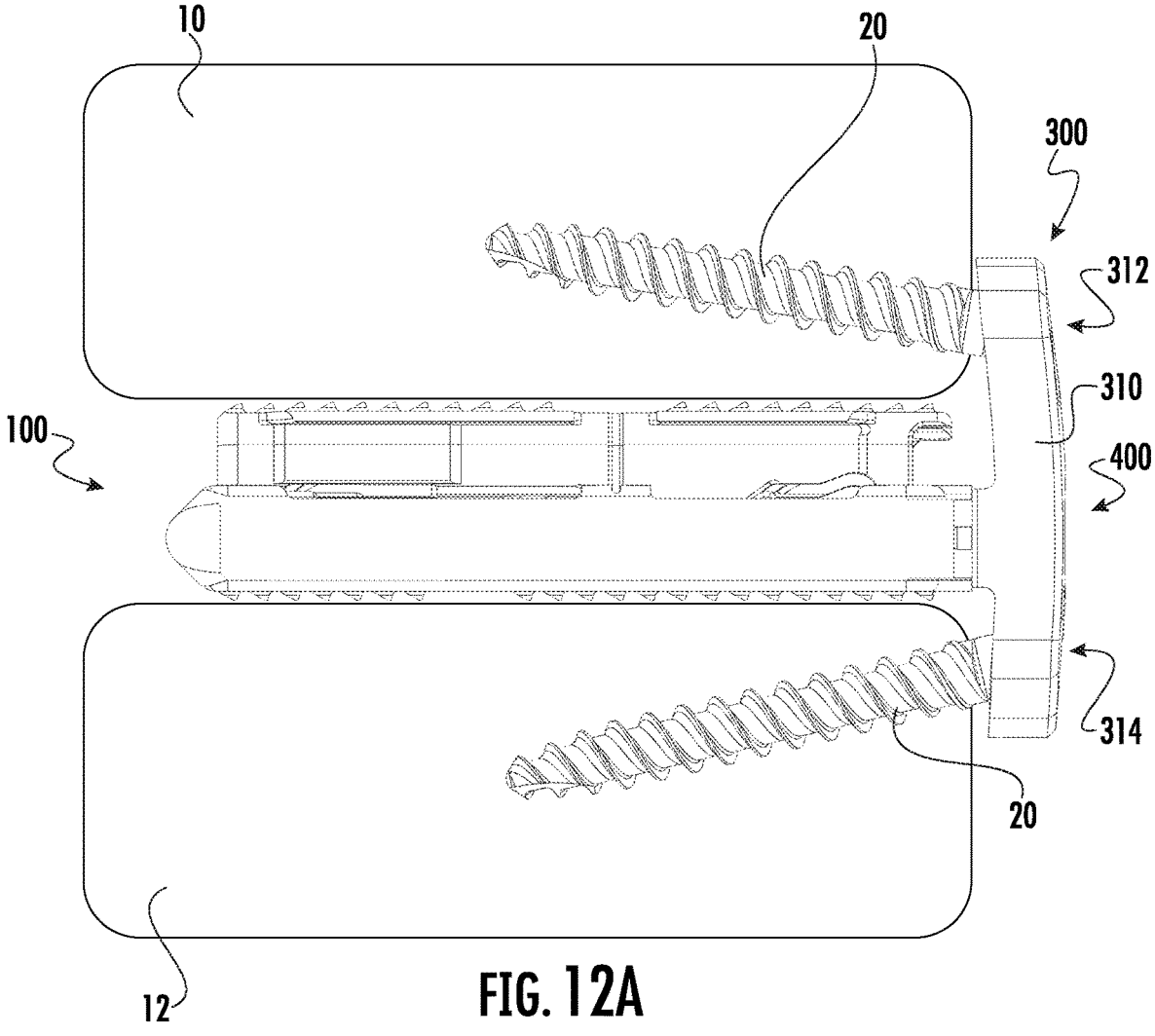
FIG. 12A is a symbolic side view of the plate assembly of FIG. 4A coupled to both, the intervertebral device of FIG. 1A and adjacent vertebral bodies.
Figure 12E:
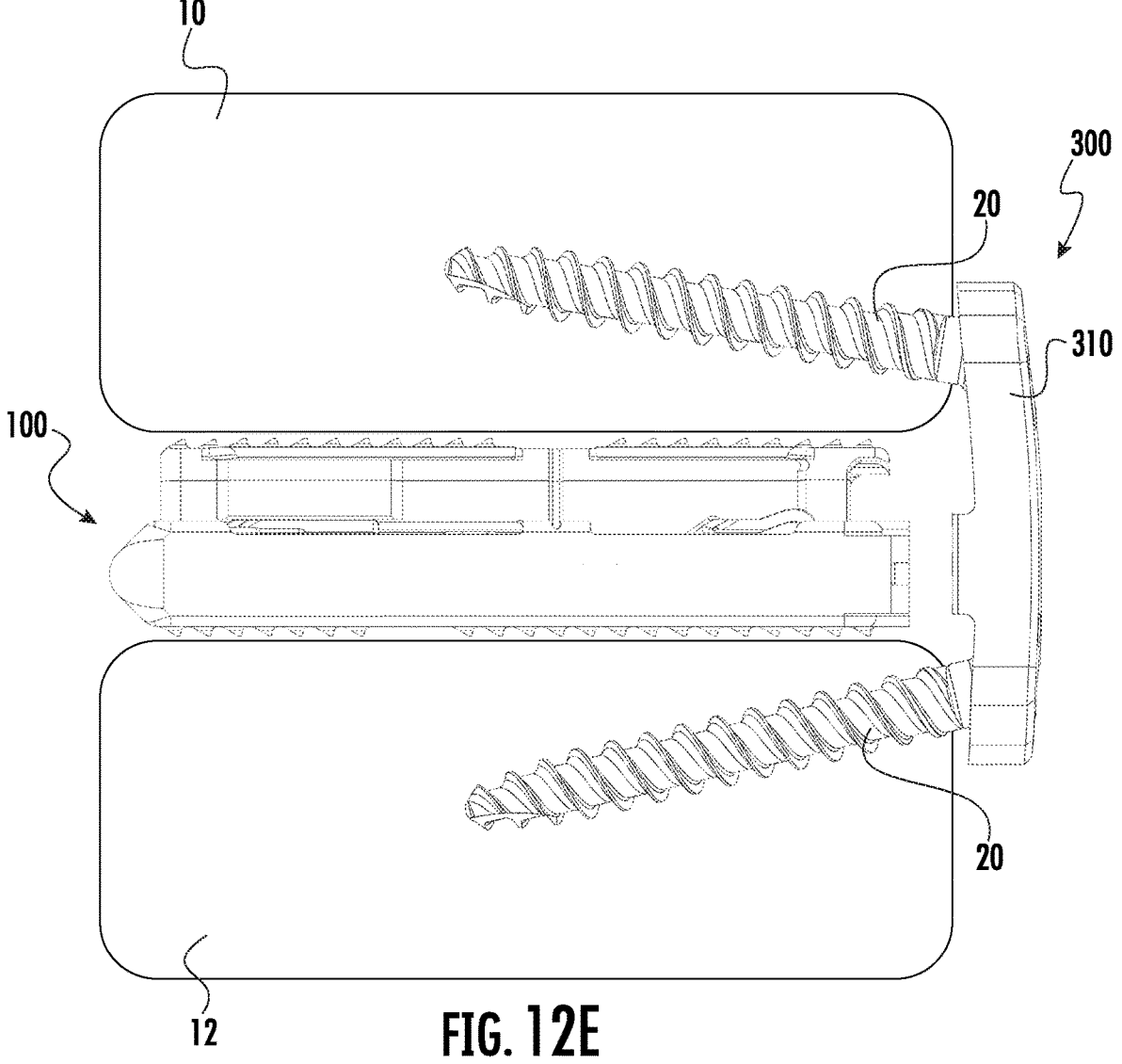
FIG. 12E is a side view of the plate assembly of FIG. 4A and the intervertebral device of FIG. 1A, each independently coupled to adjacent vertebral bodies.

Turning to FIGS. 12A-12E, exemplary positioning of the plate assembly 300 relative to an interventional device and adjacent vertebral bodies is described. The depictions of FIGS. 12A, 12B, and 12E are for illustrative purposes only and, therefore, are not necessarily to scale. FIG. 12A depicts an exemplary placement of an intervertebral device, such as intervertebral device 100, in an expanded configuration between a first vertebral body 10 and a second vertebral body 12. Once positioned, the plate assembly 300 may then be position adjacent to and coupled with the intervertebral device 100, as described with respect to FIG. 11D above. Once the plate assembly 300 is coupled to the intervertebral device 100, the plate assembly 300 may be fixedly attached to the adjacent vertebral bodies through the use of one or more vertebral body screws, individually referred to as a vertebral body screw 20. For example, a first vertebral body screw 20 may be advanced through opening 312 of the plate 310 and into the first vertebral body 10, and a second vertebral body screw 20 may be advanced through opening 314 of the plate 310, as generally depicted. Turning to FIG. 12B, an end view of a plate assembly 300 coupled to the intervertebral device 100 and adjacent vertebral bodies 10, 12 is depicted. As shown, once the vertebral body screws 20 are positioned, the tab locks 320, 330 may be rotationally operated to position tab portions 320T, 330T over corresponding heads of vertebral body screws 20, as well as elongate member 420 of coupler 400, preventing the screws and elongate member 320 from backing out of their position.

FIGS. 12C and 12D depict details of a typical vertebral body screw 20 that may be utilized with the plate assembly 300. vertebral body screw 20 may include a distal end 22, a threaded portion 20T, a neck portion 20N and a head 24. The distal end 22 of the vertebral body screw 20 may be adapted to self-tap into a vertebral body upon application of rotational movement of the screw 20. The head 24 may include a recessed area 26 having a patterned surface matching a tool for rotation of the vertebral body screw 20. The recessed area may also include a threaded portion 26T to allow attachment of an extension (not shown) to maintain control over the screw until positioned, positioned adjacent to the plate assembly 300 for example. Increasing the recessed area 26 of the head 24 of the vertebral body screw 20 may result in a weakened wall portion adjacent to the head 24. To provide additional strength, the neck 20N may be selected to have a suitable length to provide additional strength in the presence of a larger recessed area. If desired, and as depicted, the head 24 may include a lip portion 28 for engaging the tabs 320T, 330T of the tab locks 320, 330 when utilizing a neck portion 20N of larger lengths.

While the plate assembly 300 may include a coupler for coupling to an intervertebral device, the plate assembly 300 can be utilized independently from an intervertebral device, if desired. For example, with reference to FIG. 12E, once the intervertebral device 100 is positioned adjacent to vertebral bodies 10, 12, the plate 310 of the plate assembly 300 may be positioned and fixedly attached to the adjacent vertebral bodies 10, 12 using vertebral body screws 20, as described immediately above. In this way, the plate 310 and the intervertebral device 100 are independently coupled to the adjacent vertebral bodies 10, 12, without the use of a coupler, such as coupler 300 for example.

Figure 13:
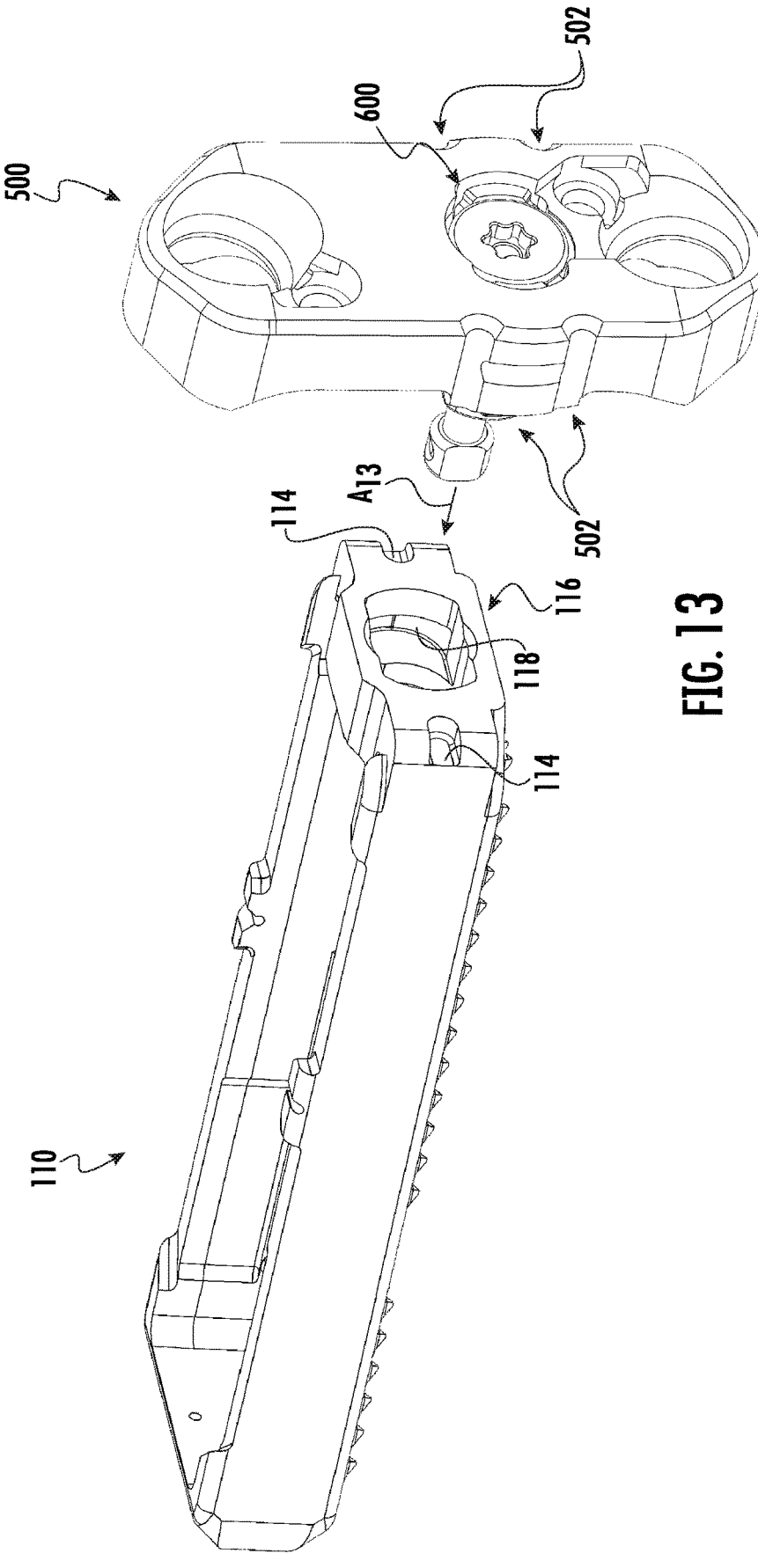
FIG. 13 is a system view of a portion of the intervertebral device of FIG. 1A and another exemplary plate assembly.

Turning to FIG. 13, a system view of a portion of the intervertebral device of FIG. 1A and a plate assembly 500 is depicted. More particularly, for simplicity, only the base 110 of the intervertebral device 100 is depicted, the base 110 including the distal opening 116 having a groove 118 on an inner surface thereof, and grooves 114. The plate assembly 500 may be similar to the plate assembly 300 described above, but may also include structures 502 adapted to aid in installation of the plate assembly 500, adjacent vertebral bodies of a patient for example. The plate assembly 500 may also include a coupler 600. In operation, as with plate assembly 300, the plate assembly 500 is moved toward and interfaces with the base 110, for example, when the base 110, as part of an intervertebral device 100, is positioned between vertebral bodies. As the plate assembly 500 is moved toward the base 110 in a direction depicted by arrow $A_{13}$ a portion of the coupler 600 enters the opening 116 of the base 100 and is operated to engage a portion of the groove 118 to fixedly attach the plate assembly 500 to the base 110 of the intervertebral device 100. As with plate assembly 300, while depicted and described with respect to base 110 of the intervertebral device 100, plate assembly 500 may be adapted to couple to other portions of an intervertebral device, which incorporate elements having similar attributes to groove 118 to facilitate coupling.

Figures 14A, 14B:
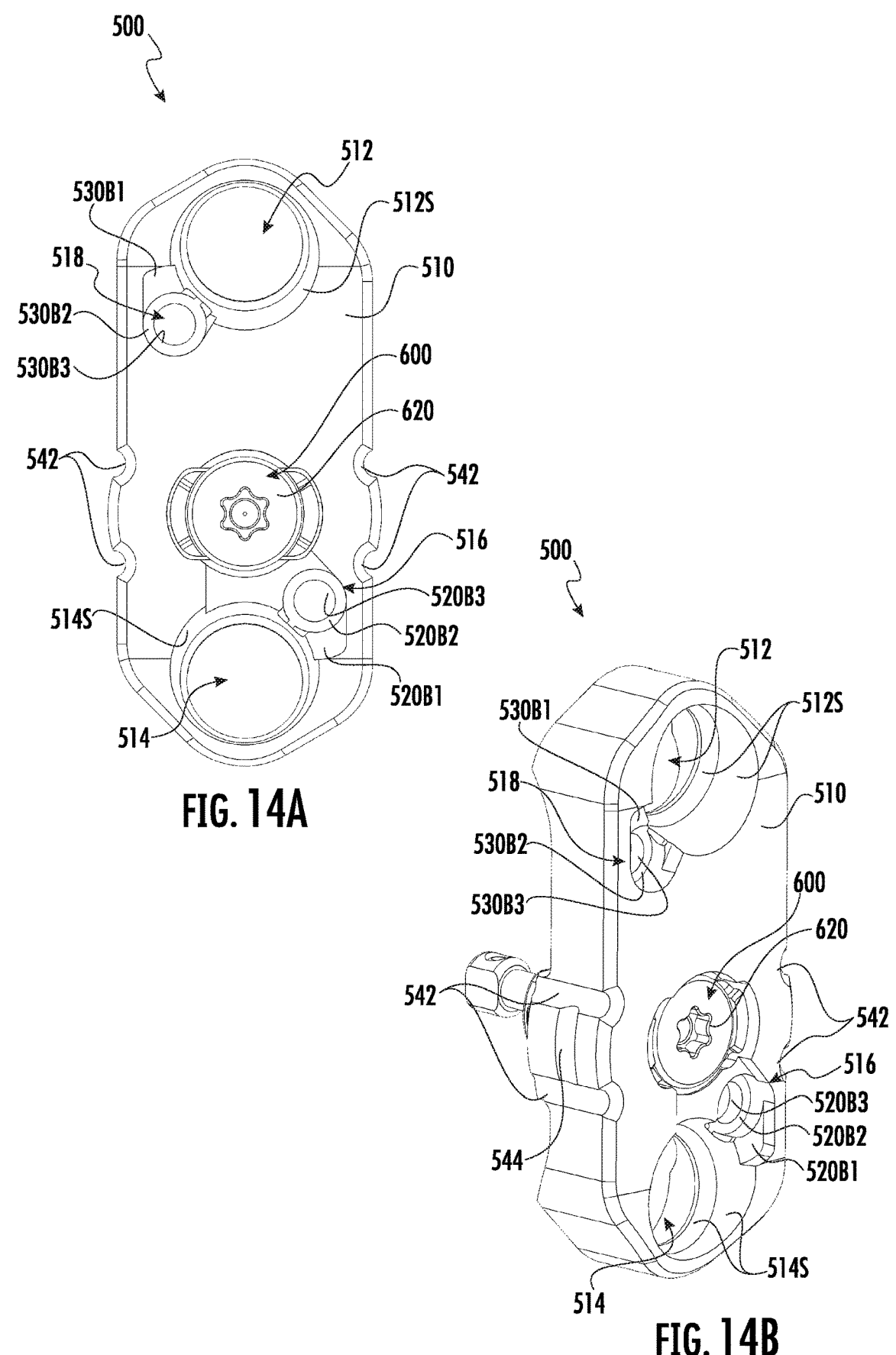
FIG. 14A is a front view of the exemplary plate assembly of FIG. 13.
FIG. 14B is a perspective view of the exemplary plate assembly of FIG. 14A.

Turning to FIGS. 14A and 14B, the plate assembly 500 may include a plate body 510 and a coupler 600, the coupler being adapted to interface the plate assembly 500 with the intervertebral device 100. The plate body 510 may further include an opening 512 and an opening 514. Each of the openings 512, 514 are adapted to accept a vertebral body screw, such as vertebral body screw 20 of FIGS. 12C and 12D, to fixedly attach the plate 510 of the plate assembly 500 to adjacent vertebral bodies. The openings 512, 514 may include inner surfaces 512S, 514S, respectively, having curved surfaces configured to mate with corresponding curved surfaces on the head of an associated vertebral body screw, such as head 24 of vertebral body screw 20. In this way, the vertebral body screw may have a wider range of angular configurations with respect to a vertical axis of the plate body 510 of the plate assembly 500.

Plate body 510 may include an additional opening 516 adapted to receive a first tab lock 520 (not shown, but which may be similar to tab lock 320). The tab lock 320 may include one or more tab portions or tabs 520T. The tab lock 520 may have a lumen therethrough and once positioned within the plate body 510, the portion of the tab lock 520 opposite to the tab 520T may be swaged to secure the tab lock 520 to the plate 510. The coupler 600 may include an elongate member 620 having a threaded portion, as is discussed in greater detail below, and once the elongate member 620 is deployed a second tab 520T of the tab lock 520 may cover the head of the elongate member 620, preventing the elongate member 620 from backing out of the coupler 600, for example. Plate body 510 may include an additional opening 518 adapted to receive a second tab lock 530 (not shown, but which may be similar to tab lock 330) including one or more tab portions 530T. The tab lock 530 may be recessed in a portion of the surface of body 510. As with tab lock 330, the tab lock 530 may include a lumen therethrough, the end opposite the tab 530T being swaged to allow for rotational movement of the tab lock 530, but preventing axial movement of the tab lock 530 back out of the opening 518.

Figures 14C, 14D:
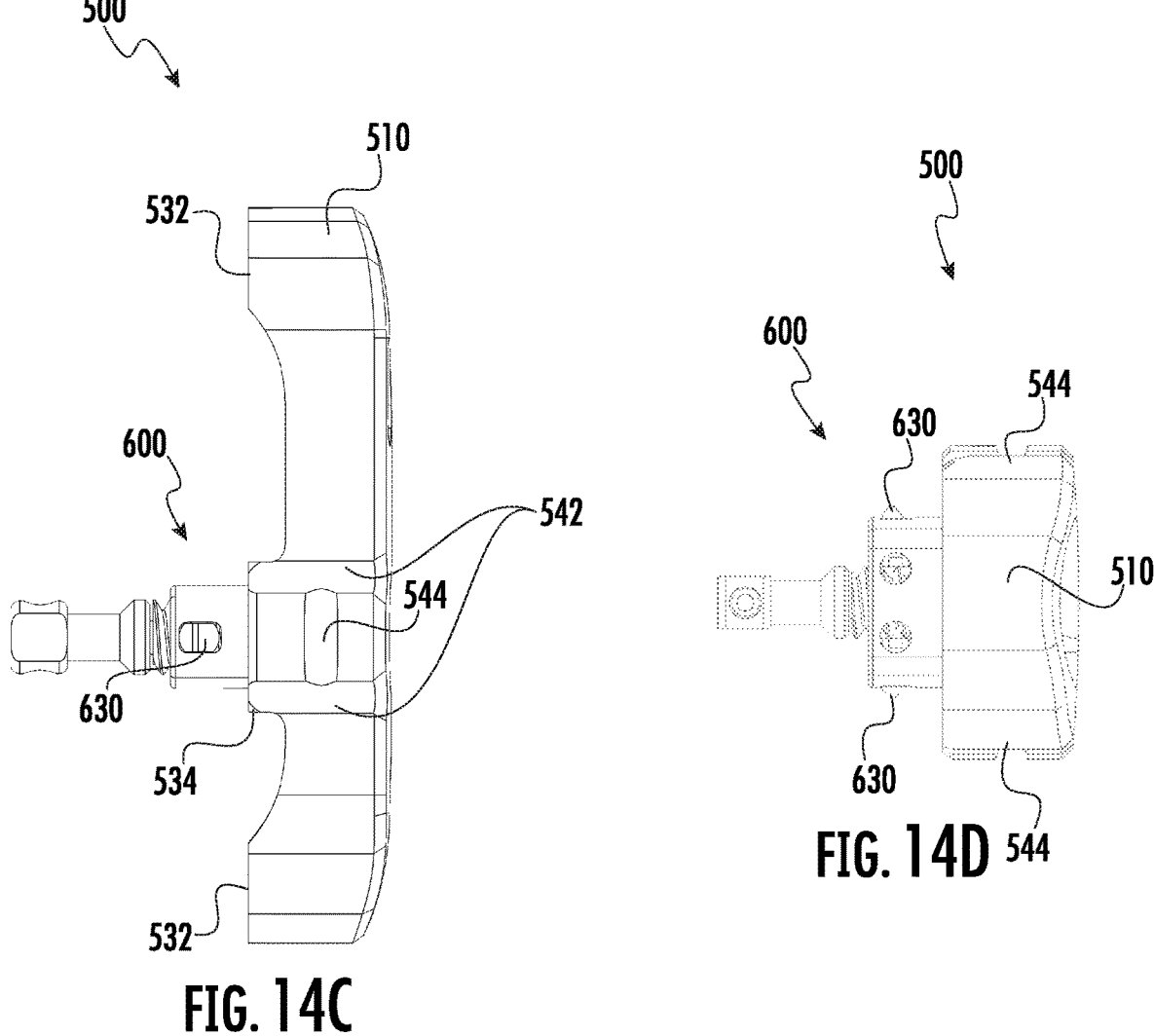
FIG. 14C is a side view of the exemplary plate assembly of FIG. 14A.
FIG. 14D is a top view of the exemplary plate assembly of FIG. 14A.

Turning also to FIG. 14C, a side elevational view of the plate assembly 500 is depicted. As shown, the plate 510 of the plate assembly 500 may include a curved back surface 532, which may provide a better mating surface for adjacent vertebral bodies. The plate body 510 may also include a protrusion 534, which protrudes away from the back surface 532 of the plate body 510 to allow for interfacing with an intervertebral device, such as device 100, while also allowing suitable space to interface with adjacent vertebral bodies. Additionally, the protrusion 534 may have dimensions suitable to hold the back surface 532 of the plate body 510 a known desired distance away from the adjacent vertebral bodies during use. Furthermore, the plate body 510 may be selected to have a suitable width to provide a desired stiffness to help fixedly hold an intervertebral device to the adjacent vertebral bodies. Turning also to FIG. 14D, where a top view of the plate assembly 500 is depicted, the coupler 600 further includes one or more protrusions 630 adapted to interface with a portion of an intervertebral device, the groove 118 of the base 110 of the intervertebral device 100, for example, to fixedly hold the plate assembly 500 to the intervertebral device 100, as discussed in greater detail below with respect to FIGS. 17A-17C.

Figures 15A, 15B:
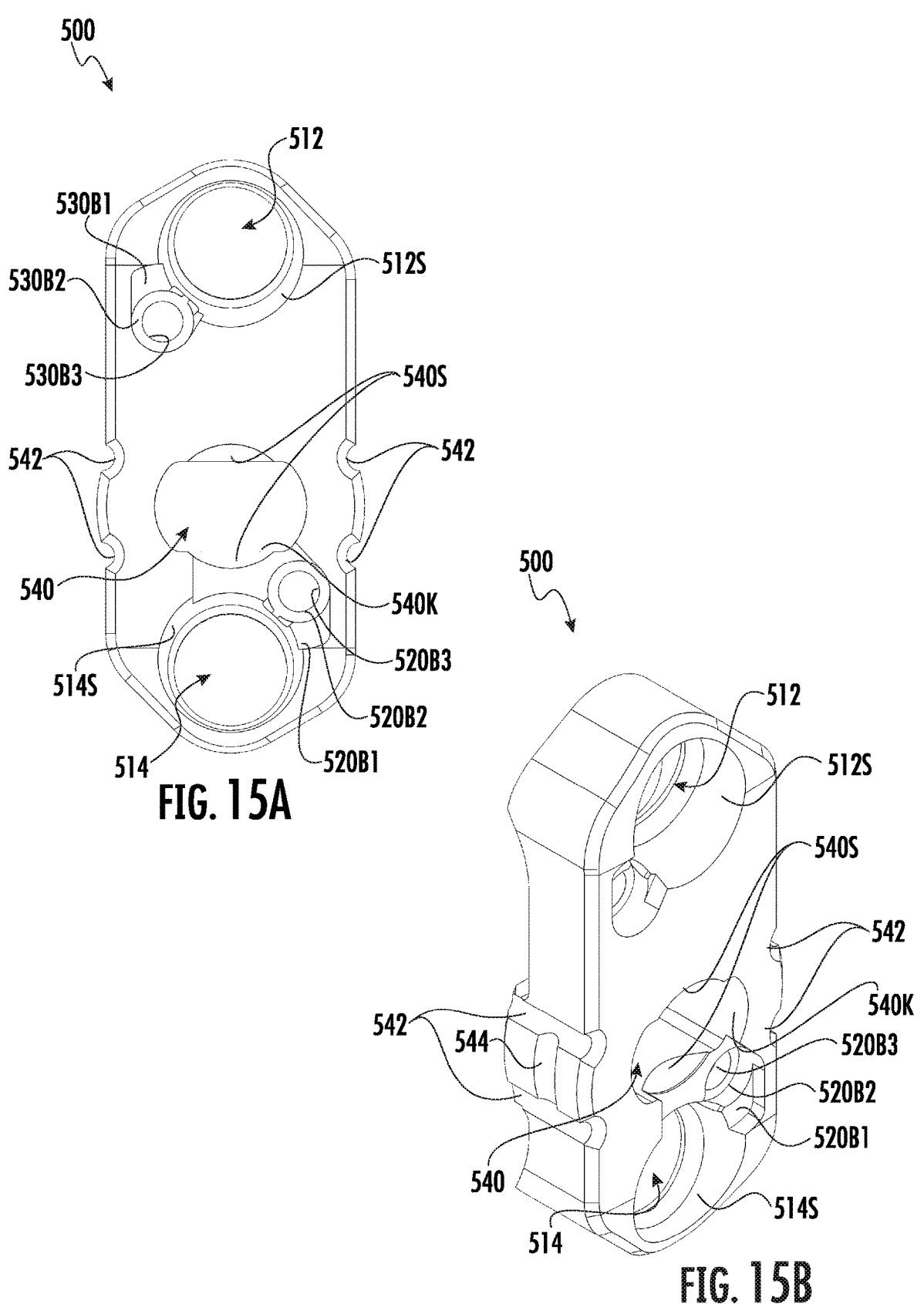
FIG. 15A is a portion of the exemplary plate assembly of FIG. 14A.
FIG. 15B is a first perspective view of the portion of the exemplary plate assembly of FIG. 15A.
Figure 15C:
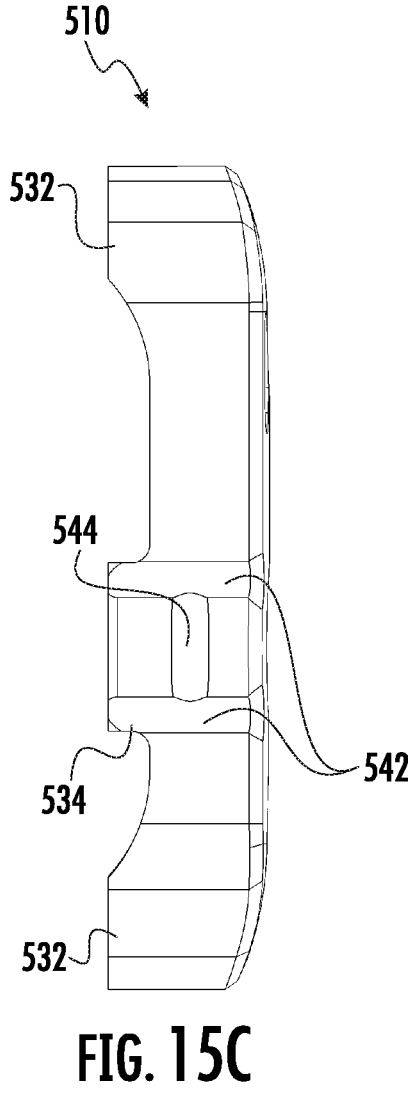
FIG. 15C is a side view of the portion of the exemplary plate assembly of FIG. 15A.
Figure 15D:
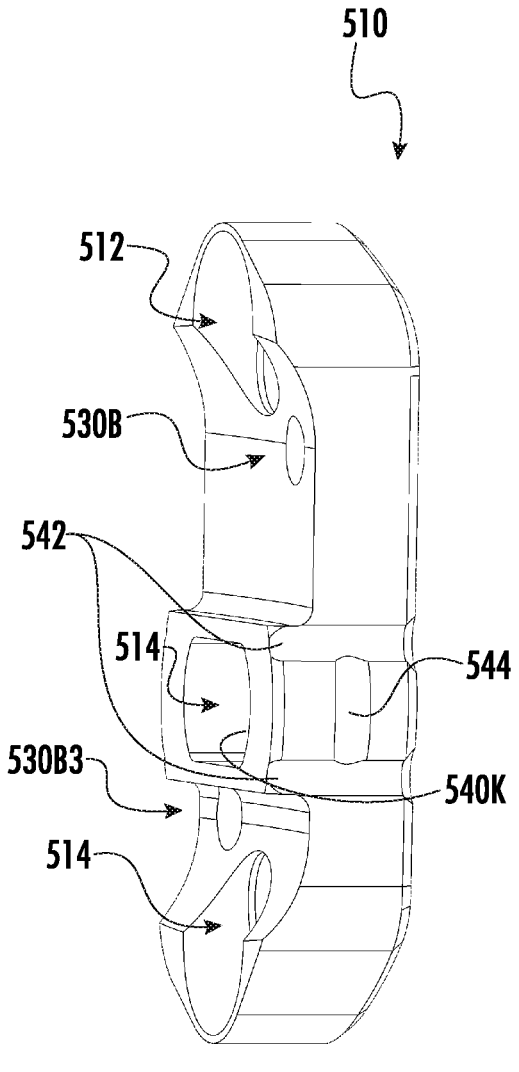
FIG. 15D is a second perspective view of the portion of the exemplary plate assembly of FIG. 15A.

Turning to FIGS. 15A-15D, only the plate body 510 is depicted highlighting features of various openings and surfaces thereof. As with body 310 of plate assembly 300, body 510 may include an opening 540 configured to receive coupler 600, the opening may include a keyed surface 540K to provide a rectangular shape to minimize rotational movement of the coupler 600 in the face of rotational or linear forces applied to the elongate member 620 during operation. Opening 540 may further include a one or more curvilinear surfaces 540S to receive a portion of the coupler 600 to allow the coupler 600 to be positioned recessed within at least a portion of opening 540. As with the plate assembly 300, the one or more curvilinear surfaces 540S may also allow the coupler 600 to couple to the plate body 510 in a number of different axial orientations. For example, once the coupler 600 is positioned within at least a portion of opening 540, a longitudinal axis of the coupler 600 may be non-parallel to a longitudinal axis of opening 540 allowing for ease of coupling between the plate assembly 500 and an intervertebral device during operation. A recessed opening 516 may be provided in the plate body 510 and may be adapted to receive the first tab lock 520 therein. The tab lock 520 (not shown) may be similar to tab lock 320, described above. The recessed opening 516 may include a first recess 520B1, a second recess 520B2, and a third recess 520B3. Recess 520B1 may be adapted to allow the one or more tabs 520T of the tab lock 520 to rotationally move substantially flush with an adjacent surface of the plate body 510. Recess 520B2 and recess 520B3 may be provided for additional stability for the rotational movement of the tab lock 520. Recess 520B3 may proceed through the back of the plate body 510, as shown in FIG. 15D. In similar fashion, a recessed opening 518 may be provided in the plate body 510 adapted to receive a second tab lock 530 therein. The tab lock 530 (not shown) may be similar to tab lock 320, described above. The recessed opening 518 may include a first recess 530B1, a second recess 530B2, and a third recess 530B3. Recess 530B1 may be adapted to allow the one or more tabs 520T to rotationally move substantially flush with an adjacent surface of the plate body 510, as with tab lock 320. Recess 530B2 and recess 530B3 may be provided to provide additional stability for the rotational movement of the tab lock 530. Recess 530B3 may proceed through the back of the plate body 510, as shown in FIG. 15D. The protrusion 534 may include one or more additional protrusions (not shown), each of the one or more protrusions adapted to interface with a portion of an intervertebral device, for example, a respective one of the grooves 114 of the base 110 of the intervertebral device 100, to provide additional support and reduce mobility of the plate assembly 500 with respect to an intervertebral device when attached thereto.

Figure 16:
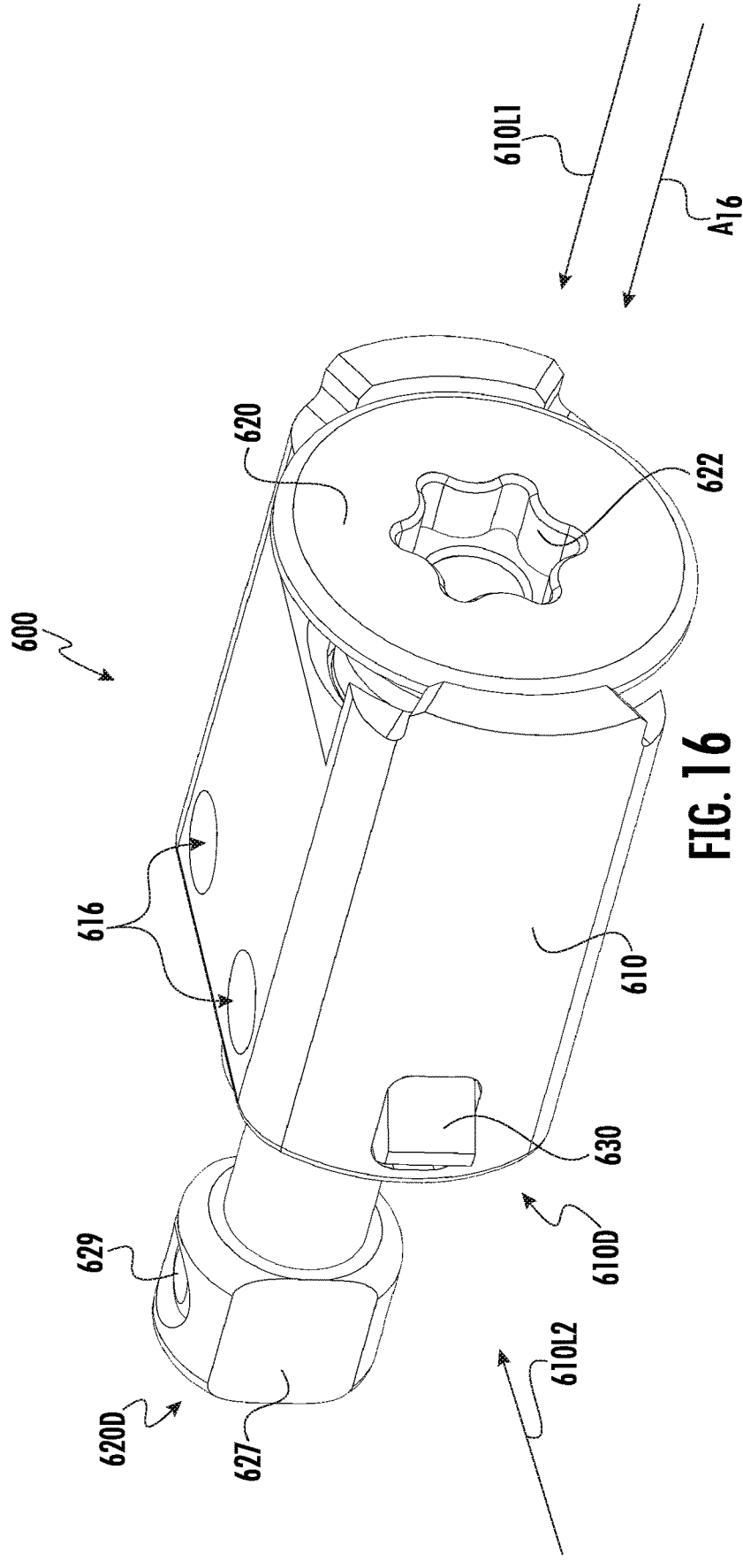
FIG. 16 is a perspective view of another exemplary coupler.

With reference to FIG. 16, coupler 600 will be described in greater detail. Coupler 600 is similar to coupler 400 in functionality, but is configured differently. As shown, coupler 600 may include a housing 610, an elongate member 620, and one or more protrusions 630. The housing 610 includes a first lumen 610L1 therethrough, the elongate member 620 adapted to translate through the lumen 610L1 of the housing 610, ending in a distal portion 620D. A cap 627 is fixedly attached to the elongate member 620 through the use of a pin 629, the cap 627 incorporating a transition portion, as discussed in greater detail below. A distal portion 610D of the housing 610 may include a second lumen 610L2, which is substantially perpendicular to the first lumen 610L1, the one or more protrusions 630 being adapted to translate within the second lumen 610L2. In certain embodiments, the elongate member 620 may be adapted to translate linearly through at least a portion of the lumen 610L1. Alternatively, elongate member 620 may include a threaded portion that rotationally interfaces with a corresponding threaded portion of housing 610, as described in greater detail below with reference to FIGS. 17A-17C. In operation, the elongate member 620 is adapted to translate through the lumen 610L1 of housing 610 in a direction as depicted by arrow A16, the cap 627 including surface transitions along its length resulting in the one or more protrusions 630 to radially move away from the elongate member 620 and exit an opening in the distal end 610D of the inner housing 610, as generally depicted. Protrusions 630 may then be utilized to fixedly attach the plate assembly 600 to an intervertebral device, such as intervertebral device 100. The protrusions 630 may be similar to protrusions 430, as contemplated and described above relative to the coupler 400. The housing 610 may also include additional openings 616 adapted to retain protrusions 630 within the inner housing 630, in a similar fashion as described relative to protrusions 430 and inner housing 310.

Figure 17A:
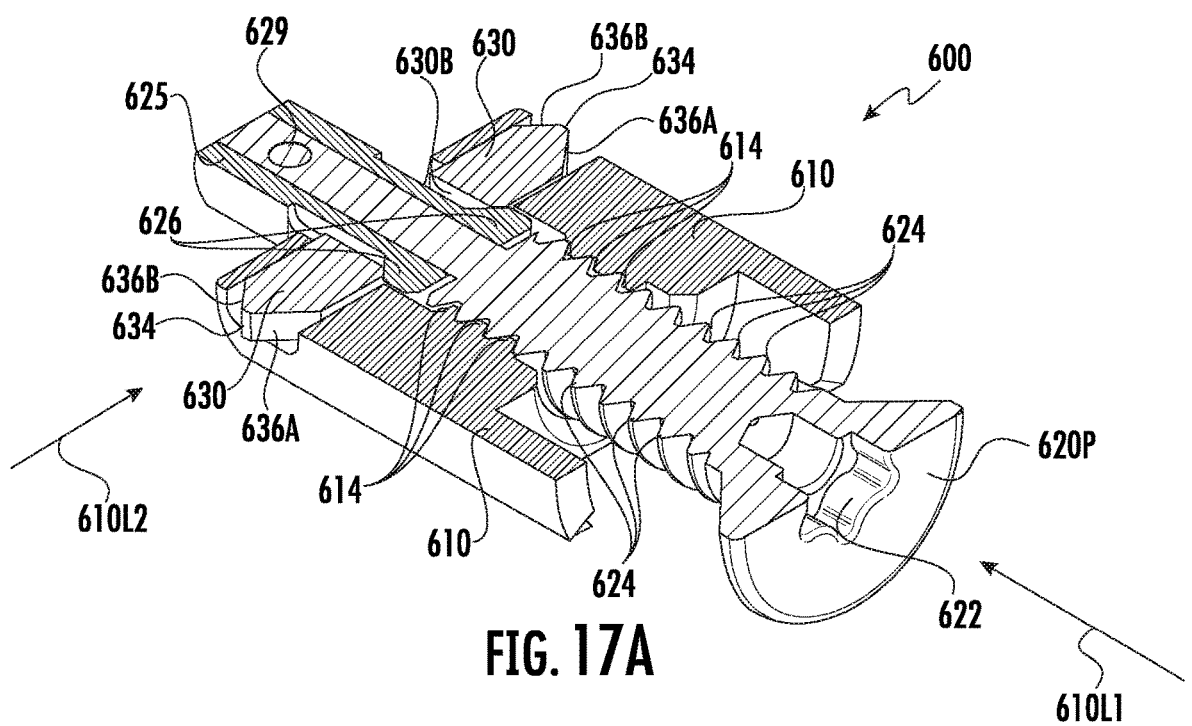
FIG. 17A is a perspective section view of the exemplary coupler of FIG. 16 in an operative configuration.
Figure 17B:
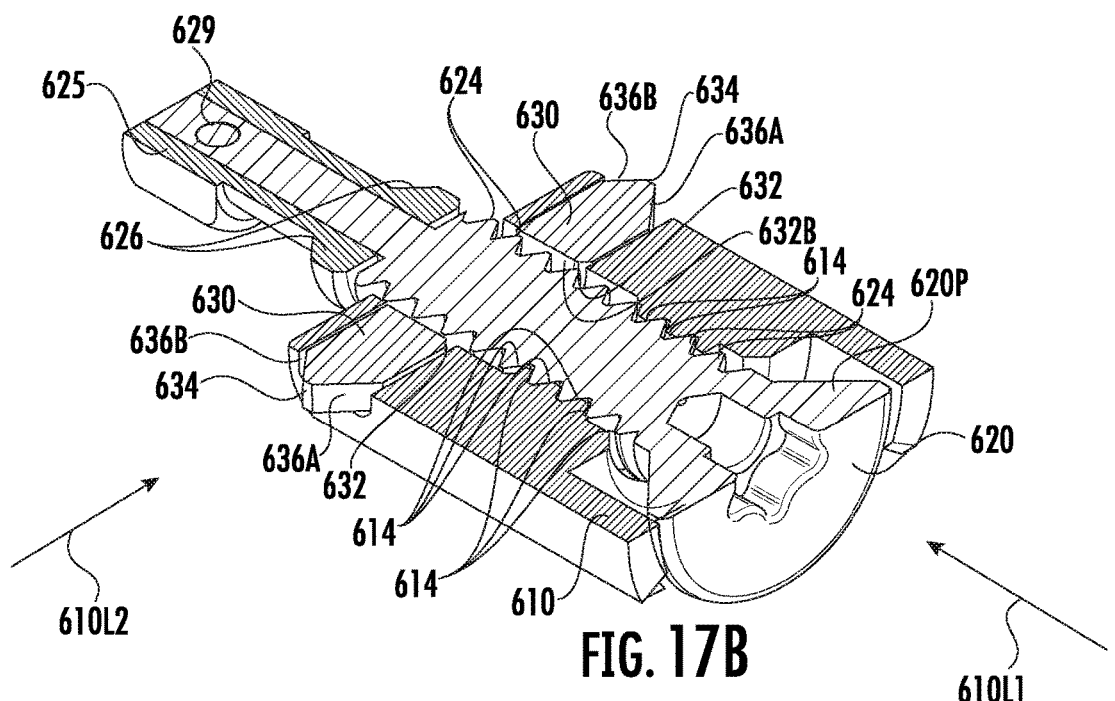
FIG. 17B is a perspective section view of the exemplary coupler of FIG. 17 in another operative configuration.
Figure 17C:
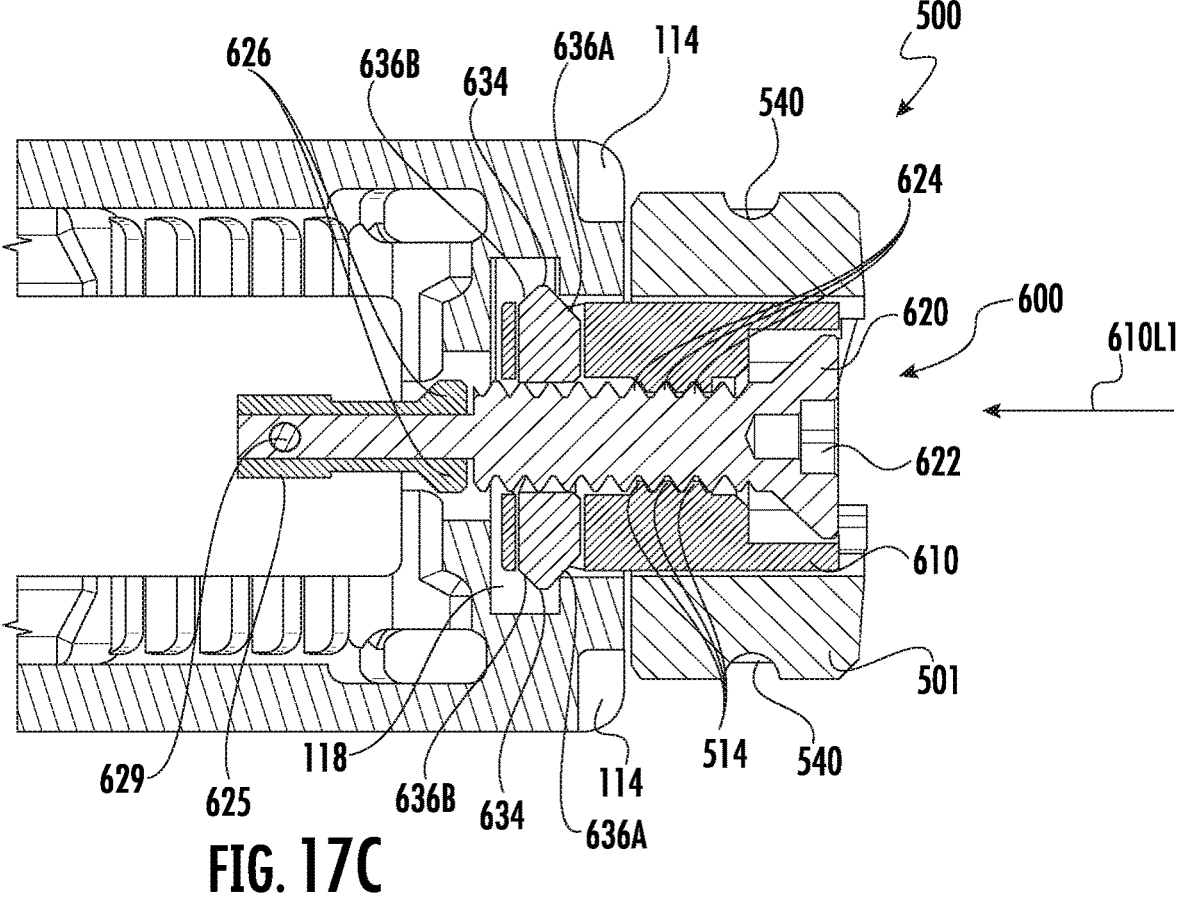
FIG. 17C is a top section view of a portion of the intervertebral device of FIG. 1A and exemplary plate assembly of FIG. 14A.

With reference to FIGS. 17A-17C, the coupler 600 operation will be described in greater detail. Turning specifically to FIG. 17A and as a quick reminder, the coupler 600 includes housing 610, elongate member 620 with cap 627 attached thereto via pin 629, and one or more protrusions 630. The housing 610 may include a matching keyed shape similar to the keyed shape 540K of opening 540 of plate body 510 to help maintain relative rotational position therebetween during use. The housing 610 may include first lumen 610L1 extending therethrough along a longitudinal axis of the housing 610, and second lumen 610L2 extending therethrough along an axis perpendicular to the longitudinal axis of the housing 610. Lumen 610L1 of the housing 610 may include a threaded portion 614 configured to couple to a portion of the elongate member 620. The elongate member 620 may include a cap 625, the cap 625 including an interference surface 626 adapted to couple to the one or more protrusions 630. The cap 625 may be held to elongate member 620 through any suitable means, such as through compression fitting, or the use of an epoxy. Alternatively, and as shown, cap 625 may be attached to elongate member 620 through a pin 629 which extends therethrough. The pin 629 may include a head portion which abuts a portion of the cap 625 and a hollow opposing portion, which may be swaged to fixedly attach the pin 629 to the elongate member 620 and cap 625. The cap 625 may prevent the elongate member 620 from backing out of the first lumen 610L1 since the transition portion 626 of the cap 625 abuts the threaded portion of the housing 610.

The coupler 600 may include one or more protrusions 630. For example, a first protrusion 630 may be positioned in a first radial portion of the second lumen 610L2, and a second protrusion 630 may be positioned in a second radial portion of the second lumen 610L2, as shown. As described above with respect to similar protrusion 330, protrusion 630 may include a number of interface surfaces, each of which may interact with adjacent structures during operation. In particular, the interference surface 632 may interfere with a portion of the elongate member 620, including a cap having a transition portion, as described in greater detail below. Furthermore, sloped surface 636A may be configured to interfere with a portion of an intervertebral device, the groove 118 of the base 110 of intervertebral device 100, for example, during operation. Additionally, it should be understood that additional protrusions 630 may be positioned within additional lumens 610L of the housing 610, if desired, to provide additional mechanical connectivity to an intervertebral device.

As shown and as with elongate member 420, the elongate member 620 may include a recessed portion 622 adapted to receive a tool for rotational movement thereof. Elongate member 620 may also include a threaded portion 624 adapted to interface with the threaded portion 614 of the housing 610 to allow for movement of the elongate member 620 with respect to the housing 610 through lumen 610L1 during rotation of the elongate member 620. The cap 625 may include a transition portion 626 located distal to the threaded portion 624, the transition portion 626 may be formed from a conical surface about the elongate member 620, the conical surface adapted to interfere with the surface 632 of protrusion 630, resulting in axial movement of the protrusion 630 away from central lumen 610L, as described in greater detail below. Additionally, once the elongate member 620 is positioned within the lumen 610L1, the cap 625 may be attached to the elongate member 620 using the pin 629. Once attached, the transition portion 626 of the cap 625 may prevent the elongate member 420 from completely retracting out of the housing 610. As will be understood in the description immediately below, a proximal end 620P of the elongate member 620 may be sized to interfere with a surface of the plate 510 to fixedly hold the plate to the coupler and, ultimately, to an intervertebral device attached thereto.

In operation, as depicted in FIG. 17A, elongate member 620 is in a retracted position within lumen 610L1 such that the bottom surface 630B of each protrusion 630 is free to move in the lumen 610L2 and rest against a surface of the cap 625. As the elongate member 620 is rotated in a first direction, the elongate member 620 may translate further into lumen 610L1, and the sloped surface 632 of each protrusion 630 may interfere with the transition portion 626 of the cap 625. Turning to FIG. 17B, as the elongate member 620 is rotatably operated to move distally in the lumen 610L1, the transition portion 626 of the cap, as part of elongate member 620, engages the sloped surface 632 of the bottom surface 630B of each protrusion 630. In response, each protrusion 630 moves radially in a direction away from the first lumen 610L1. As the elongate member 620 is further rotationally operated the bottom surface 630B of each protrusion 630 travels further along the transition portion 626 and on top of the threaded portion 624 of the elongate member 620. When the bottom surface 630B of each protrusion 630 is engaging the top of the threaded portion 624 of the elongate member 620, distal surface 634 of each protrusion 630 extends out the corresponding radial opening of the lumen 610L2.

Referring also to FIG. 17C, a section view of the coupler 600 and the base 110 of the intervertebral device 100 is depicted. For clarity purposes only, the remaining portions of the intervertebral device 100 are not shown. When the elongate member 620 fully engages the housing 610 within the lumen 610L1, the bottom surface 632 of each protrusion 630 rides on top of the threaded portion 624 of the elongate portion 620. In this configuration, the tip 634 of each protrusion 620 enters the groove 118 of the base 110 and the sloped surface 636A of each protrusion 630 interferes with a side surface of the groove 118, respectively, as depicted, effectively fixedly connecting the plate 500 to the intervertebral device 100. Once the elongate member 620 is fully engaged, the plate assembly 500 is fixedly coupled to the intervertebral device 100. A vertebral body screw may then be placed in each of the openings 612, 614, respectively, of the plate 610, and screwed into place to fixedly hold the plate to adjacent vertebral bodies. If desired, the vertebral body screws may be positioned to fixedly couple the plate 500 to the adjacent vertebral bodies prior to fixedly coupling the plate 500 to the intervertebral body 100, although alignment of the plate assembly 500 to the intervertebral body 100 may prove to be challenging.

As with plate assembly 300, if the elongate member 620 of plate assembly 500 is rotatably operated in a second direction, the elongate member 620 may move proximally. Once the transition portion 626 of the elongate member 620 is located proximal to the second lumen 610L2, further interference between the sloped surface 636A of each protrusion 630 and the groove 118 of the base element 110 results in the radial movement of the protrusion 630 toward the first lumen 610L1, and detachment of the plate assembly 500 from the intervertebral device 100. Such independent movement of the protrusion 630 with respect to the remaining portions of the coupler 500 results in a less complicated and more reliable method to retain a plate assembly to an intervertebral device. As should be readily understood, as the protrusion 630 independently moves with respect to remaining portions of the coupler 600, with the elongate member 620 retracted and each protrusion tip 634 exiting the second lumen 610L2, the sloped surface 636B may interfere with the opening of the intervertebral device resulting in the protrusion 630 moving radially toward the first lumen 610L1, the bottom surface 630B of each protrusion 630 abutting the cap 625, for example.

Figure 17D:
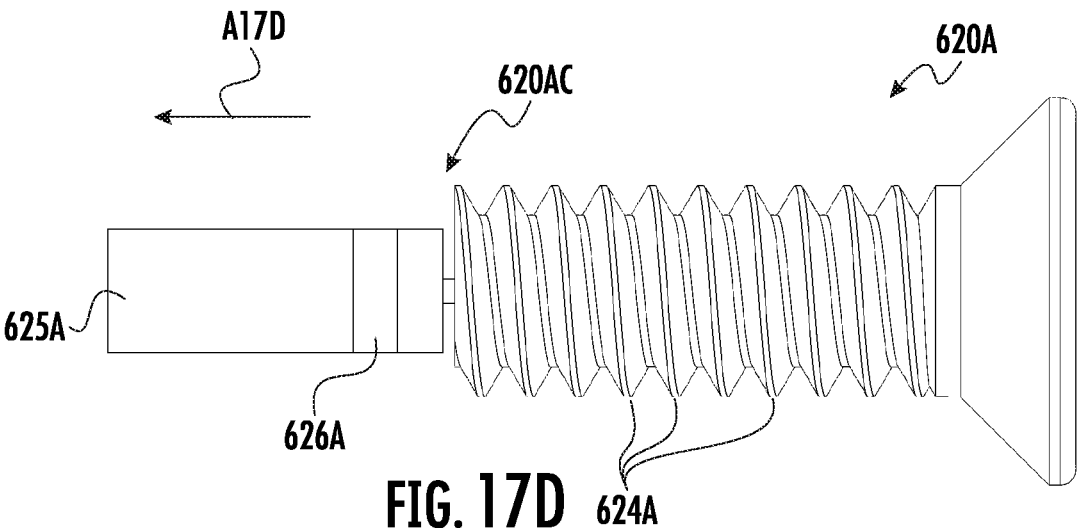
FIG. 17D is a side view of an alternative elongate member that may be utilized in the exemplary coupler of FIG. 16.
Figure 17E:
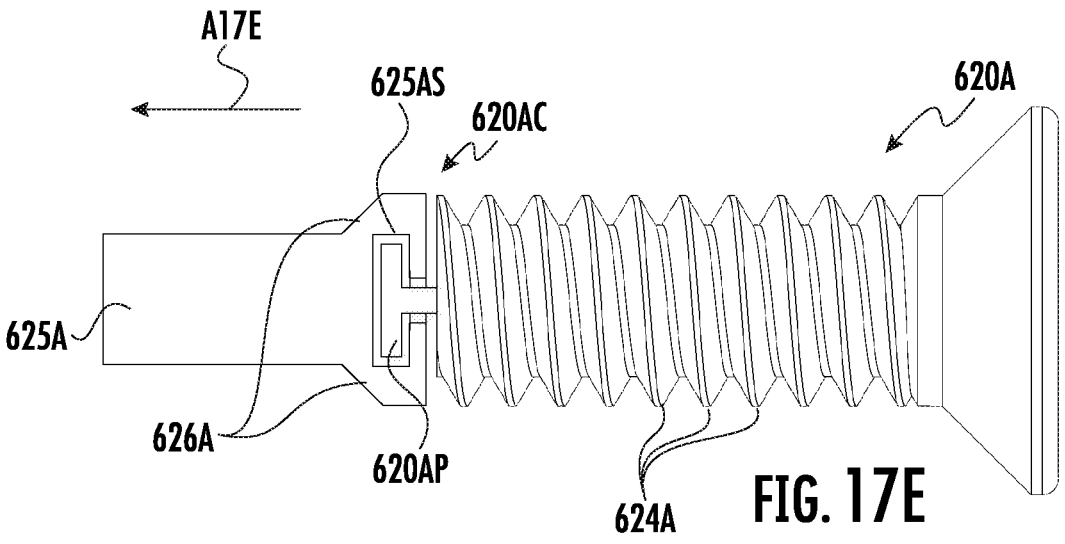
FIG. 17E is a top view of the alternative elongate member of FIG. 17D.

While the various embodiments of the elongate member, and associated sub elements such as a cap, for example, have been described to rotatably operate, other embodiments may include an elongate member that operates, at least partially, in a linear fashion. For example, with reference to FIGS. 17D and 17E, a coupler 600A may include an elongate member 620A. Elongate member 620A may be similar to elongate member 620 of coupler 600, but may include an interface 620AC to interface the elongate member 620A to a cap 625A. More specifically, the interface 620AC may be configured to allow the elongate member 620A to rotate with respect to the cap 625A. In this way, the elongate member 620A may rotationally operate, as described above with respect to elongate member 620, and the resulting transition of elongate member 620A causing the cap 625A to move in the direction as indicated by arrows A17D, A17E depicted in FIGS. 17D and 17E, respectively. The interface 620AC may include a protrusion 620AP of the elongate member 620A and a slot 625AS of the cap 625A. Elongate member 620A may include a threaded portion 624A to interface with a housing of the coupler 600A, and end in the protrusion 620AP. The protrusion 620AP may be sized to fit within the slot 625AS in the cap 625A, as generally depicted. The slot 625AS may pass through a portion of the cap 625A, or pass completely through the cap 625A, as desired. Once the elongate member 620A is interfaced to the cap 625A, the elongate member 620A may rotate with respect to the cap 625A, however translation of the elongate member 620A results in a corresponding linear translation of the cap 625A, the cap 625A translating without rotating for example. As with cap 625, the cap 625A may include transitions 626A, which may be configured to interfere with protrusions of the coupler to facilitate engagement to an intervertebral device, as described with reference to coupler 600.

Figure 17F:
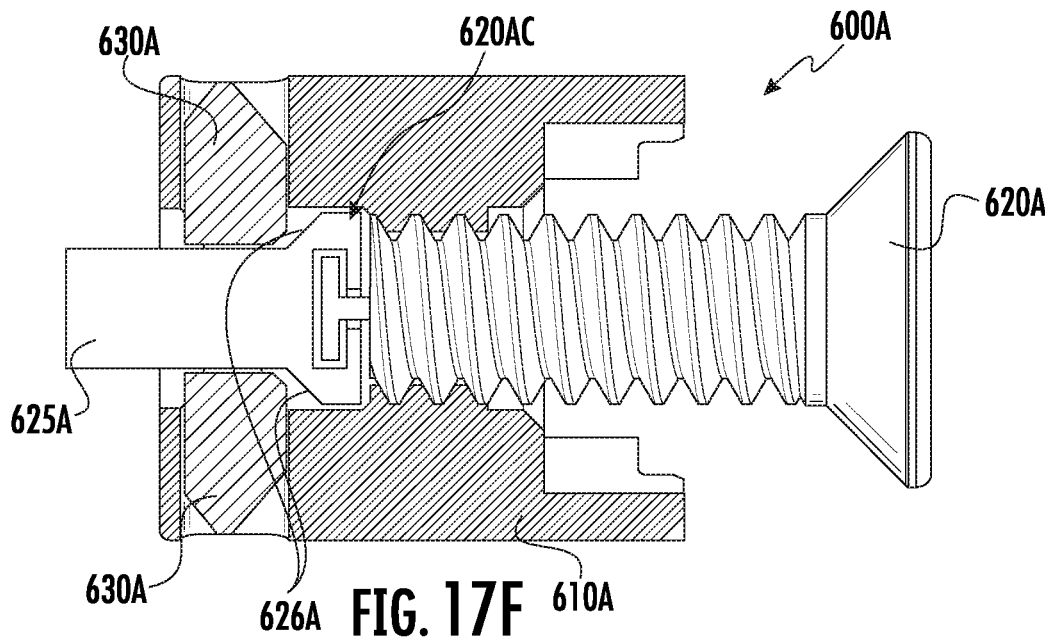
FIG. 17F is a section view of the alternative elongate member of FIG. 17D in another exemplary coupler, the alternative elongate member being in a first retracted configuration.
Figure 17G:
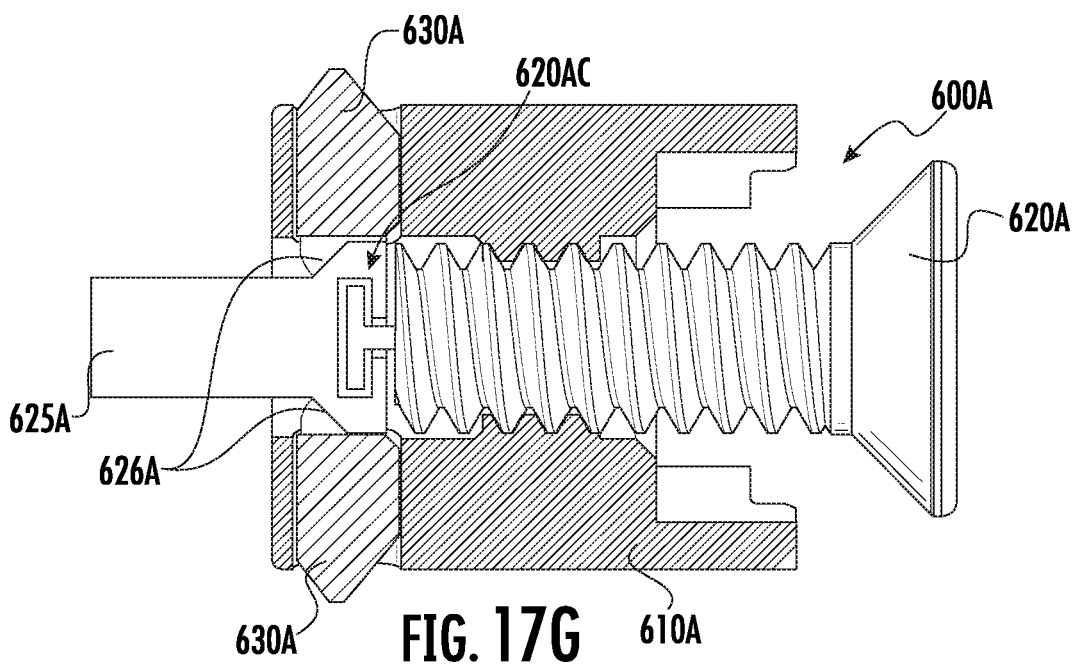
FIG. 17G is another section view of the alternative elongate member of FIG. 17D in the exemplary coupler of FIG. 17F, the alternative elongate member being in a second inserted configuration.

With reference now to FIGS. 17F and 17G, the coupler 600A may include a housing 610A, the housing 610A having a first lumen 610AL1 and a second lumen 610AL2, and protrusions 630A, each functionally similar to housing 610 and protrusions 630, as discussed above. Referring specifically to FIG. 17F, with the elongate member 620A in a retracted configuration within the first lumen 610AL1, the protrusions 630A may be allowed to freely move within the second lumen 610AL2, the protrusions 630A located within the housing 610A, for example. As the elongate member 620A moves from the retracted configuration toward an inserted position, transitions 626A interfere with the protrusions 630A, as described in greater detail above with respect to coupler 600, a portion of the protrusions 630A protruding out from the second lumen 610AL2 of the housing 610A to interface with an intervertebral device, such as intervertebral device 100.

Figure 18A:
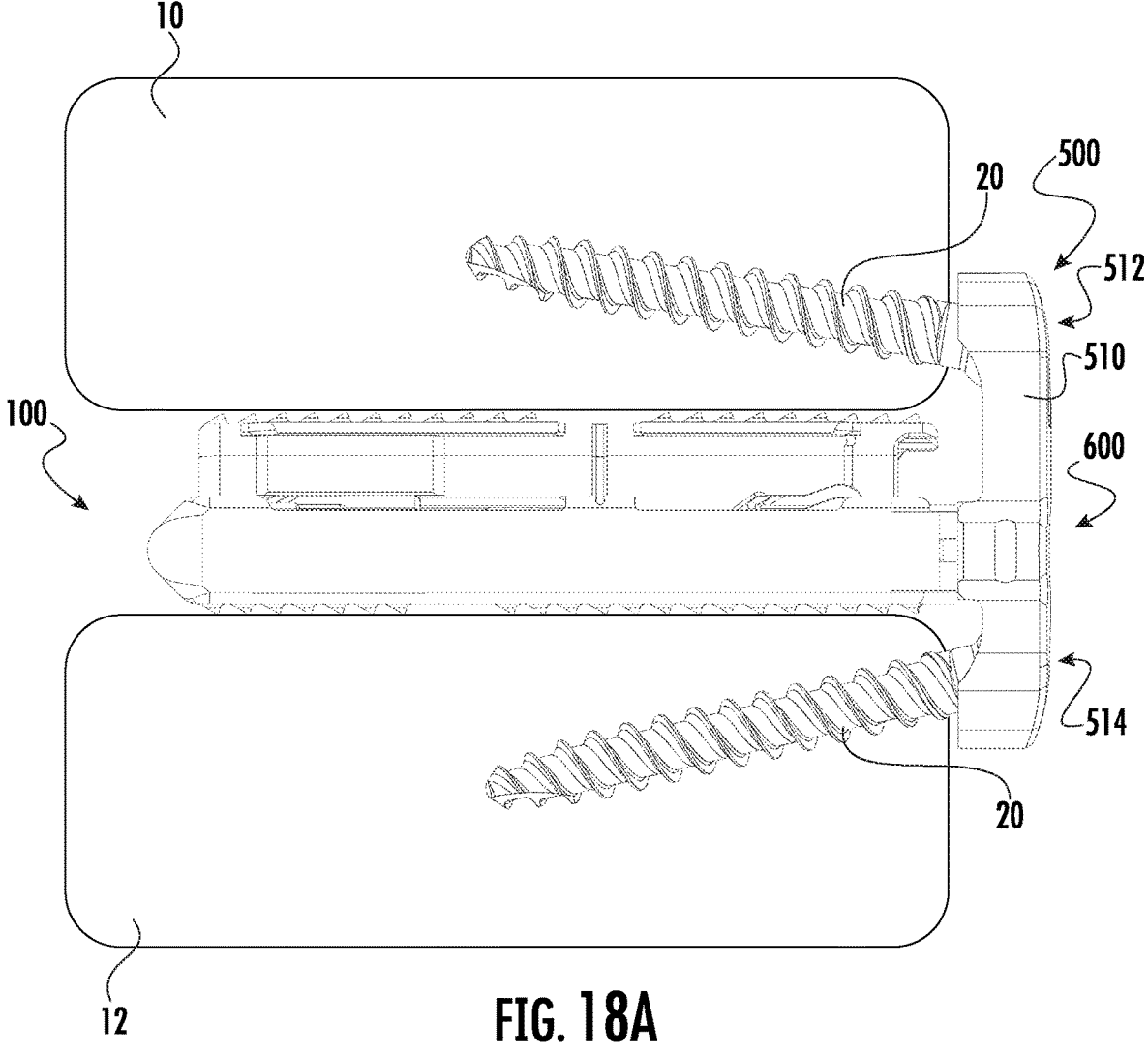
FIG. 18A is a symbolic side view of the plate assembly of FIG. 14A coupled to both, the intervertebral device of FIG. 1A and adjacent vertebral bodies.
Figure 18B:
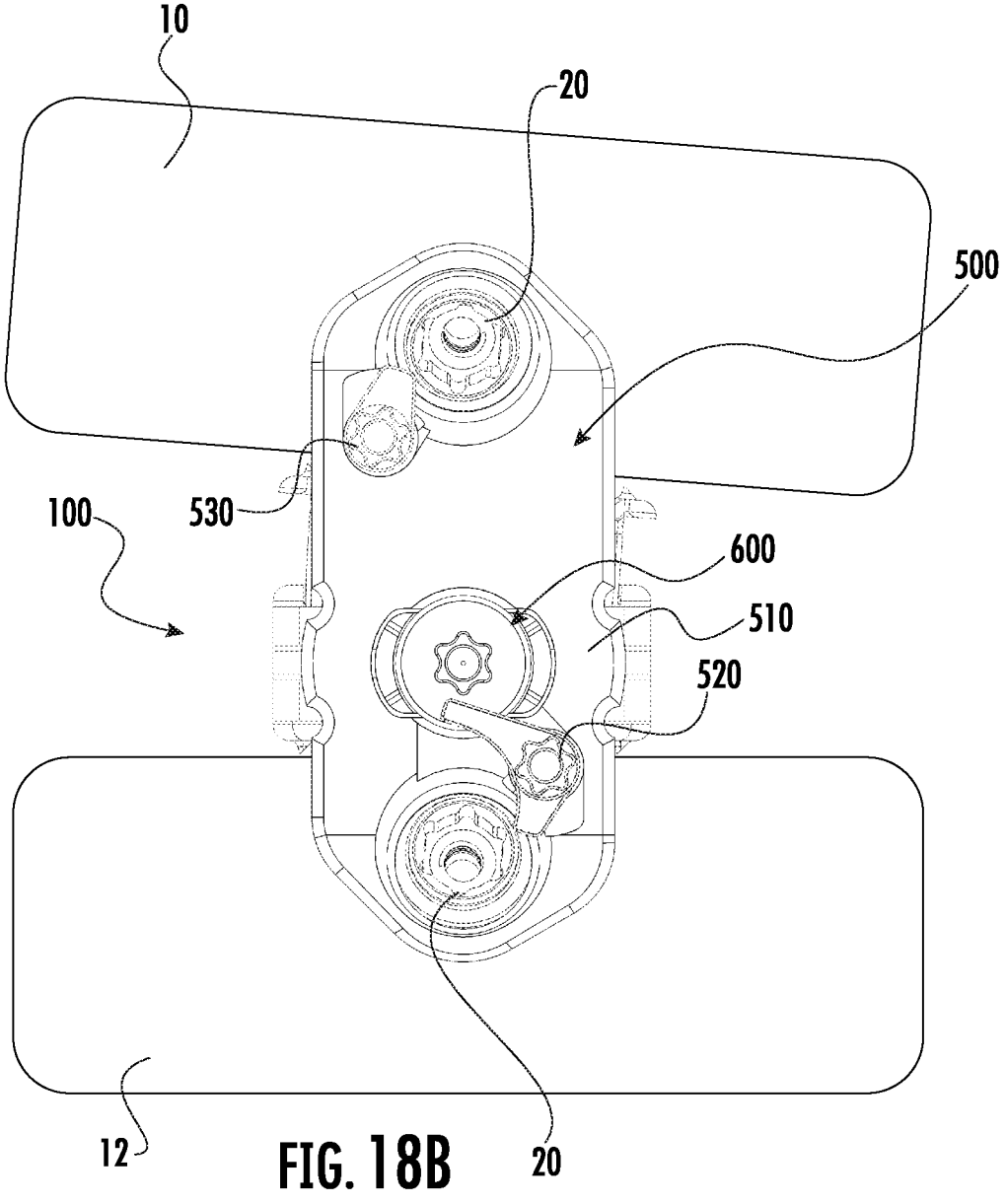
FIG. 18B is symbolic end view of the plate assembly of FIG. 14A coupled to both, the intervertebral device of FIG. 1A and adjacent vertebral bodies.
Figure 18C:
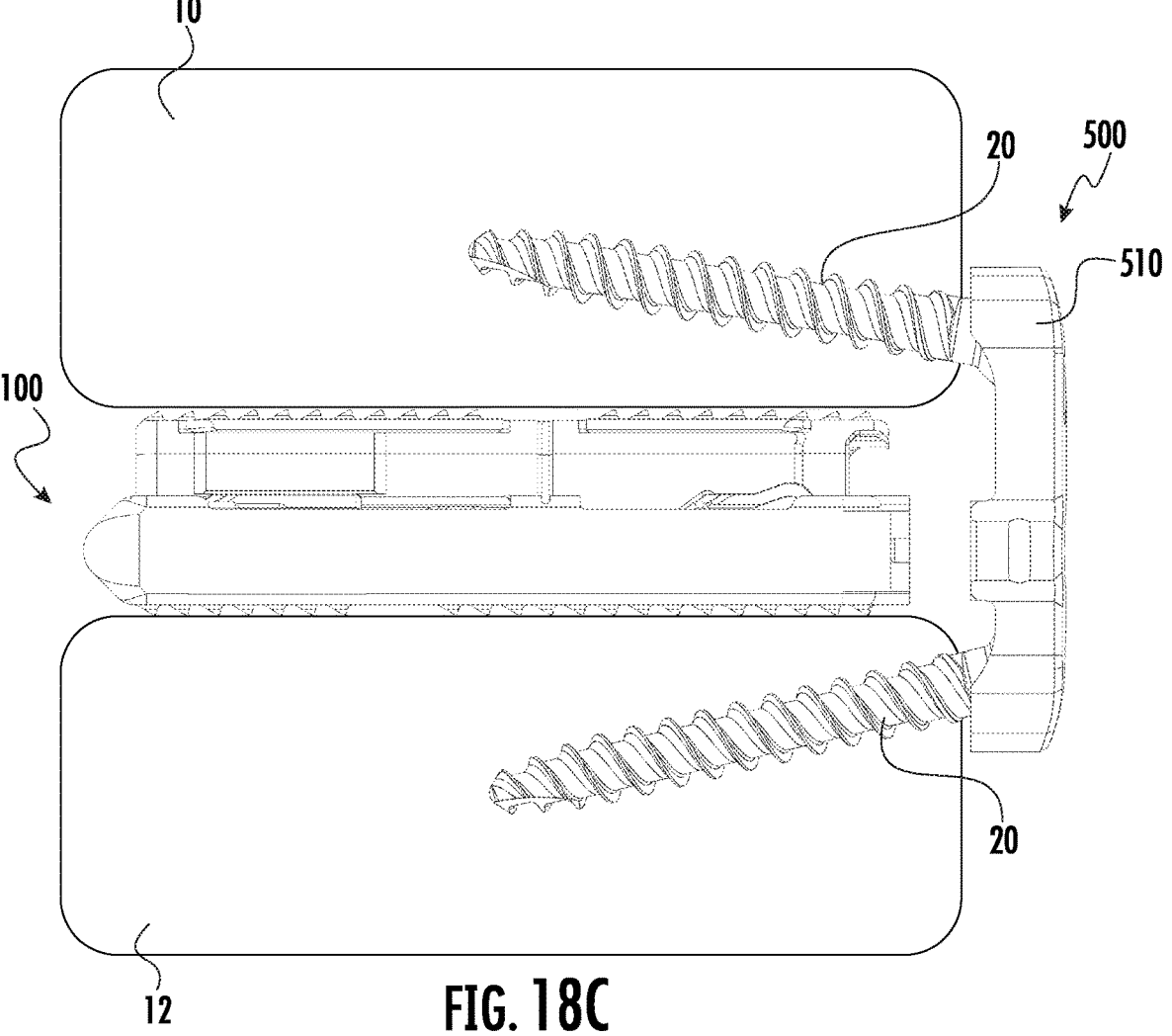
FIG. 18C is a side view of the plate assembly of FIG. 14A and the intervertebral device of FIG. 1A, each independently coupled to adjacent vertebral bodies.

Turning to FIGS. 18A-18C, exemplary positioning of the plate assembly 500 relative to an interventional device and adjacent vertebral bodies is described. The depictions of FIGS. 18A-18C are for illustrative purposes only and, therefore, are not necessarily to scale. FIG. 18A depicts an exemplary placement of an intervertebral device, such as intervertebral device 100, in an expanded configuration between first vertebral body 10 and second vertebral body 12. Once positioned, the plate assembly may then be positioned adjacent to and coupled with the intervertebral device 100, as described with respect to FIG. 11D above. Once the plate assembly 500 is coupled to the intervertebral device 100, the plate assembly 500 may be fixedly attached to the adjacent vertebral bodies through the use of one or more vertebral body screws, such as vertebral body screws 20. For example, a first vertebral body screw 20 may be advanced through opening 612 of the plate 610 and into the first vertebral body 10, and a second vertebral body screw 20 may be advanced through opening 614 of the plate 610, as generally depicted. Turning to FIG. 18B, an end view of the plate assembly 500 coupled to the intervertebral device 100 and adjacent vertebral bodies 10, 12 is depicted. As shown, once the vertebral body screws 20 are positioned, the tab locks 620, 630 may be rotationally operated to position tab portions 620T, 630T over corresponding heads of vertebral body screws 20, as well as elongate member 620 of coupler 600, maintaining the position of the screws 20 and elongate member 620 relative to the coupler 600.

While the plate assembly 500 may include a coupler for coupling to an intervertebral device, the plate assembly 500 can be utilized independently from an intervertebral device, if desired. For example, with reference to FIG. 18C, once the intervertebral device 100 is positioned adjacent to vertebral bodies 10, 12, the plate 510 of the plate assembly 500 may be positioned and fixedly attached to the adjacent vertebral bodies 10, 12 through the use of vertebral body screws 20, as described immediately above. In this way, the plate 510 and the intervertebral device 100 are independently coupled to the adjacent vertebral bodies 10, 12.

Figure 19A:
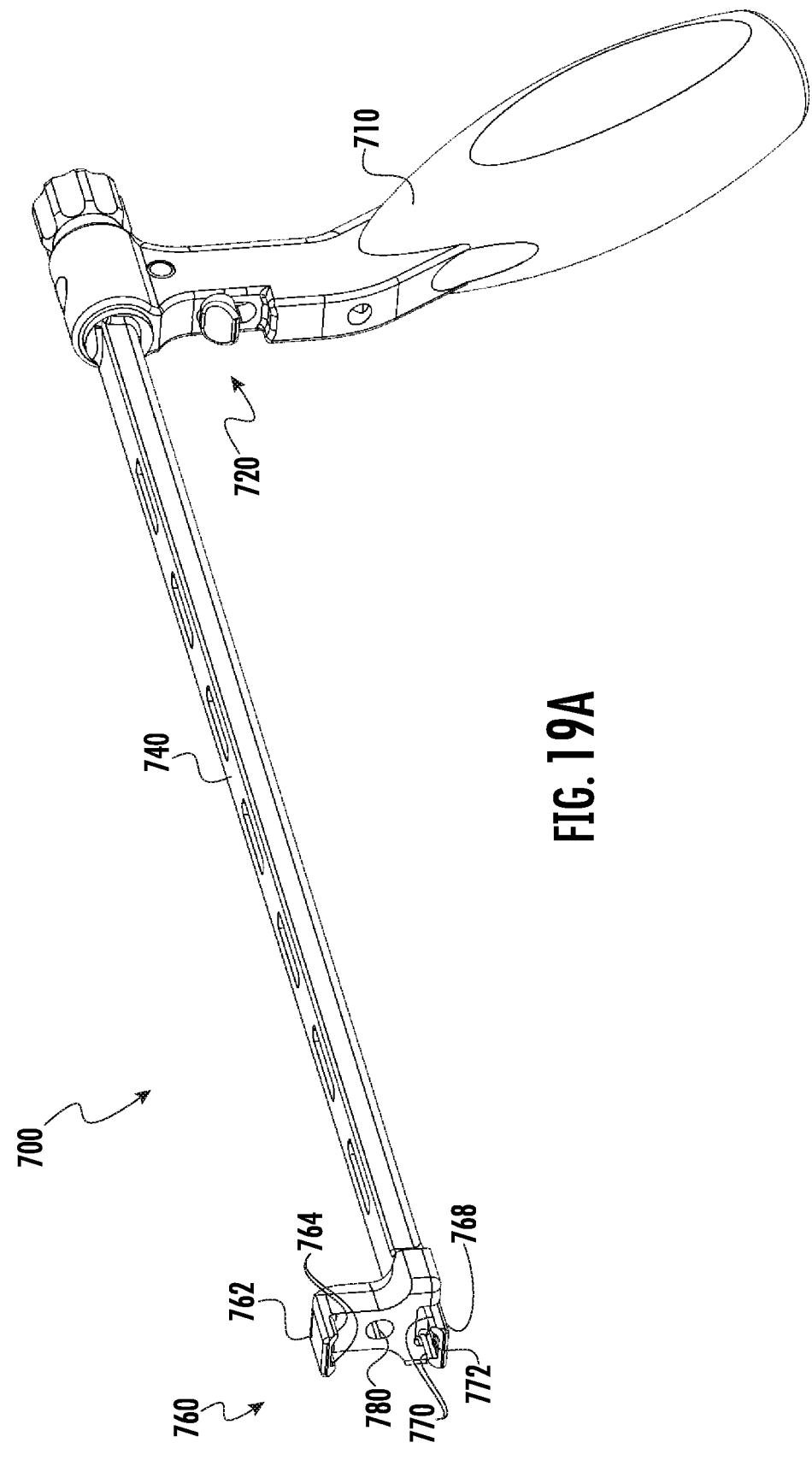
FIG. 19A is a perspective view of a plate assembly installation tool.
Figures 20A, 20B, 20C:
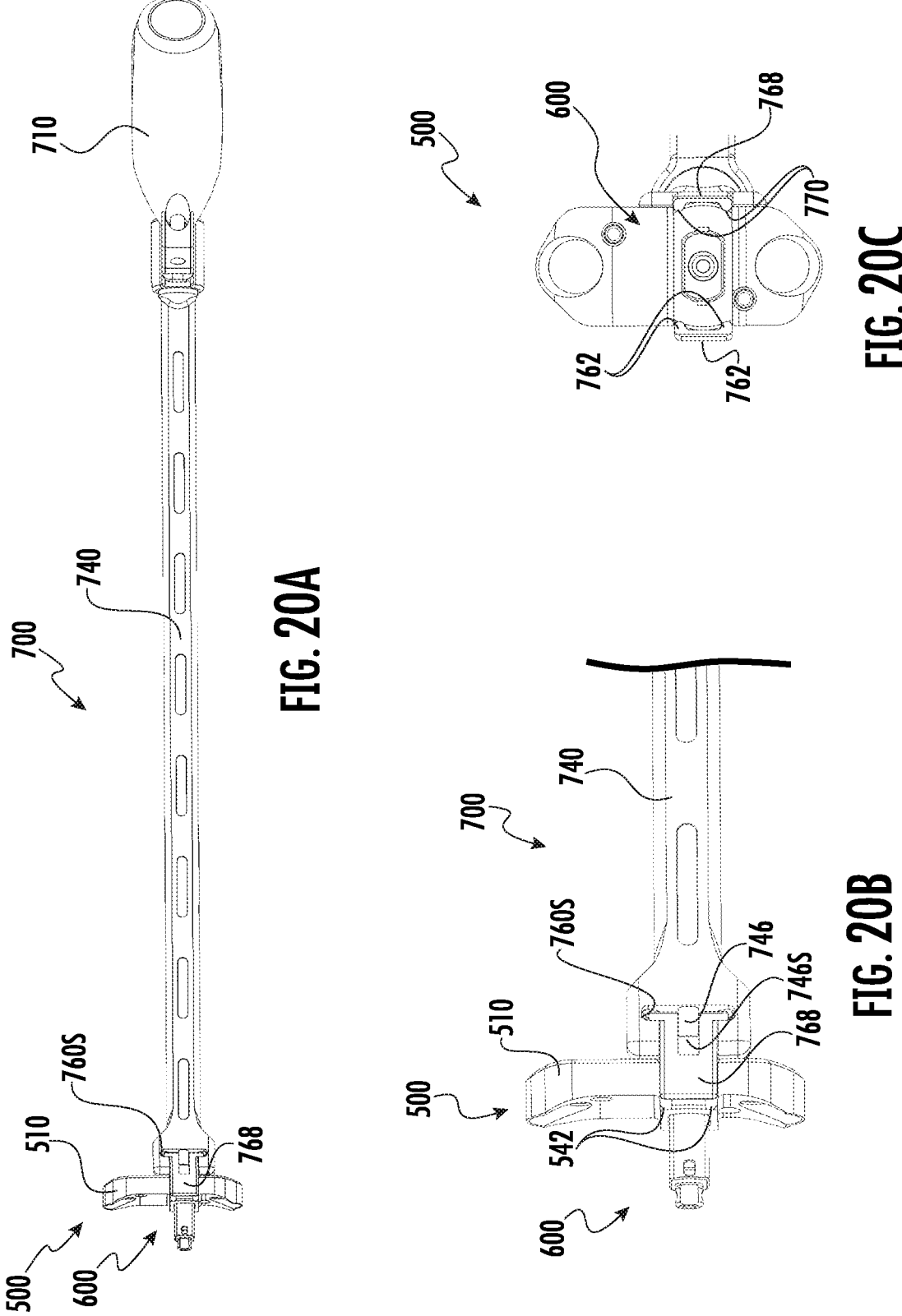
FIG. 20A is a bottom view of the plate assembly installation tool of FIG. 18, engaging an exemplary plate assembly.
FIG. 20B is a partial view of a distal portion of the plate assembly installation tool of FIG. 20A.
FIG. 20C is an end view of the distal portion of the plate assembly installation tool of FIG. 20B.

Turning to FIG. 19A, a plate assembly installation tool 700 includes a handle 710, and an elongate extension 740, which terminates in a distal end 760. The handle 710 may include a retaining system 720 that may be used to retain the handle 710 with, and rotatably align the handle 710 relative to, the elongate extension 740, providing a greater freedom of use. The distal end 760 may include a first arm 762 having one or more protrusions 764 adapted to mate with one or more protrusions of a plate assembly, protrusions 542 and 544 of plate body 510 of plate assembly 500, for example. Further, the distal end 760 may include a second arm 768 coupled to the distal end 760 of the installation tool 700. The second arm 768 may be positioned within a slot 760S, as best depicted in FIGS. 20A and 20B. The slot 760S allows the second arm to move laterally with respect to the elongate extension 740 as well as rotationally with respect to the slot 760S. In this way, the second arm 768 rotates and compresses upon a plate body of a plate assembly allowing the installation tool to hold the plate assembly for installation within a patient. The second arm 768 may include protrusions 770 adapted to couple to one or more protrusions of a plate assembly, protrusions 542 and 544 of plate body 510 of plate assembly 500, for example. As is described in greater detail below, the second arm 768 is rotatably and slidably attached to the distal end 760 of the installation tool 700 to facilitate connection to a plate assembly, such as plate assembly 500, or other plate assemblies described or contemplated herein. The distal end 760 may further include a lumen 780 through which a portion of a tool may be positioned to operate a plate assembly, as described above.

Figure 19B:
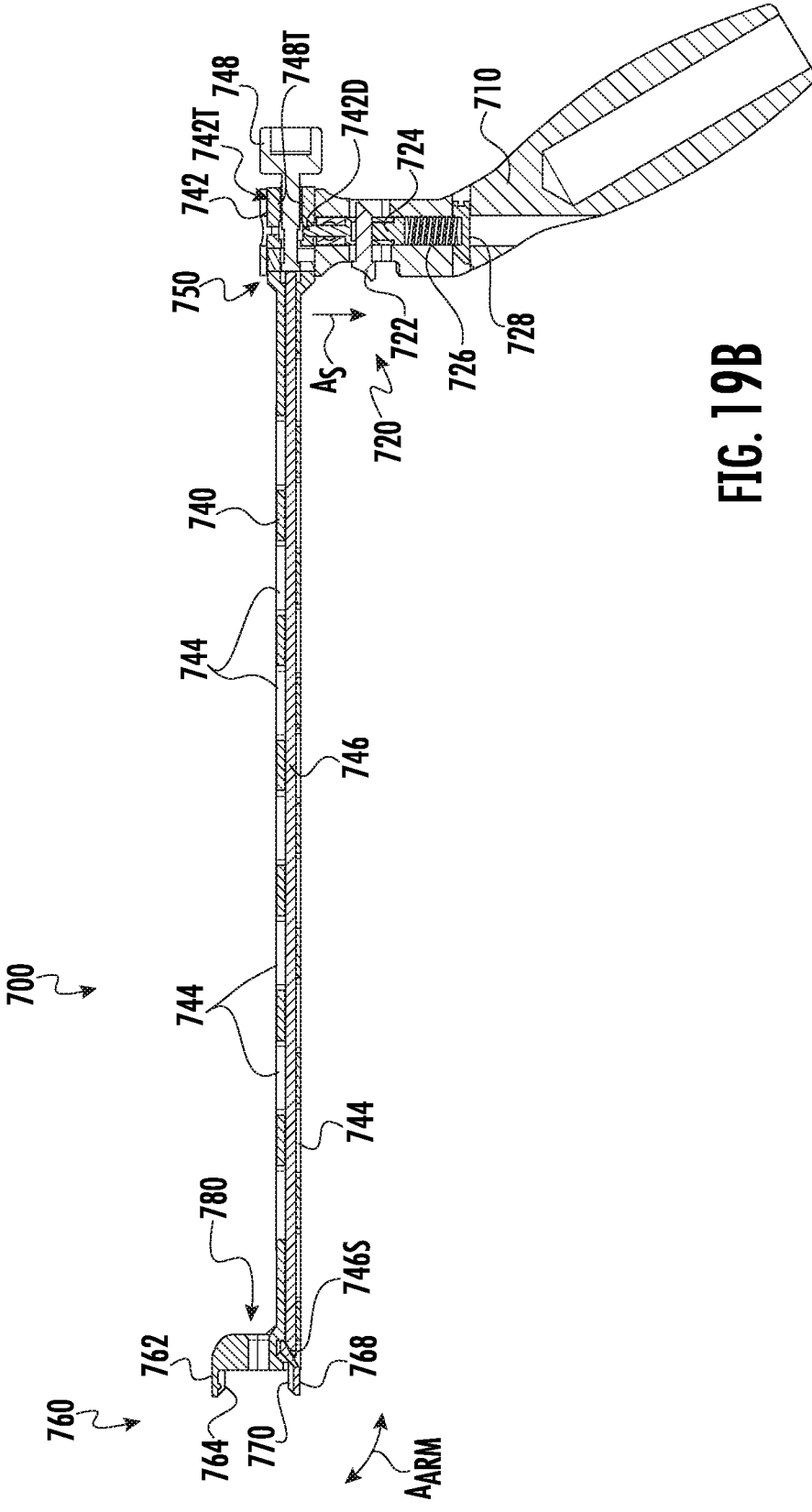
FIG. 19B is a side section view of the plate assembly installation tool of FIG. 18.

Now turning also to FIG. 19B, the retaining system 720 may include a sliding activator 722 coupled to a member 724. Member 724 may include a distal end 724D and a proximal end 724P, the proximal end 724P engaging a spring 726 and a retainer 728. The spring and retainer 728 allowing for the momentary depression of the sliding actuator 722. The distal end 724D of the member 724 is configured to enter one of a plurality of openings radially positioned about elongate extension 740. In operation, once the sliding actuator is depressed, the distal end 724D of the member 724 disengages from the elongate extension 740. The handle 710 may then be rotated with respect to the elongate extension 740, as desired, the sliding actuator released when the desired location is obtained. The elongate extension 740 may include a lumen therethrough, which may be generated through the creation of recesses 744 on alternating sides of the elongate extension 740, as depicted. The lumen may end in a proximal opening 742 of elongate extension 740, the proximal opening 742 including a threaded portion 742T. The lumen of the elongate extension 740 may be sized to slidably receive an elongate actuator 746 which includes a sloped surface 746S at its distal end. Once the elongate actuator 746 is positioned within the lumen of the elongate extension 740, a rotatable actuator 748 may be positioned within the proximal opening of the extension 740. The rotatable actuator 748 may include a threaded portion 748T that may interface with the threaded portion of the elongate extension 740 proximal end 742, the distal end of the rotatable actuator 748 coupling to the proximal end of the elongate actuator 746 at an interface point 750. Rotation of the rotatable actuator 748 allows the rotatable actuator 748 to move distally in the lumen of the elongate extension 740, effectively pushing the elongate actuator 746 in a distal direction, the sloped surface 746S of the actuator 746 pushing the second arm 768 resulting in the second arm 768 rotating in a direction as shown by arrow $A_{arm}$. In this way, the distal end 760 of the installation tool 700 can fixedly attach to a plate assembly, such as plate assembly 500, for installation thereof.

Turning now to FIGS. 20A-20C, an installation tool 700 is depicted grasping a plate assembly 500, incorporating coupler 600. In particular, upon application of rotational actuation of the rotatable actuator 748, elongate actuator 746 closes second arm 768 against the plate body 510 of plate assembly 500. Once the arms 762, 768 have closed about the plate assembly 500, protrusions 764, 770 of the arms 762, 768, respectively, couple to recesses 542, 544 of the plate assembly 500. Once the plate assembly 500 is operably positioned, adjacent to an intervertebral device positioned adjacent to vertebral bodies for example, the elongate member 620 may be operably engaged with a tool passing through lumen 780 to couple the plate assembly 500 to the intervertebral device. Alternatively, the installation tool may be utilized to position the plate assembly 500 adjacent to vertebral bodies while the plate assembly is fixedly attached to the vertebral bodies, using one or more vertebral body screws for example, both the intervertebral device and the plate assembly 500 being independently coupled to vertebral bodies.

Figure 21:
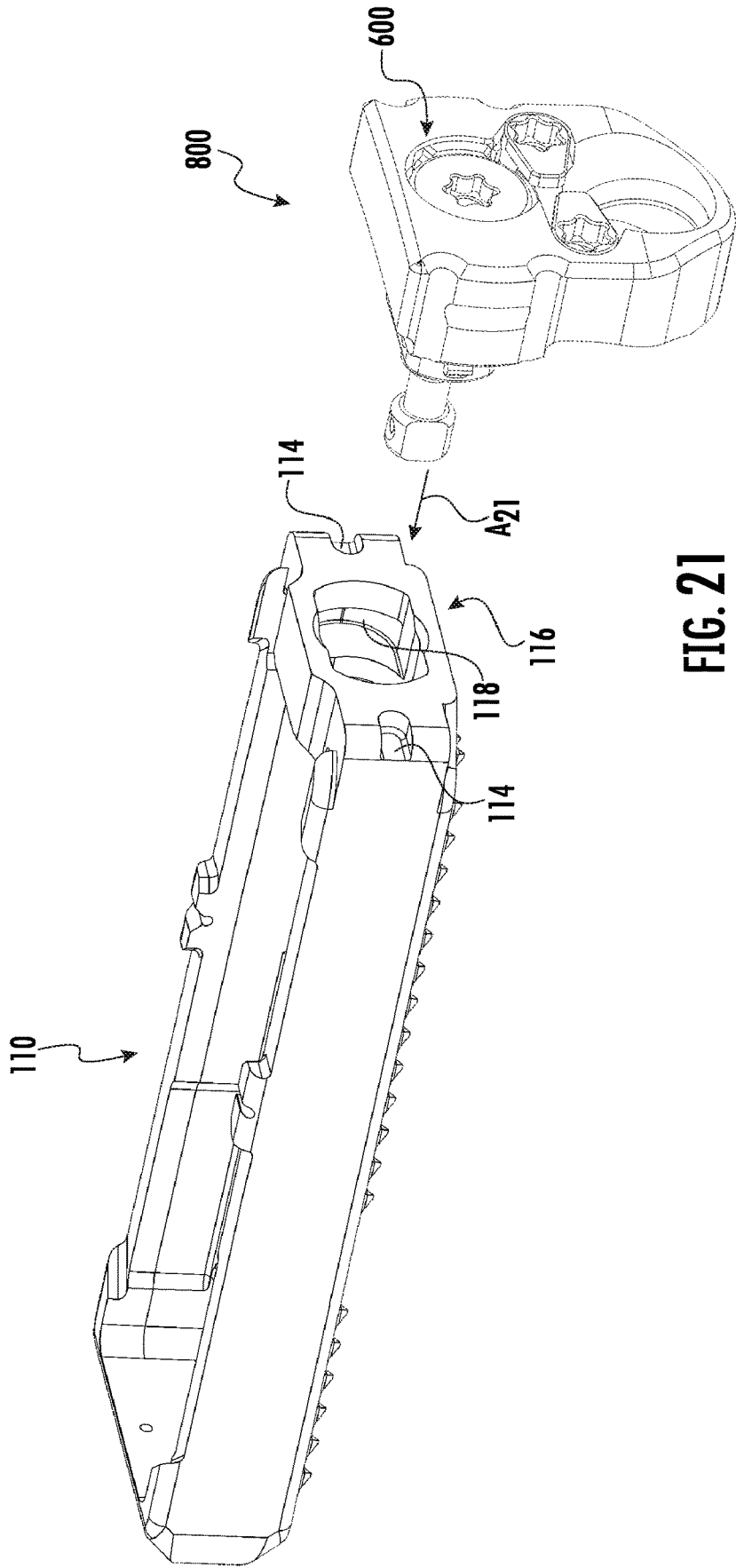
FIG. 21 is a system view of a portion of the intervertebral device of FIG. 1A and yet another exemplary plate assembly.

Turning to FIG. 21, a system view of a portion of the intervertebral device of FIG. 1A and another exemplary plate assembly 800 is depicted. More particularly, for simplicity, only the base 110 of the intervertebral device 100 is depicted, the base 110 including the distal opening 116 having a groove 118 on an inner surface thereof, and grooves 114. The plate assembly 800 may be similar to the plate assembly 500 described above in some aspects, but is adapted to only fixedly attach to one vertebral body, as well as the associated intervertebral device. The plate assembly 800 may also include the coupler 600. In operation, as with plate assembly 500, the plate assembly 800 is moved toward and interfaces with the base 110, for example, when the base 110, as part of an intervertebral device 100, is positioned between vertebral bodies. As the plate assembly 800 is moved toward the base 110 in a direction depicted by arrow A21 a portion of the coupler 600 enters the opening 116 of the base 100 and is operated, as described above with respect to plate assembly 500, to engage a portion of the groove 118 to fixedly attach the plate assembly 800 to the base 110 of the intervertebral device 100.

Figures 22A, 22B:
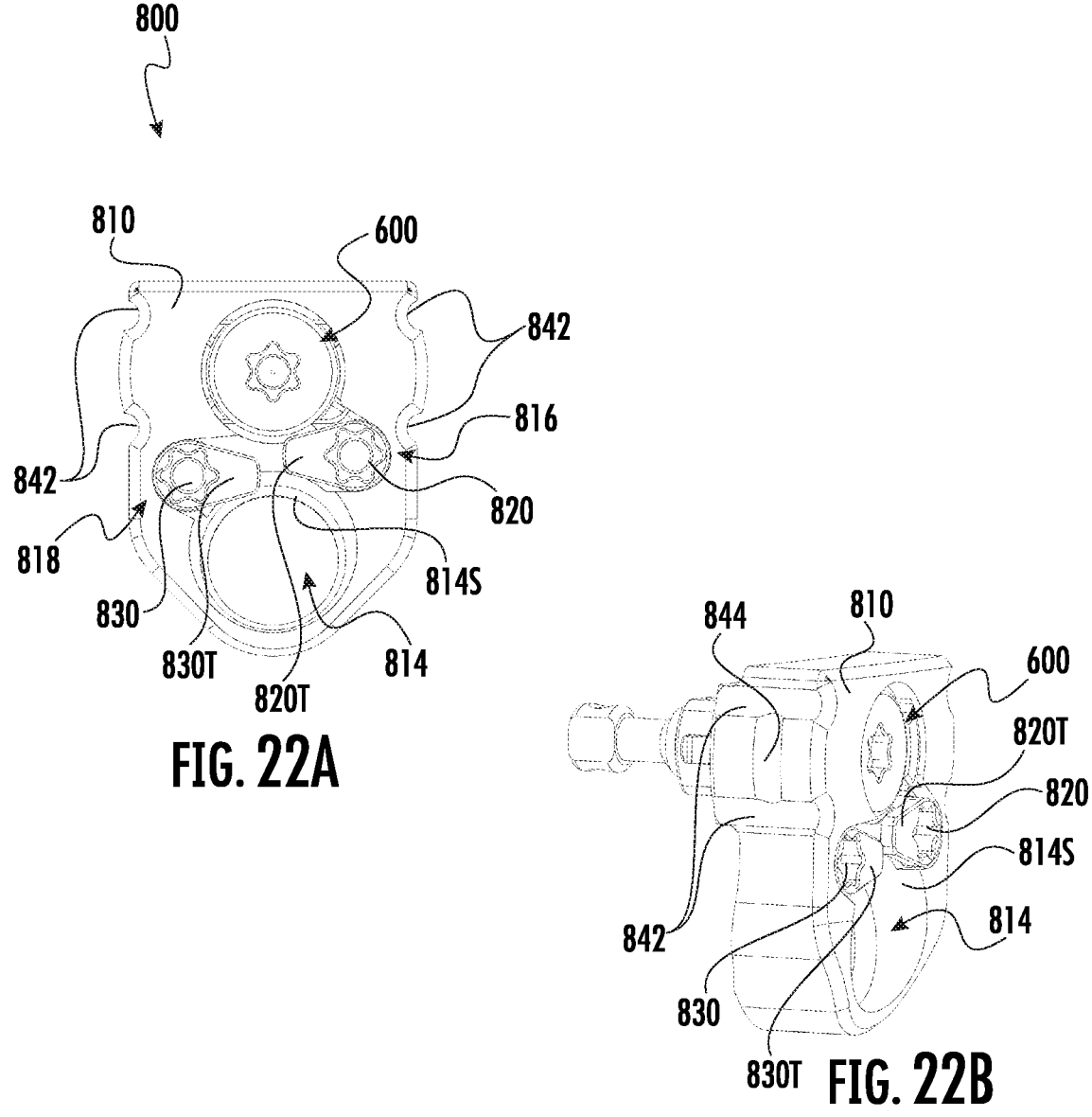
FIG. 22A is a front view of the exemplary plate assembly of FIG. 21.
FIG. 22B is a perspective view of the exemplary plate assembly of FIG. 22A.

Turning to FIGS. 22A and 22B, the plate assembly 800 may include a plate body 810 and the coupler 600, the coupler being adapted to interface the plate assembly 800 with the intervertebral device 100, as described above relative to plate assembly 500. The plate body 810 may further include an opening 814 adapted to accept a vertebral body screw, such as vertebral body screw 20 of FIG. 18A, to fixedly attach the plate body 810 of the plate assembly 800 to an adjacent vertebral body. The opening 814 may include one or more inner curved surfaces 814S configured to mate with corresponding curved surfaces on the head of an associated vertebral body screw, such as head 24 of vertebral body screw 20. In this way, the vertebral body screw may have a wider range of angular configurations with respect to a vertical axis of the body 810 of the plate assembly 800.

Plate Body 810 may include an additional opening 816 adapted to receive a first tab lock 820. The tab lock 820 may include one or more tab portions or tabs 820T. The tab lock 820 may have a lumen therethrough and once positioned within the plate body 810, the portion of the tab lock 820 opposite to the tab 820T may be swaged to rotatably secure the tab lock 820 to the plate body 810. Once the coupler 600 is operably deployed such that the plate assembly 800 is fixedly coupled to an intervertebral device, the tab lock 820 may be operated to prevent the elongate member 620 from backing out of the coupler 600, for example. Plate body 810 may include an additional opening 818 adapted to receive a second tab lock 830 including one or more tab portions 830T. The tab lock 830 may be recessed in a portion of the surface of plate body 810. As with tab lock 820, the tab lock 830 may include a lumen therethrough, the end opposite the tab 830T being swaged to allow for rotational movement of the tab lock 830, but preventing axial movement of the tab lock 830 back out of the opening 818.

The plate body 810 may include an opening 840 configured to accept the coupler 600, similar to the opening 540 of plate body 510. As with opening 540, opening 840 may include one or more curvilinear surfaces 840S. The one or more curvilinear surfaces 840S may allow the coupler 600 to couple to the plate body 510 in a number of different axial orientations. For example, once the coupler 600 is positioned within at least a portion of opening 840, a longitudinal axis of the coupler 600 may be non-parallel to a longitudinal axis of opening 840, similar to a ball joint, allowing for case of coupling between the plate assembly 800 and an intervertebral device during operation.

Figures 22C, 22D, 22E:
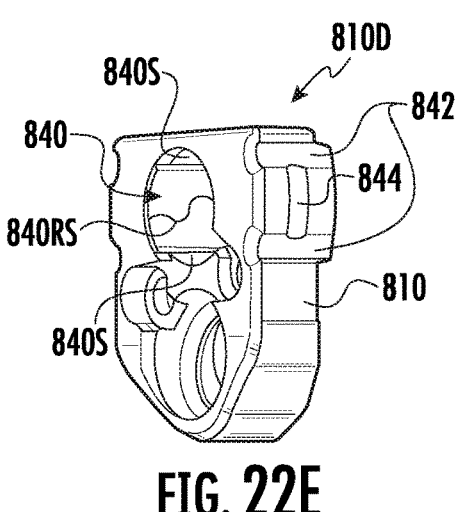
FIG. 22C is a side view of the exemplary plate assembly of FIG. 22A.
FIG. 22D is a top view of the exemplary plate assembly of FIG. 22A.
FIG. 22E is a perspective view of the plate body of the exemplary plate assembly of FIG. 22A.

Turning also to FIG. 22C, a side elevational view of the plate assembly 800 is depicted. As shown, the plate 810 of the plate assembly 800 may include a curved back surface 832, which may provide a better mating surface for an adjacent vertebral body. The body 810 may also include a protrusion 834, which protrudes away from the back surface 832 of the body 810 to allow for interfacing with an intervertebral device, such as device 100, while also allowing suitable space to interface with an adjacent vertebral body. Additionally, the protrusion 834 may have dimensions suitable to hold the back surface 832 of the body 810 a known desired distance away from the adjacent vertebral body during use. Furthermore, the body 810 may be selected to have a suitable width to provide a desired stiffness to help fixedly hold an intervertebral device to an adjacent vertebral body. Turning also to FIG. 22D, where a top view of the plate assembly 800 is depicted, the coupler 600, as described above, may further include one or more protrusions 630 adapted to interface with a portion of an intervertebral device, the groove 118 of the base 110 of the intervertebral device 100, for example, to fixedly hold the plate assembly 800 to the intervertebral device 100, as discussed in greater detail above with respect plate assembly 500 and FIGS. 17A-17C.

Turning to FIG. 22E, the plate body 810 may include alternative attributes interfacing with a coupler, such as coupler 600. In particular, opening 840 of body 810 may include additional retaining surfaces 840RS. A coupler, such as coupler 600, may be positioned within opening 840 from a distal side 810D of plate body 810. The retaining surfaces 840RS of the opening 840 may interfere with the housing 610 to prevent the housing from passing completely through opening 840 of the plate body 810. Once the coupler 600 is provided within the opening 840, the elongate member 640 can then be screwed into the coupler 600. The bottom surfaces of the elongate member 640 screw head may couple with opening surfaces 840S. In this way, the body portion 810 of the plate assembly 800 is positioned between the housing 610 and the elongate member 640 of the coupler 600. The cap 625 may then be attached to the elongate member 640. The coupler 600 may then be coupled to an intervertebral device, as described herein.

Figure 23A:
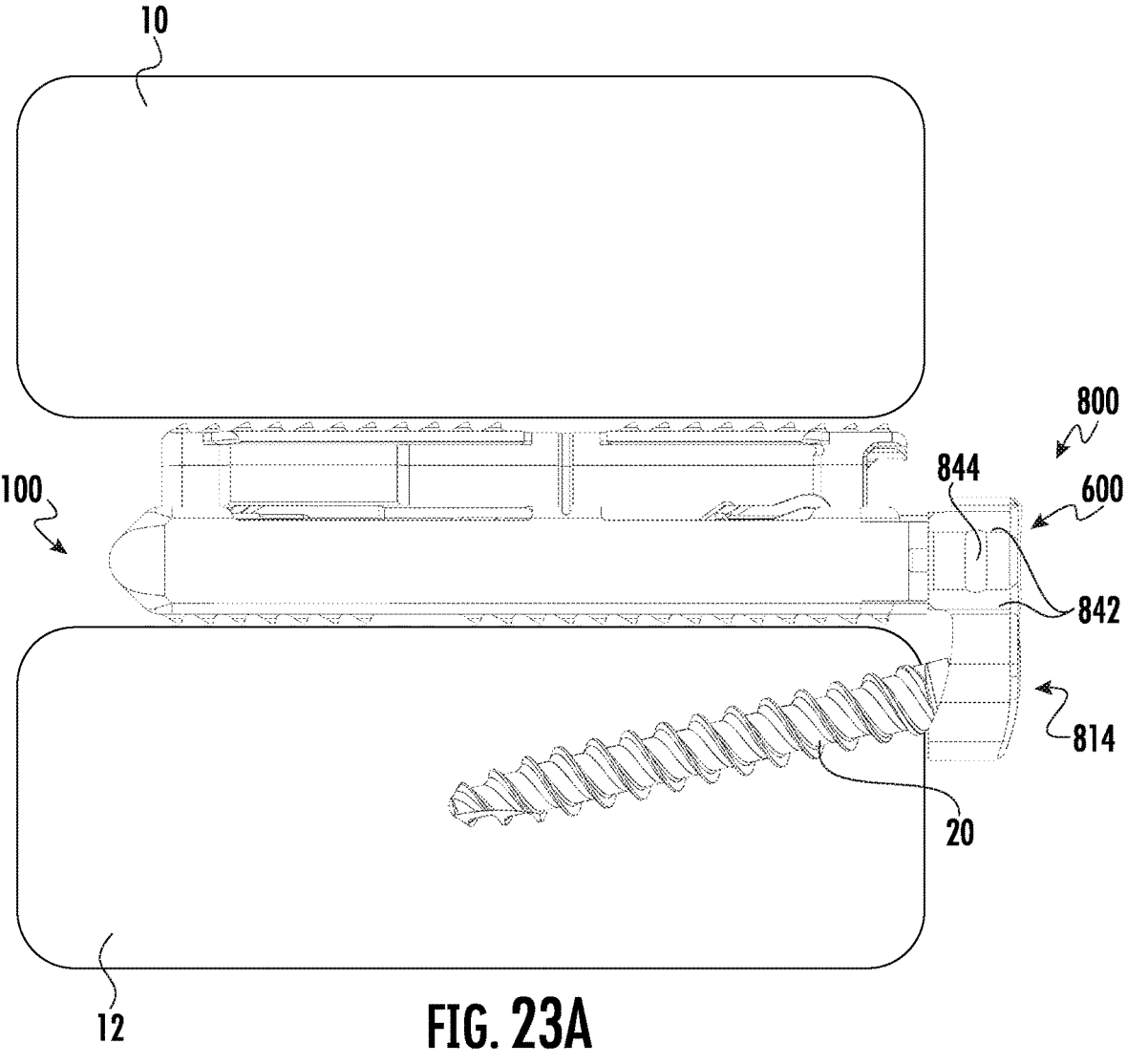
FIG. 23A is a symbolic side view of the plate assembly of FIG. 22A coupled to both, the intervertebral device of FIG. 1A and an adjacent vertebral body.
Figure 23B:
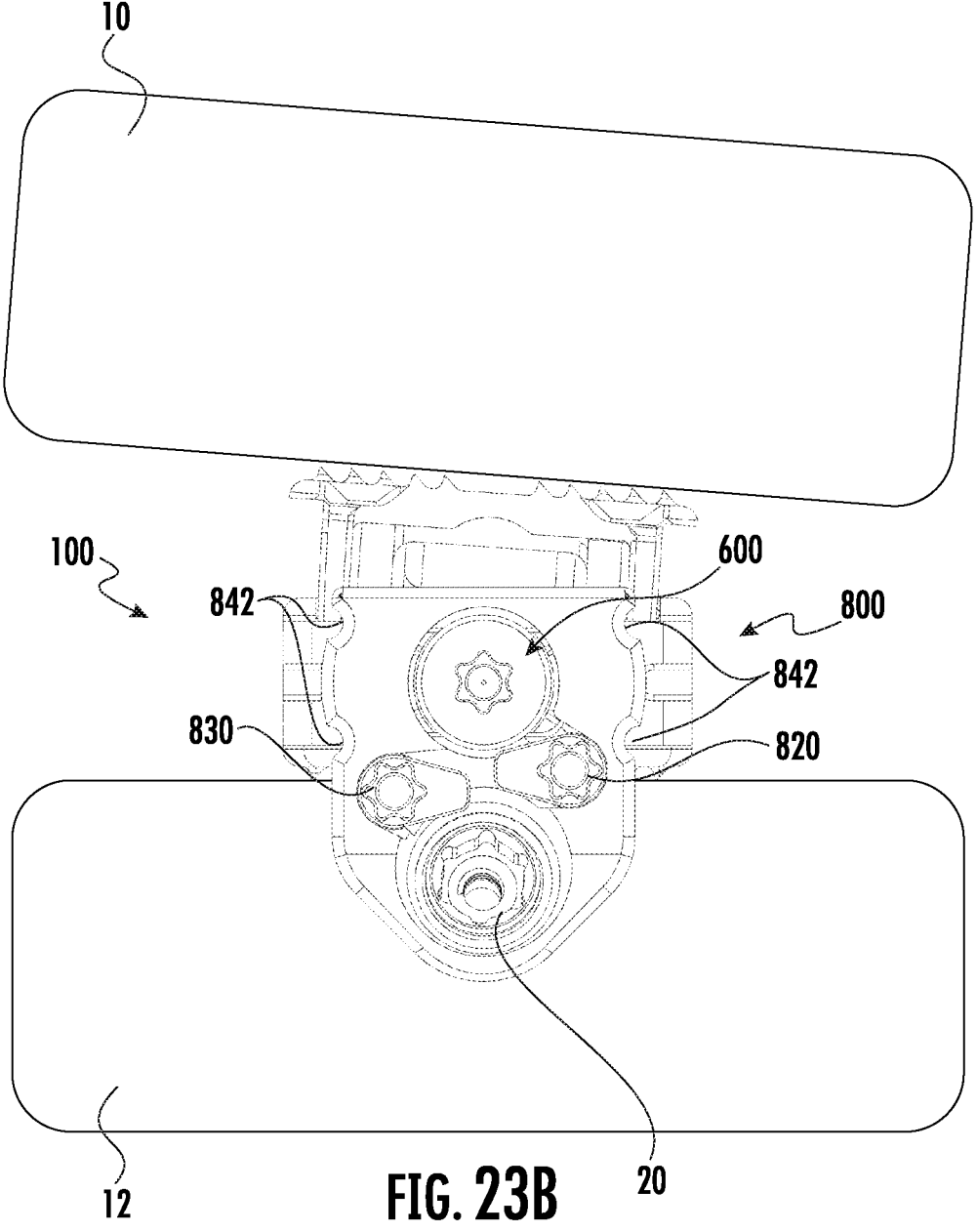
FIG. 23B is a symbolic end view of the plate assembly of FIG. 22A coupled to both, the intervertebral device of FIG. 1A and the adjacent vertebral body of FIG. 23A.

Turning to FIGS. 23A and 23B, exemplary positioning of the plate assembly 800 relative to an interventional device and an adjacent vertebral body is described. The depictions of FIGS. 23A and 23B are for illustrative purposes only and, therefore, are not necessarily to scale. FIG. 23A depicts an exemplary placement of an intervertebral device, such as intervertebral device 100, in an expanded configuration between first vertebral body 10 and second vertebral body 12. Once positioned, the plate assembly 800 may then be position adjacent to and coupled with the intervertebral device 100, as described with respect to plate assembly 500 and FIG. 11D above. Once the plate assembly 800 is coupled to the intervertebral device 100, the plate assembly 800 may be fixedly attached to an adjacent vertebral body through the use of a vertebral body screw, such as vertebral body screw 20. For example, a vertebral body screw 20 may be advanced through opening 814 of the plate 810 and into the vertebral body 12, as generally depicted. Turning to FIG. 23B, an end view of the plate assembly 800 coupled to the intervertebral device 100 and adjacent vertebral body 14 is depicted. As shown, once the vertebral body screw 20 is positioned, the tab locks 820, 830 may be rotationally operated to position tab portions 820T, 830T over the elongate member 620 and vertebral body screw 20, respectively, maintaining the position of the screw 20 and elongate member 620 relative to the coupler 600. As should be apparent, while FIGS. 23A and 23B depict the plate assembly interfacing with vertebral body 12, the plate assembly 800 may be rotationally positioned such that the vertebral body screw 20 engages vertebral body 10, rather than vertebral body 12, if desired.

Figure 24:
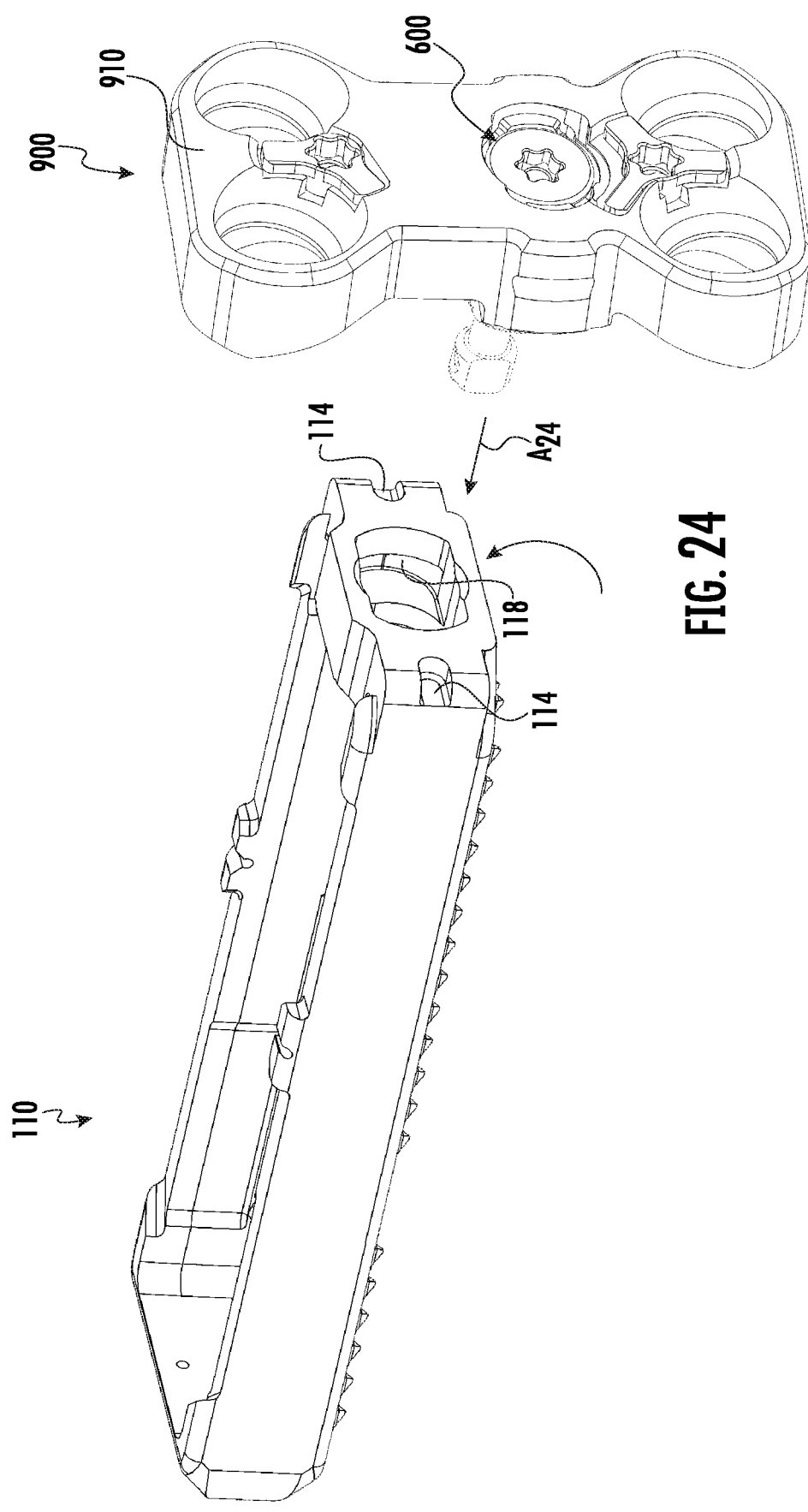
FIG. 24 is a system view of a portion of the intervertebral device of FIG. 1A and yet another exemplary plate assembly.

Turning to FIG. 24, a system view of a portion of the intervertebral device of FIG. 1A and another exemplary plate assembly 900 is depicted. More particularly, for simplicity, only the base 110 of the intervertebral device 100 is depicted, the base 110 including the distal opening 116 having a groove 118 on an inner surface thereof, and grooves 114. The plate assembly 900 may be similar to the plate assembly 500 described above in some aspects, but is adapted to fixedly attach to adjacent vertebral bodies utilizing multiple vertebral body screws, as well as the associated intervertebral device. The plate assembly 900 may also include the coupler 600. In operation, as with plate assembly 500, the plate assembly 900 is moved toward and interfaces with the base 110, for example, when the base 110, as part of an intervertebral device 100, is positioned between vertebral bodies. As the plate assembly 900 is moved toward the base 110 in a direction depicted by arrow $A_{24}$ a portion of the coupler 600 enters the opening 116 of the base 100 and is operated, as described above with respect to plate assembly 500, to engage a portion of the groove 118 to fixedly attach the plate assembly 900 to the base 110 of the intervertebral device 100.

Figures 25A, 25B:
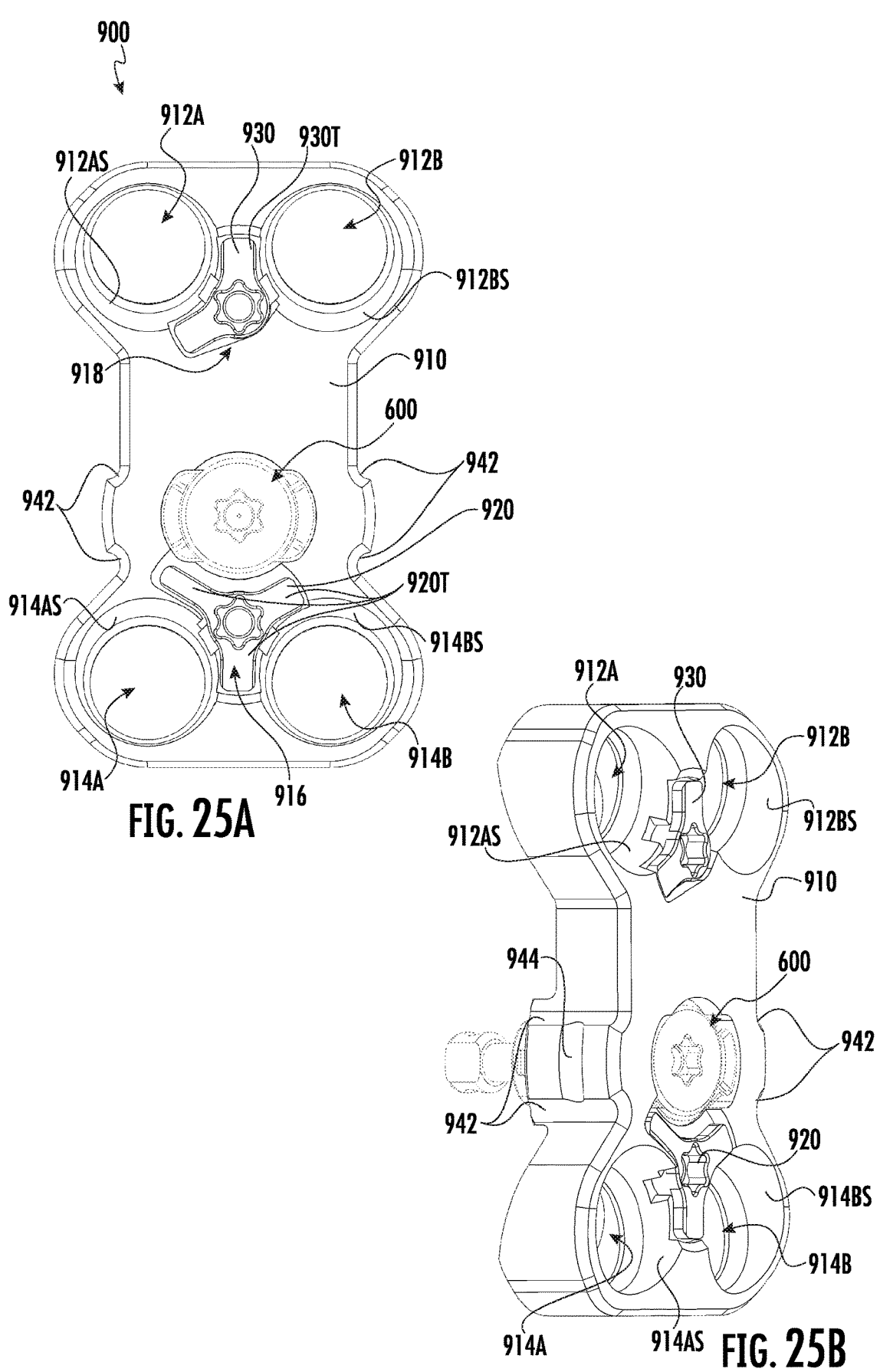
FIG. 25A is a front view of the exemplary plate assembly of FIG. 24.
FIG. 25B is a perspective view of the exemplary plate assembly of FIG. 25A.

Turning to FIGS. 25A and 25B, the plate assembly 900 may include a plate body 910 and coupler 600, the coupler being adapted to interface the plate assembly 900 with the intervertebral device 100. The plate body 910 may further include openings 912A and 912B and openings 914A and 914B. Each of the openings 912A, 912B, 914A, 914B are adapted to accept a vertebral body screw, such as vertebral body screw 20 of FIGS. 12C and 12D, to fixedly attach the plate body 910 of the plate assembly 900 to adjacent vertebral bodies. The openings 912A, 912B, 914A, 914B may include inner surfaces 912AS, 912BS, 914AS, 914BS, respectively, having curved surfaces configured to mate with corresponding curved surfaces on the head of an associated vertebral body screw, such as head 24 of vertebral body screw 20. In this way, the vertebral body screw may have a wider range of angular configurations with respect to a vertical axis of plate body 910 of the plate assembly 900.

The plate body 910 may include an opening 940 configured to accept the coupler 600, similar to the opening 540 of plate body 510. As with opening 540, opening 940 may include one or more curvilinear surfaces 940S. The one or more curvilinear surfaces 940S may allow the coupler 600 to couple to the plate body 910 in a number of different axial orientations. For example, once the coupler 600 is positioned within at least a portion of opening 940, a longitudinal axis of the coupler 600 may be non-parallel to a longitudinal axis of opening 940, similar to a ball joint, allowing for case of coupling between the plate assembly 900 and an intervertebral device during operation.

Plate Body 910 may include an additional opening 916 adapted to receive a first tab lock 920, which may include one or more tab portions or tabs 920T. The tab lock 920 may have a lumen therethrough and once positioned within the plate body 910, the portion of the tab lock 920 opposite to the tab 920T may be swaged to secure the tab lock 920 to the plate body 910. The coupler 600 may include an elongate member 620 having a threaded portion, as is discussed in greater detail below, and once the elongate member 620 is deployed a second tab 920T of the tab lock 920 may cover the head of the elongate member 620, preventing the elongate member 620 from backing out of the coupler 600, for example. Plate body 910 may include an additional opening 918 adapted to receive a second tab lock 930, which may include one or more tab portions 930T. The tab lock 930 may be recessed in a portion of the surface of plate body 910. As with other tab locks described or contemplated herein, the tab lock 930 may include a lumen therethrough, the end opposite the tab 930T being swaged to allow for rotational movement of the tab lock 930, but preventing axial movement of the tab lock 930 back out of the opening 918.

Figures 25C, 25D:
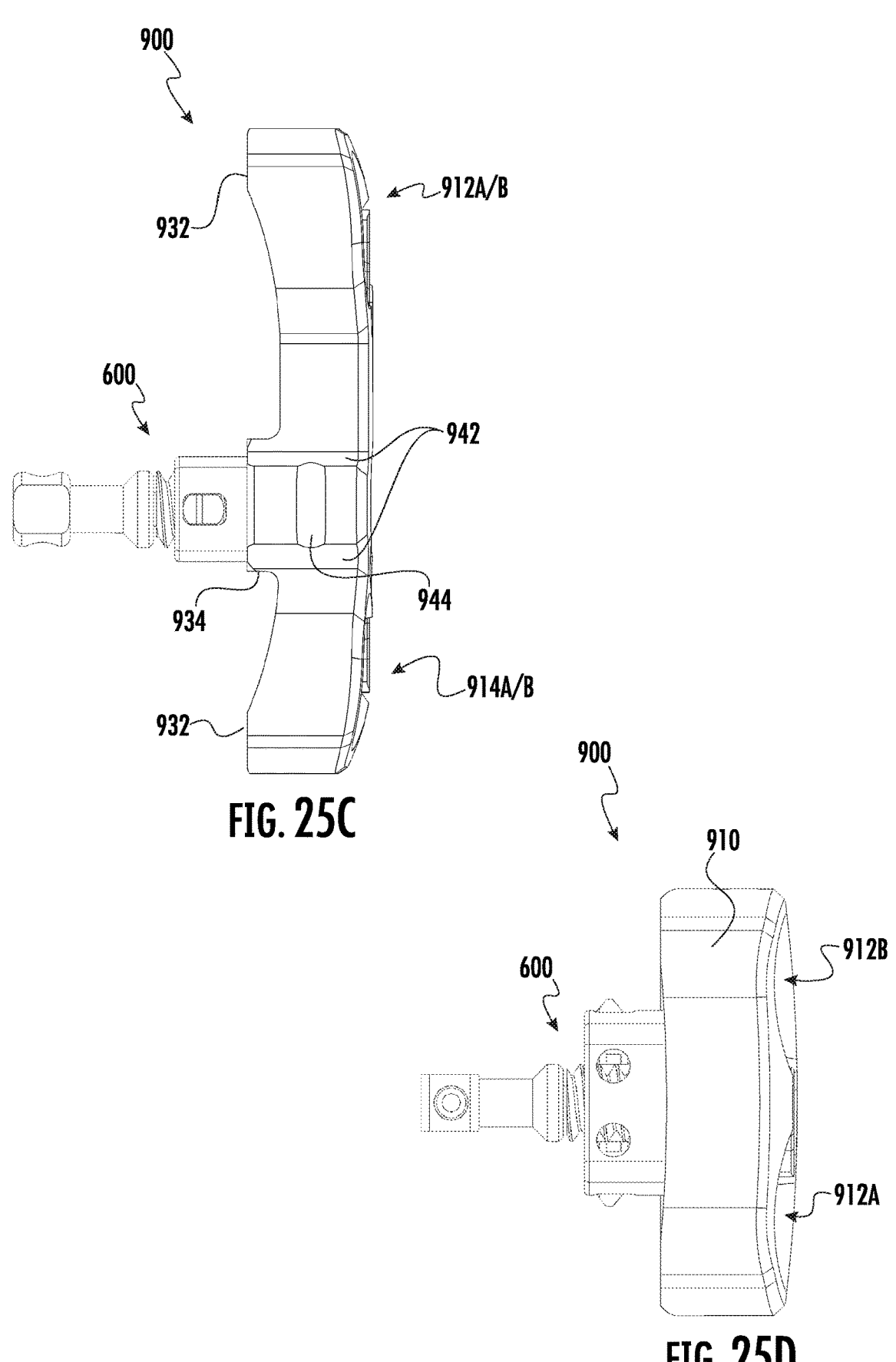
FIG. 25C is a side view of the exemplary plate assembly of FIG. 25A.
FIG. 25D is a top view of the exemplary plate assembly of FIG. 25A.

Turning also to FIG. 25C, a side elevational view of the plate assembly 900 is depicted. As shown, the plate body 910 of the plate assembly 900 may include a curved back surface 932, which may provide a better mating surface for adjacent vertebral bodies. The plate body 910 may also include a protrusion 934, which protrudes away from the back surface 932 of the plate body 910 to allow for interfacing with an intervertebral device, such as device 100, while also allowing suitable space to interface with adjacent vertebral bodies. Additionally, the protrusion 934 may have dimensions suitable to hold the back surface 932 of the plate body 910 a known desired distance away from the adjacent vertebral bodies during use. Furthermore, the plate body 910 may be selected to have a suitable width to provide a desired stiffness to help fixedly hold an intervertebral device to the adjacent vertebral bodies. Turning also to FIG. 25D, where a top view of the plate assembly 900 is depicted, the coupler 600 further includes one or more protrusions 630 adapted to interface with a portion of an intervertebral device, the groove 118 of the base 110 of the intervertebral device 100, for example, to fixedly hold the plate assembly 900 to the intervertebral device 100, as discussed in greater detail with respect to plate assembly 500 and FIGS. 17A-17C.

Figure 26A:
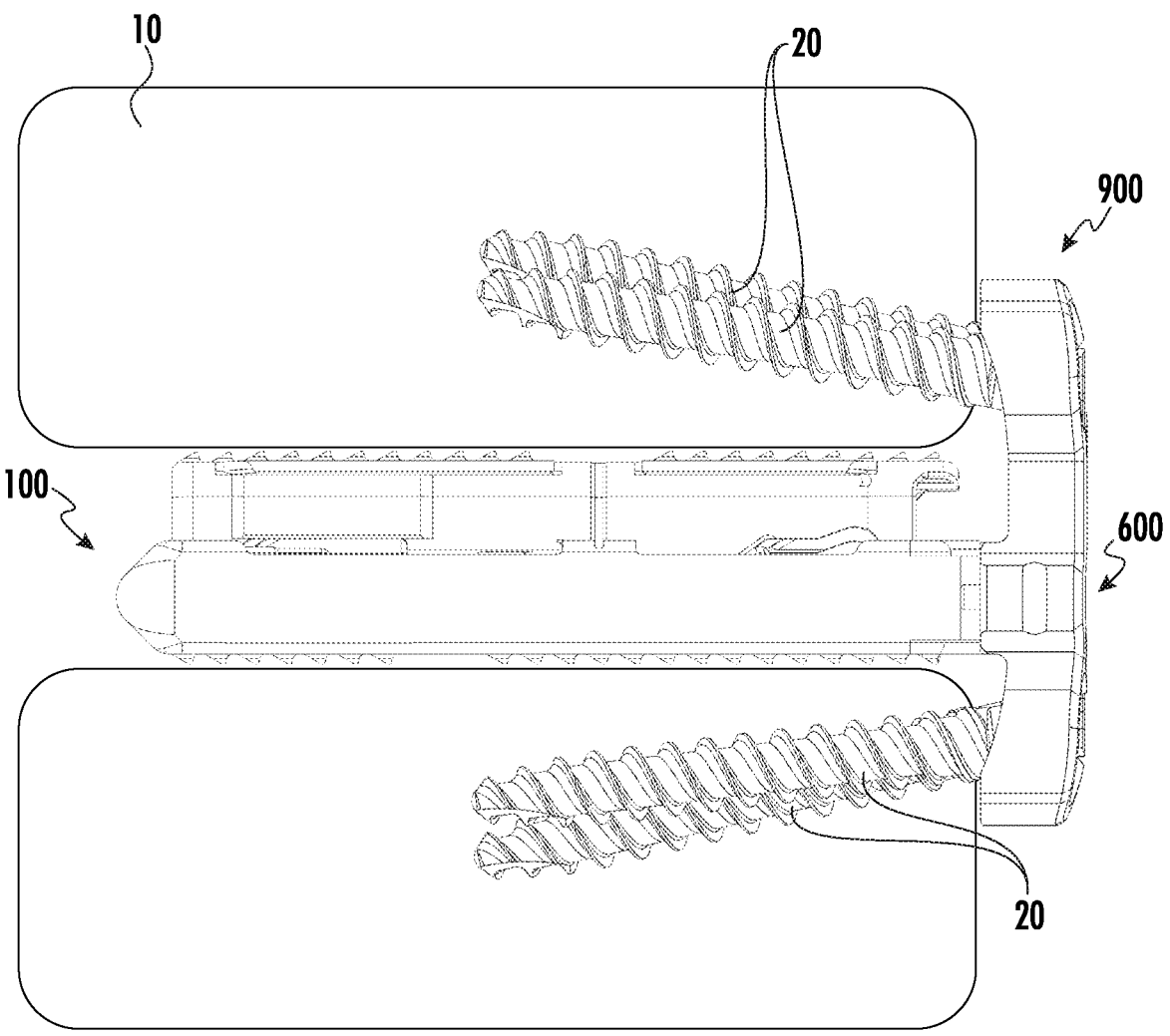
FIG. 26A is a symbolic side view of the plate assembly of FIG. 25A coupled to both, the intervertebral device of FIG. 1A and adjacent vertebral bodies.
Figure 26B:
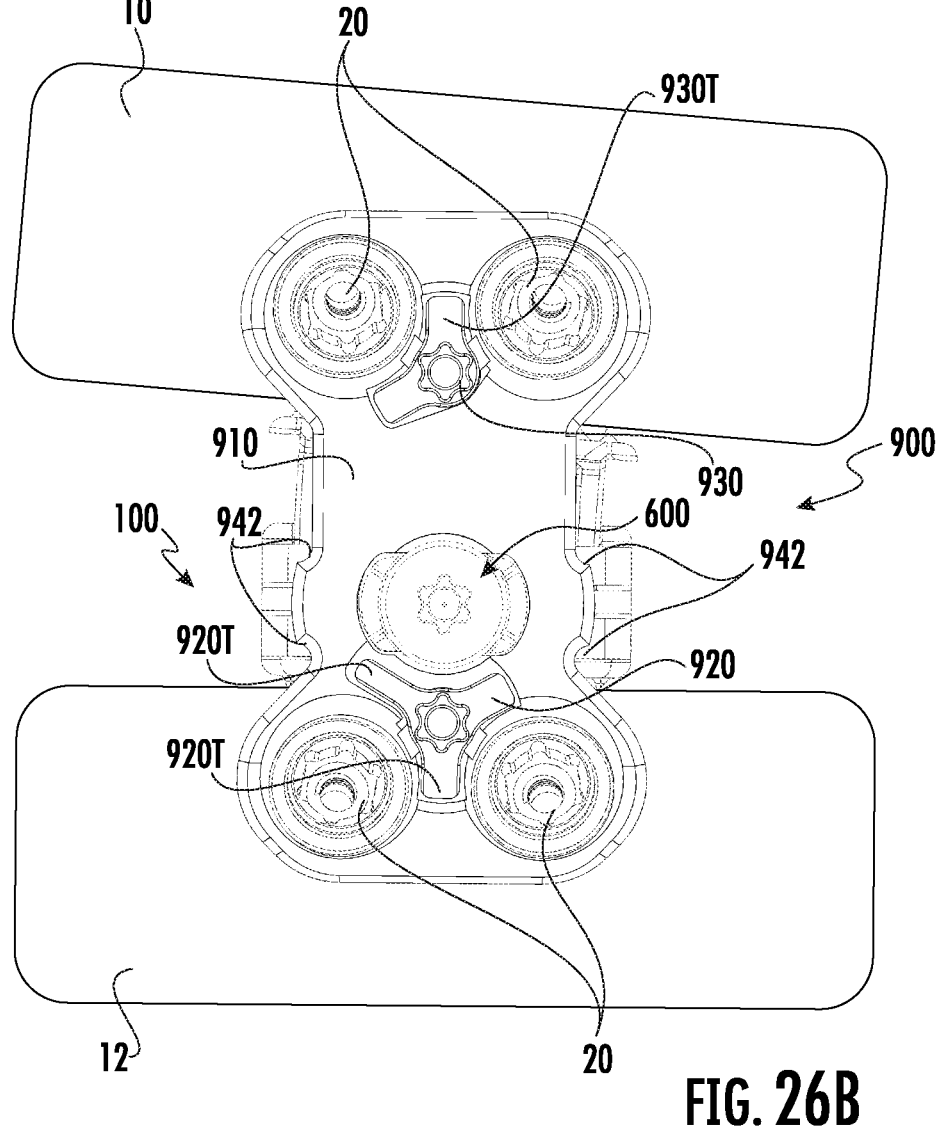
FIG. 26B is a symbolic end view of the plate assembly of FIG. 25A coupled to both, the intervertebral device of FIG. 1A and adjacent vertebral bodies.
Figure 26C:
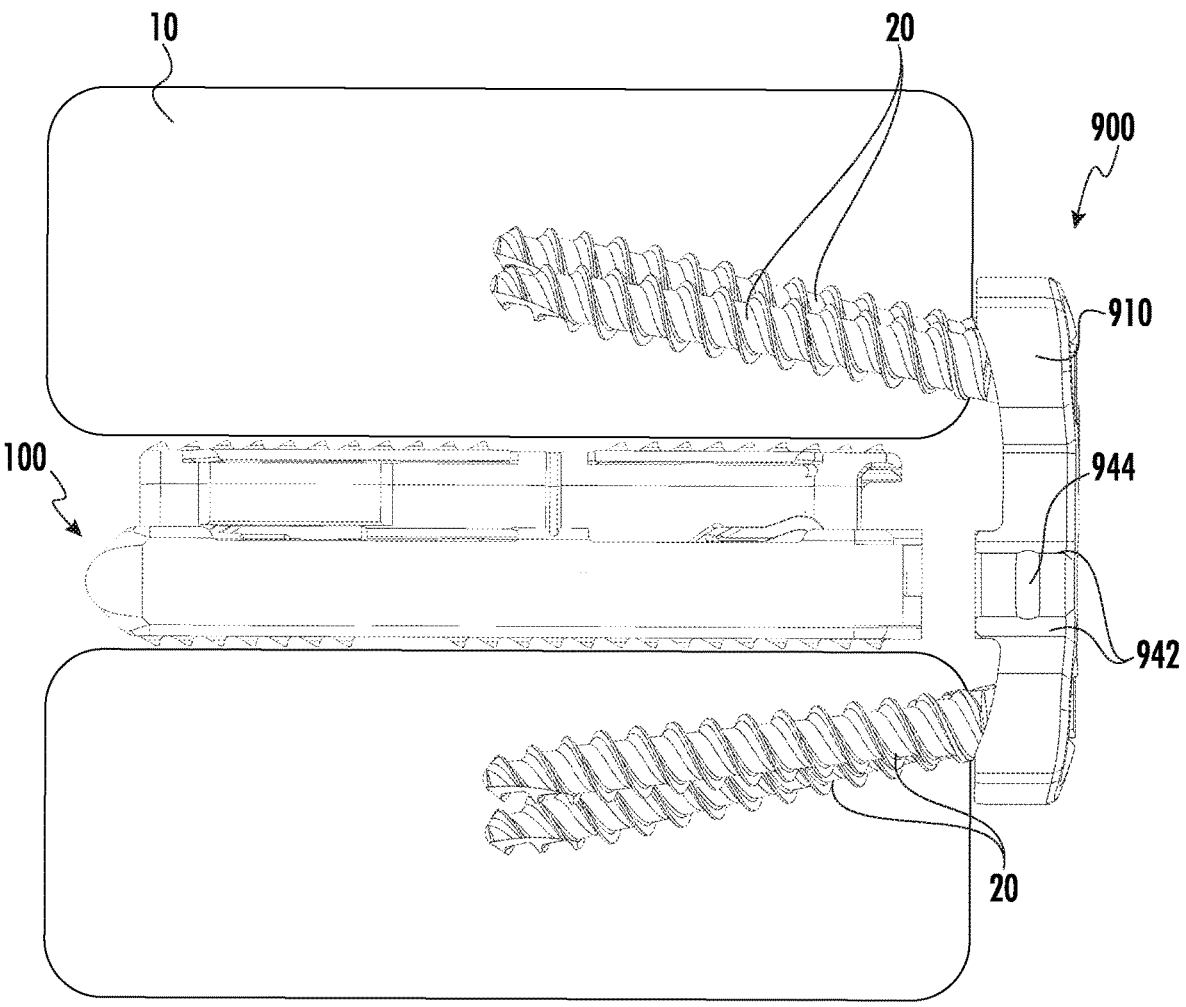
FIG. 26C is a symbolic side view of the plate assembly of FIG. 25A and the intervertebral device of FIG. 1A, each independently coupled to adjacent vertebral bodies.

Turning to FIGS. 26A-26C, exemplary positioning of the plate assembly 900 relative to an interventional device and adjacent vertebral bodies is described. The depictions of FIGS. 26A-26C are for illustrative purposes only and, therefore, are not necessarily to scale. FIG. 26A depicts an exemplary placement of an intervertebral device, such as intervertebral device 100, in an expanded configuration between first vertebral body 10 and second vertebral body 12. Once positioned, the plate assembly 900 may then be position adjacent to and coupled with the intervertebral device 100, as described with respect to plate assembly 500 and FIG. 11D above. Once the plate assembly 900 is coupled to the intervertebral device 100, the plate assembly 900 may be fixedly attached to the adjacent vertebral bodies through the use of one or more vertebral body screws, such as vertebral body screws 20. For example, first and second vertebral body screws 20 may be advanced through openings 912A, 912B of the plate 910, respectively, and into the first vertebral body 10, and third and fourth vertebral body screws 20 may be advanced through openings 914A, 914B of the plate 910, respectively, as generally depicted. Turning to FIG. 26B, an end view of the plate assembly 900 coupled to the intervertebral device 100 and adjacent vertebral bodies 10, 12 is depicted. As shown, once the vertebral body screws 20 are positioned, the tab locks 920, 930 may be rotationally operated to position tab portions 920T, 930T over corresponding heads of vertebral body screws 20, as well as elongate member 620 of coupler 600, maintaining the position of the screws 20 and elongate member 620 relative to the coupler 600.

While the plate assembly 900 may include a coupler for coupling to an intervertebral device, the plate assembly 900 can be utilized independently from an intervertebral device, if desired. For example, with reference to FIG. 26C, once the intervertebral device 100 is positioned adjacent to vertebral bodies 10, 12, the plate 910 of the plate assembly 900 may be positioned and fixedly attached to the adjacent vertebral bodies 10, 12 through the use of vertebral body screws 20, as described immediately above. In this way, the plate 910 and the intervertebral device 100 are independently coupled to the adjacent vertebral bodies 10, 12.

The retention assemblies described or contemplated herein may be made from any suitable biocompatible material, including but not limited to metals, metal alloys (e.g. stainless steel) and polymers (e.g. polycarbonate), and may be formed using any appropriate process, such as screw-machining or molding (e.g. injection molding), or printing.

It should be understood that features of any one of the retention assemblies described herein may be applied to any other intervertebral devices than those described herein. For example, any intervertebral device may be configured to include structures found in base 110 of intervertebral device 100 to interface the intervertebral device to the retention assemblies described herein. of the above-described intervertebral devices, as appropriate.

The invention claimed is:

1. An intervertebral device (100) comprising:
   a base element (110), the base element (110) including a proximal end (112) and a distal end (130), a first side (122), a second side (124), a bottom surface (136), and a top surface, the base (110) including a distal opening (116) for attachment of a plate assembly (300) so that the plate assembly is oriented orthogonally with respect to a longitudinal axis of the base element,
   the plate assembly (300) having a coupler (400), which provides an interface between the plate assembly (300) and the base element (110) of the intervertebral device (100), the coupler (400) includes an inner housing (410) sized to fit within the distal opening (116), the inner housing (410) having a first lumen (410L1) extending therethrough, a second lumen (41012), which is oriented substantially perpendicular to the first lumen (410L1), and positioned to intersect with the first lumen,
   one or more protrusion members (430) being positioned within the second lumen and constructed to translate within the second lumen (410L2),
   an elongate member (420) constructed and arranged to translate through the first lumen (41011) to interact with the one or more protrusion members (430), wherein moving the elongate member in a first direction causes translation of the one or more protrusion members, causing the one or more protrusion members to extend beyond an outer perimeter of the inner housing (410) to engage the base element (110).

2. The intervertebral device of claim 1 wherein the distal opening (116) includes a circumferential groove (118) on an inner surface thereof positioned to cooperate with the one or more protrusion members (430) in the extended position.

3. The intervertebral device of claim 2 wherein the circumferential groove (118) and the one or more protrusion members (430) cooperate to allow for angular attachment between the base element (110) and the plate assembly (300).

4. The intervertebral device (100) of claim 3 wherein the plate assembly (300) is secured to the base element (110) to allow for polyaxial alignment between the base element and the plate assembly (300).

5. The intervertebral device (100) of claim 4 wherein the plate assembly (300) can be fixedly secured to the base element (110), allowing for the polyaxial alignment between the base element and the plate assembly (300).

6. The intervertebral device (100) of claim 1 wherein the elongate member (420) is threaded, the first lumen (410L1) having internal threads to cooperate with the elongate member to allow the elongate member to be rotated clockwise and anti-clockwise to provide controlled inward and outward traversal of the elongate member.

7. The intervertebral device (100) of claim 6 wherein the elongate member (420) includes a cap (625A) secured to the elongate member to allow rotation of the elongate member without rotation of the cap (625A).

8. The intervertebral device (100) of claim 7 wherein the cap (625A) includes a transition surface (626A) which cooperates with the one or more protrusion members (430) to cause the one or more protrusion members (430) to translate within the second lumen (410L2).

9. The intervertebral device (100) of claim 8 wherein the transition surface (626A) is conical in shape.

10. The intervertebral device (100) of claim 8 wherein the protrusion (430) includes a first side surface (430C1), a second side surface (430C2), a third side surface (430C3), a fourth side surface (43004), a bottom surface (430B), and a top surface (430T).

11. The intervertebral device (100) of claim 10 wherein the top surface (430T) further includes a flat top surface (434) formed by the relative separation of a first sloped surface (436A) and a second sloped surface (436B).

12. The intervertebral device (100) of claim 10 wherein the protrusion (430) includes tabs (438) which maintain a desired orientation of the protrusion (430) with respect to the housing (410) as the protrusion (430) translates along the lumen (410L2) of the housing (410), the lumen (410L2) having corresponding flat surfaces (430C2) (430C4) respectively to cooperate with the tabs (438).

13. The intervertebral device (100) of claim 1 including a plate cap (440) positioned to circumscribe the inner housing (410).

14. The intervertebral device (100) of claim 13 wherein the plate cap (440) includes a keyed outer shape constructed to cooperate with aperture (340) of the plate assembly (300) to key the plate cap (440) to the coupler (400), requiring them to move together.

15. The intervertebral device (100) of claim 1 wherein the coupler (400) further includes a plate cap (440) adapted to be slidably coupled to the housing (410), the plate cap (440) including a lip portion (442) adapted to slidably couple with one or more surfaces of the plate body (310), to allow for a longitudinal axis of the elongate coupler (420) to be non-parallel to a longitudinal axis of opening (340) of the plate (310).

* * * * *